United States Patent [19]

Miyadera et al.

[11] Patent Number: 4,639,441
[45] Date of Patent: Jan. 27, 1987

[54] 2-PENEM-3-CARBOXYLIC ACID DERIVATIVES AND USE

[75] Inventors: Tetsuo Miyadera; Yukio Sugimura; Teruo Tanaka; Toshihiko Hashimoto; Kimio Iino; Shinichi Sugawara, all of Tokyo, Japan

[73] Assignee: Sankyo Company Limited, Tokyo, Japan

[21] Appl. No.: 582,152

[22] Filed: Feb. 24, 1984

Related U.S. Application Data

[63] Continuation of Ser. No. 241,737, Mar. 9, 1981.

[30] Foreign Application Priority Data

Mar. 10, 1980 [JP] Japan .................................. 55-30013
Mar. 17, 1980 [JP] Japan .................................. 55-33529
Jun. 3, 1980 [JP] Japan .................................. 55-74761

[51] Int. Cl.$^4$ .................. C07D 499/00; A61K 31/425
[52] U.S. Cl. ........................................ 514/195; 540/310
[58] Field of Search ................ 260/245.2 R, 245.2 T; 514/195

[56] References Cited

U.S. PATENT DOCUMENTS 4,168,314 8/1982 Afonso et al. ............... 260/245.2 R
4,272,437 6/1981 Menand et al. ...................... 544/236
4,301,074 11/1981 Christensen et al. ......... 260/245.2 R
4,474,793 10/1984 Ross et al. ............................ 424/270

FOREIGN PATENT DOCUMENTS 54-66695 5/1979 Japan .
55-9034 1/1980 Japan .
2013674A 8/1979 United Kingdom .
2013674 8/1979 United Kingdom .

*Primary Examiner*—Nicholas S. Rizzo
*Attorney, Agent, or Firm*—Frishauf, Holtz, Goodman & Woodward

[57] ABSTRACT

Compounds of formula (I):

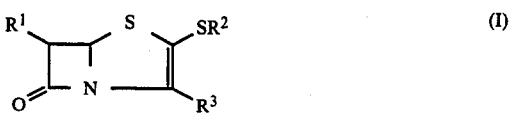

in which:

$R^1$ represents a hydrogen atom, an alkyl group, an alkoxy group or various substituted alkyl groups;
$R^2$ represents a hydrogen atom, a group of formula

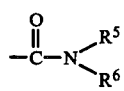

(in which $R^5$ and $R^6$ each represents an alkyl group, an aralkyl group or an aryl group, or $R^5$ and $R^6$ together represent a nitrogen-containing heterocyclic group) or a group of formula

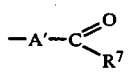

(in which $R^7$ represents a hydrogen atom, a substituted or unsubstituted alkyl group, a substituted or unsubstituted amino group, a cyclic amino group, a hydroxy group, an alkoxy group, an aryloxy group, an aralkyloxy group, a substituted or unsubstituted hydrazino group or a guanidino group, and A' represents a bivalent saturated aliphatic hydrocarbon group); and
$R^3$ represents a carboxy group or a protected carboxy group; and pharmaceutically acceptable salts thereof are valuable antibiotics and may be prepared from the corresponding 1-(protected carboxymethyl)-4-alkylthio-azetidin-2-one.

28 Claims, No Drawings

2-PENEM-3-CARBOXYLIC ACID DERIVATIVES AND USE

This application is a continuation of application Ser. No. 241,737, filed Mar. 9, 1981.

BACKGROUND TO THE INVENTION

The present invention relates to a series of new 2-penem-3-carboxylic acid derivatives, to their preparation and to their use as antibiotics for the treatment of a variety of diseases caused by bacteria, both Gram-positive and Gram-negative.

The penicillins form a well-known class of antibiotics, which have found considerable use in human and animal therapy for many years. Indeed, benzyl penicillin, which was the first of the antibiotics to come into general therapeutic use, is still widely used today. Chemically, the penicillins have in common a β-lactam-type structure commonly referred to as "penam", which has the following formula:

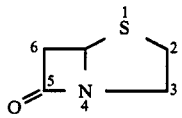

However, although the penicillins still form a valuable weapon in the pharmaceutical armory, the development of new, and often penicillin-resistant, strains of pathogenic bacteria has increasingly made it necessary to search for new types of antibiotic. Recently, some interest has been shown in compounds having a penem structure, that is compounds having a double bond between the carbon atoms in the 2- and 3-positions of the basic penam structure. The penem structure is as follows:

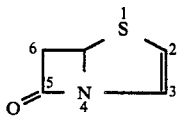

These penam and penem structures form the basis for the semi-systematic nomenclature of the penicillin derivatives and this nomenclature is generally accepted by those skilled in the art throughout the world and is used herein, the numbering system being that illustrated on the above structures.

Of the penem derivatives discovered in recent years, a compound thought to be of particular value is 2-[(2-aminoethyl)thio]-6-(1-hydroxyethyl)penem-3-carboxylic acid, which has the formula:

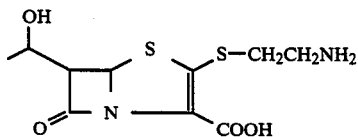

This compound was disclosed by name in British Patent Specification No. 2013674A, and in U.S. Pat. No. 4,168,314. However, valuable though the activity of 2-[(2-aminoethyl)thio]-6-(1-hydroxyethyl)penem-3-carboxylic acid is, we have now discovered a series of related compounds having an antibiotic activity, particularly against Gram-negative bacteria, greater than that of this known compound; moreover, there are indications that the acute toxicities of the compounds of the present invention are significantly lower than that of the prior art compound.

BRIEF SUMMARY OF INVENTION

The new 2-penem-3-carboxylic acid derivatives of the present invention are those compounds of formula (I):

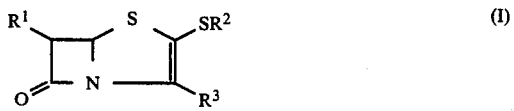

in which:
$R^1$ represents a hydrogen atom, an alkyl group, an alkoxy group or a group of formula $R^4A-$ (in which $R^4$ represents a hydroxy group, an alkoxy group, an acyloxy group, an alkylsulphonyloxy group, an arylsulphonyloxy group, a trialkylsilyloxy group, a mercapto group, an alkylthio group, an amino group, an acylamino group or an azido group, and A represents a bivalent saturated aliphatic hydrocarbon group optionally having a trifluoromethyl and/or phenyl substituent);

$R^2$ represents a hydrogen atom, a group of formula

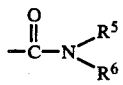

(in which $R^5$ and $R^6$ are the same or different and each represents an alkyl group, an aralkyl group or an aryl group, or $R^5$ and $R^6$, together with the nitrogen atom to which they are attached, represent a nitrogen-containing heterocyclic group optionally containing one or more other heteroatoms) or a group of formula

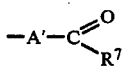

(in which $R^7$ represents a hydrogen atom, an alkyl group, an alkyl group having one or more halogen substituents, an aralkyl group, an aryl group, an amino group, an alkyl-substituted amino group, whose alkyl group or groups optionally have one or more hydroxy, amino, carboxy or protected carboxy substituents, a cyclic amino group, an amino group having one or more aryl, heterocyclic or aralkyl substituents, a hydroxy group, an alkoxy group, an aryloxy group, an aralkyloxy group, a hydrazino group, a hydrazino group having one or more alkyl, aralkyl or aryl substituents, a hydroxyamino group, an alkoxyamino group or a guanidino group, and $A'$ represents a bivalent saturated aliphatic hydrocarbon group); and $R^3$ represents a carboxy group or a protected carboxy group.

In a neutral medium the compounds of the invention in which $R^2$ represents a hydrogen atom do not normally exist in the thiol form shown in formula (I). Rather, they will normally exist in the thioketone form and have the formula (Ia):

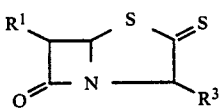  (Ia)

(in which $R^1$ and $R^3$ are as defined above). Accordingly, the invention also includes within its scope those tautomers of the compounds of formula (I) wherein $R^2$ represents a hydrogen atom.

Where $R^3$ represents a carboxy group and/or the group represented by $R^2$ includes a carboxy group, the compounds of the invention are carboxylic acids and hence can form salts. Accordingly, the invention also provides pharmaceutically acceptable salts of these compounds of the invention.

The compounds of the invention may be prepared by the following process:

(a) reacting a 4-alkylthio-azetidine-2-one of formula (II):

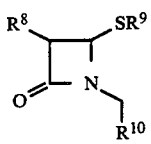  (II)

in which:

$R^8$ represents a hydrogen atom, an alkyl group, an alkoxy group or a group of formula $R^{14}A-$ (in which $R^{14}$ represents an alkoxy group, an acyloxy group, an alkylsulphonyloxy group, an arylsulphonyloxy group, a trialkylsilyloxy group, an acylthio group, an alkylthio group or an acylamino group, and A is as defined above)

$R^9$ represents a lower alkyl group; and $R^{10}$ represents a protected carboxy group;

with a base;

(b) reacting the product of step (a) with carbon disulphide;

(c) reacting the product of step (b) with a compound of formula (III):

  (III)

or a dicarboxylic acid dihalide,
or a compound of formula (IV):

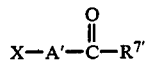  (IV)

or a compound of formula (V):

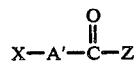  (V)

or a compound of formula (VI):

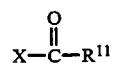  (VI)

(in which: X represents a halogen atom; Z represents a halogen atom or a lower alkoxycarbonyloxy group; $R^{7'}$ represents a hydrogen atom, an alkyl group, an alkyl group having one or more halogen substituents, an aralkyl group or an aryl group; $R^{11}$ represents an alkyl group, an aryl group or an aralkyl group; and A' is as defined above);

(d) halogenating the product of step (c) to give a compound of formula (VII) or (VIIa):

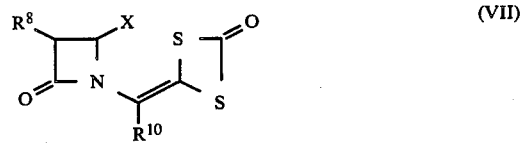  (VII)

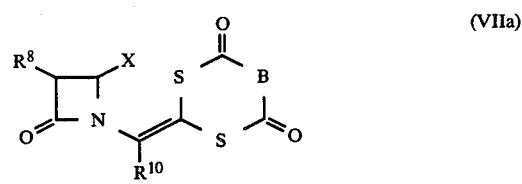  (VIIa)

(in which B represents a residue of the dicarboxylic acid)
or a compound of formula (VIII):

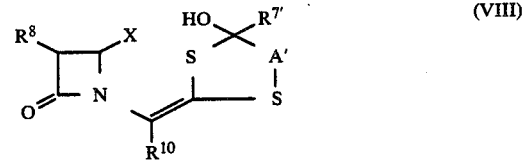  (VIII)

or a compound of formula (IX):

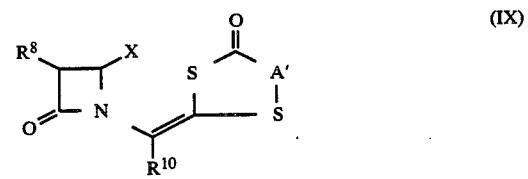  (IX)

or a compound of formula (X):

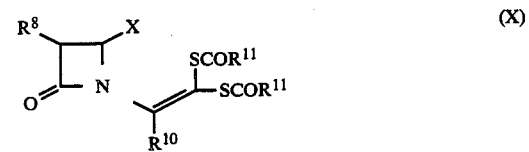  (X)

respectively;

(e) reacting said compound of formula (VII), (VIIa), (VIII) or (X) with a base to a give a compound of formula (XI):

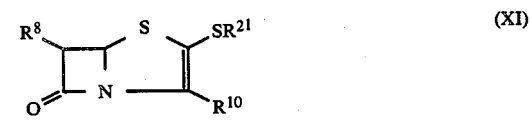  (XI)

(in which $R^{2'}$ represents a hydrogen atom or a group of formula

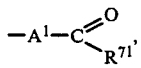

in which A' and R⁷' are as defined above); or
(e') reacting said compound of formula (VII) or (VIIa) with a compound of formula (XIII):

 (XIII)

(in which R⁵ and R⁶ are as defined above) to give a compound of formula (XIV):

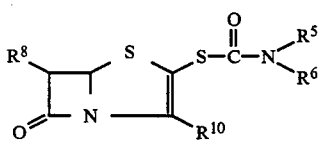 (XIV)

(in which R⁵, R⁶, R⁸ and R¹⁰ are as defined above);
(e'') reacting said compound of formula (IX) with a compound of formula (XV):

 (XV)

(in which R¹² represents a hydrogen atom or an alkyl group and R¹³ represents a hydrogen atom, an alkyl group, an alkyl group having one or more hydroxy, protected amino or protected carboxy substituents, an aryl group, a heterocyclic group, an aralkyl group, an amino group, an amino group having one or more alkyl, aralkyl or aryl substituents, a hydroxy group, an alkoxy group or an amidino group, or R¹² and R¹³, together with the nitrogen atom to which they are attached, represent a nitrogen-containing heterocyclic group optionally containing one or more other hetero- atoms) to give a compound of formula (XVI):

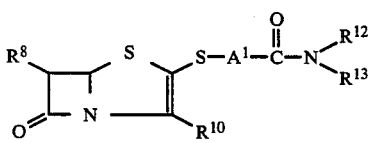 (XVI)

(in which R⁸, R¹⁰, R¹², R¹³ and A' are as defined above); or
(e''') reacting said compound of formula (IX) with a hydroxy compound of formula (XVII):

 (XVII)

in the presence of a base to give a compound of formula (XVIII):

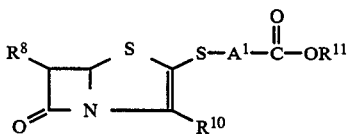 (XVIII)

(in which R⁸, R¹⁰, R¹¹ and A' are as defined above);
(f) if necessary, deprotecting any protected group and, if necessary, converting a hydroxy group represented by R⁴ to an acyloxy group, an azido group, an amino group, an acylamino group or an alkylthio group;
(g) optionally, reacting the product of step (e) in which R²' represents a hydrogen atom, that is to say a compound of formula (XII):

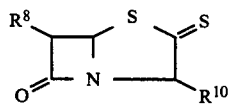 (XII)

before or after removing hydroxy-protecting groups and/or conversion of the hydroxy group represented by R⁴ in step (f) with a compound of formula (XIX):

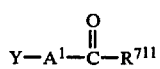 (XIX)

(in which R⁷'' represents a hydrogen atom, an alkyl group, an alkyl group having one or more halogen substituents, an aralkyl group, an aryl group, an amino group, an alkyl-substituted amino group, whose alkyl group or groups optionally have one or more protected hydroxy, protected amino or protected carboxy substituents, a cyclic amino group, an amino group having one or more aryl, heterocyclic or aralkyl substituents, a hydrazino group, a hydrazino group having one or more alkyl, aralkyl or aryl substituents, a hydroxyamino group, an alkoxyamino group or a guanidino group, and Y represents a halogen atom, an alkylsulphonyloxy group or an arylsulphonyloxy group) to give a compound of formula (XX):

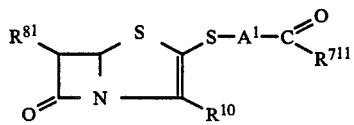 (XX)

(in which R⁸' represents any one of the groups represented by R¹ or R⁸, and R⁷'', R¹⁰ and A' are as defined above) and, if necessary, deprotecting any protected groups;
(h) optionally salifying the product of any preceding step.

The invention further provides a pharmaceutical composition comprising an antibiotic and a pharmaceutically acceptable carrier or diluent, wherein the antibiotic is a compound of formula (I) or a pharmaceutically acceptable salt thereof.

DETAILED DESCRIPTION OF INVENTION

In the compounds of the invention, where R¹ represents an alkyl group, it may be a straight or branched chain group and is preferably a lower alkyl group, for example a methyl, ethyl, propyl, isopropyl, butyl, isobutyl, sec-butyl, t-butyl, pentyl or isopentyl group. Where R¹ represents an alkoxy group, it may be a straight or branched chain alkoxy group and is preferably a lower alkoxy group, for example a methoxy, ethoxy, propoxy, isopropoxy, butoxy, isobutoxy, sec-butoxy, or t-butoxy group.

Where $R^1$ represents a group of formula $R^4A—$, $R^4$ may be an alkoxy group, which may be straight or branched-chain, preferably a lower alkoxy group, for example a methoxy, ethoxy, propoxy or isopropoxy group. Where $R^4$ represents an acyloxy group, it may be a lower aliphatic acyloxy group (e.g. an acetoxy, propionyloxy, butyryloxy or isobutyryloxy group) or an aralkyloxycarbonyloxy group (e.g. a benzyloxycarbonyloxy or p-nitrobenzyloxycarbonyloxy group). Where $R^4$ represents an alkylsulphonyloxy group, it is preferably a lower alkylsulphonyloxy group, for example a methanesulphonyloxy, ethanesulphonyloxy or propanesulphonyloxy group. Where $R^4$ represents an arylsulphonyloxy group, it is preferably a benzenesulphonyloxy or p-toluenesulphonyloxy group. Where $R^4$ represents a trialkylsilyloxy group, the alkyl groups are preferably lower alkyl groups and examples of such groups represented by $R^4$ are the trimethylsilyloxy and t-butyldimethylsilyl oxy groups. Where $R^4$ represents an alkylthio group, it is preferably a lower alkylthio group, for example a methylthio, ethylthio, propylthio or isopropylthio group. Where $R^4$ represents an acylamino group, it is preferably a lower aliphatic acylamino group, for example an acetylamino, propionylamino, butyrylamino or isobutyrylamino group.

Where $R^1$ represents a group of formula $R^4A—$, A represents a bivalent saturated aliphatic hydrocarbon group, e.g. an alkylene or alkylidene group, and may have a trifluoromethyl and/or phenyl substituent. Examples of such groups represented by A include the methylene, ethylene, ethylidene, trimethylene, propylidene, tetramethylene, butylidene, pentamethylene, pentylidene, 2,2,2-trifluoroethylidene, 3,3,3-trifluoropropylidene and benzylidene groups.

In the compounds of the invention, where $R^2$ represents a group of formula

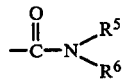

and $R^5$ or $R^6$ represents an alkyl group, it may be a straight or branched chain alkyl group and is preferably such a group having from 1 to 4 carbon atoms, for example a methyl, ethyl, propyl, isopropyl, butyl, isobutyl, sec-butyl or t-butyl group. Where $R^5$ or $R^6$ represents an aralkyl group, it may be a benzyl, phenethyl or phenylpropyl group and may, if desired, have one or more substituents in the aromatic ring. Such substituents include, for example, lower alkyl groups (for example methyl, ethyl, propyl or isopropyl groups), alkoxy groups (for example methoxy, ethoxy, propoxy or isopropoxy groups) or halogen atoms (for example fluorine, chlorine or bromine atoms). Where $R^5$ or $R^6$ represents an aryl group, it is preferably a phenyl group, which optionally has or more of the following substituents: lower alkyl groups (for example methyl, ethyl, propyl or isopropyl groups); lower alkoxy groups (for example methoxy, ethoxy, propoxy or isopropoxy groups); or halogen atoms (for example fluorine, chlorine or bromine atoms).

Alternatively, $R^5$ and $R^6$, together with the nitrogen atom to which they are attached, may represent a nitrogen-containing heterocyclic group, which may contain one or more other hetero-atoms in its ring (preferably nitrogen and/or oxygen atoms). Such heterocyclic rings may be substituted or unsubstituted and preferably have from 3 to 6 ring atoms. Examples of such heterocyclic groups include the 1-aziridinyl, 1-pyrrolidinyl, piperidino, 4-hydroxypiperidino, morpholino or 1-piperazinyl groups.

Where $R^2$ represents a group of formula

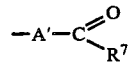

and $R^7$ represents an alkyl group, it may be a straight or branched chain alkyl group and is preferably a lower alkyl group, for example a methyl, ethyl, propyl, isopropyl, butyl, isobutyl, sec-butyl, t-butyl, pentyl or isopentyl group. Where $R^7$ represents a halogen-substituted alkyl group, it preferably has from 1 to 3 halogen substituents, e.g. chlorine, bromine or fluorine atoms; examples of such halogen-substituted alkyl groups include the chloromethyl, 2-bromoethyl, 2-bromopropyl and trifluoromethyl groups. Where $R^7$ represents an aralkyl group, it is preferably a benzyl, phenethyl or phenylpropyl group and its aromatic ring may have one or more of the following substituents: lower alkyl groups (e.g. methyl, ethyl, propyl or isopropyl groups); lower alkoxy groups (e.g. methoxy, ethoxy, propoxy or isopropoxy groups); and halogen atoms (e.g. fluorine, chlorine or bromine atoms). Where $R^7$ represents an aryl group, it is preferably a phenyl group and optionally has one or more of the following substituents: lower alkyl groups (e.g. methyl, ethyl, propyl or isopropyl groups); lower alkoxy groups (e.g. methoxy, ethoxy, propoxy or isopropoxy groups); and halogen atoms (e.g. fluorine, chlorine or bromine atoms). Where $R^7$ represents an alkyl-substituted amino group, the alkyl group or groups are preferably lower alkyl groups and examples of such alkyl-substituted amino groups include the methylamino, ethylamino, propylamino, isopropylamino, dimethylamino, diethylamino, dipropylamino and diisopropylamino groups. Such alkyl-substituted amino groups may themselves be substituted in their alkyl moieties by hydroxy, amino, carboxy or protected carboxy groups. Examples of hydroxyalkyl-substituted amino groups include the hydroxymethylamino, 2-hydroxyethylamino, 3-hydroxypropylamino and 4-hydroxybutylamino groups. Examples of aminoalkyl-substituted amino groups include the 2-aminoethylamino, 3-aminopropylamino and 4-aminobutylamino groups. Examples of carboxyalkyl-substituted amino groups include the carboxymethylamino, 2-carboxyethylamino, 3-carboxypropylamino and 4-carboxybutylamino groups. Examples of protected carboxyalkyl-substituted amino groups include the groups where the protecting group is a lower alkoxy group (for example the methoxycarbonylmethylamino, ethoxycarbonylmethylamino, propoxycarbonylmethylamino, 2-ethoxycarbonylethylamino and 3-ethoxycarbonylpropylamino groups) and the groups in which the protecting group is an aralkyloxy group (for example the benzyloxycarbonylmethylamino, p-nitrobenzyloxycarbonylmethylamino, 2-p-nitrobenzyloxycarbonylethylamino and 3-p-nitrobenzyloxycarbonylpropylamino groups).

Where $R^7$ represents a cyclic amino group, this may contain one or more other hetero atoms in the heterocyclic ring (preferably oxygen and/or nitrogen atoms) and preferably has from 3 to 6 ring atoms; the cyclic amino group may be substituted or unsubstituted. Examples of such cyclic amino groups include the 1-aziridinyl, 1- pyrrolidinyl, piperidino, 4-hydroxypiperidino, 1-piperazinyl, 4-methyl-1-piperazinyl and morpholino groups.

Where $R^7$ represents an arylamino group, the aryl group is preferably a phenyl group and this may have one or more of the following substituents in its aromatic ring: lower alkyl groups (e.g. methyl, ethyl, propyl or isopropyl groups); lower alkoxy groups (e.g. methoxy, ethoxy or propoxy groups); and halogen atoms (e.g. fluorine, chlorine or bromine atoms).

Where $R^7$ represents an amino group having a heterocyclic substituent, it is preferably a 2-pyridylamino, 2-pyrimidylamino, 2-thiazolylamino, 2-isoxazolylamino or 1-methyl-5-tetrazolylamino group.

Where $R^7$ represents an aralkylamino group, it is preferably a benzylamino, phenethylamino or phenylpropylamino group and may have one or more of the following substituents in its aromatic ring: lower alkyl groups (e.g. methyl, ethyl, propyl or isopropyl groups); lower alkoxy groups (e.g. methoxy, ethoxy, propoxy or isopropoxy groups); and halogen atoms (e.g. fluorine, chlorine or bromine atoms).

Where $R^7$ represents an alkoxy group, this is preferably a lower alkoxy group and may be a straight or branched chain group. Examples of such alkoxy groups include the methoxy, ethoxy, propoxy and isopropoxy groups.

Where $R^7$ represents an aryloxy group, it is preferably a phenoxy group, which may have one or more of the following substituents in its aromatic ring: lower alkyl groups (e.g. methyl, ethyl, propyl or isopropyl groups); lower alkoxy groups (e.g. methoxy, ethoxy or propoxy groups); and halogen atoms (e.g. fluorine, chlorine or bromine atoms).

Where $R^7$ represents an aralkyloxy group, it is preferably a benzyloxy, phenethyloxy or phenylpropyloxy group and may have one or more of the following substituents in its aromatic ring: lower alkyl groups (e.g. methyl, ethyl, propyl or isopropyl groups); lower alkoxy groups (e.g. methoxy, ethoxy, propoxy or isopropoxy groups); nitro groups, and halogen atoms (e.g. fluorine, chlorine or bromine atoms).

Where $R^7$ represents a hydrazino group, it may have one or more alkyl, aralkyl or aryl substituents. Examples of suitable alkylhydrazino groups include the methylhydrazino, ethylhydrazino, propylhydrazino, isopropylhydrazino, N,N-dimethylhydrazino, N,N-diethylhydrazino, N,N-dipropylhydrazino or N,N-diisopropylhydrazino groups. In the case of the aralkylhydrazino groups, these are preferably benzylhydrazino, phenethylhydrazino or phenylpropylhydrazino groups and optionally have one or more of the following substituents in their aromatic ring: lower alkyl groups (e.g. methyl, ethyl, propyl or isopropyl groups); lower alkoxy groups (e.g. methoxy, ethoxy, propoxy or isopropoxy groups); and halogen atoms (e.g. fluorine, chlorine or bromine atoms). In the case of the arylhydrazino groups, these are preferably phenylhydrazino groups, which may have one or more of the following substituents in the aromatic ring: lower alkyl groups (e.g. methyl, ethyl, propyl or isopropyl groups); lower alkoxy groups (e.g. methoxy, ethoxy, propoxy or isopropoxy groups); or halogen atoms (e.g. fluorine, chlorine or bromine atoms).

Where $R^7$ represents an alkoxyamino group, the alkoxy group is preferably a lower alkoxy group and examples of such alkoxyamino groups include the methoxyamino, ethoxyamino, propoxyamino or isopropoxyamino groups.

$A'$ represents a bivalent saturated hydrocarbon group and may be an alkylene or alkylidine group, for example a methylene, ethylene, ethylidene, trimethylene, propylene or propylidene group.

Where $R^3$ represents a protected carboxy group, the protecting group is preferably one of the following: straight or branched chain lower alkyl groups (e.g. methyl, ethyl, propyl, isopropyl, butyl, isobutyl or t-butyl groups); halogenated lower alkyl groups (e.g. 2-iodoethyl, 2,2-dibromoethyl or 2,2,2-trichloroethyl groups); lower alkoxymethyl groups (e.g. methoxymethyl, ethoxymethyl, propoxymethyl, isopropoxymethyl, butoxymethyl or isobutoxymethyl groups); lower aliphatic acyloxymethyl groups (e.g. acetoxymethyl, propionyloxymethyl, butyryloxymethyl, isobutyryloxymethyl or pivaloyloxymethyl groups); 1-(lower alkoxy)carbonyloxyethyl groups (e.g. 1-methoxycarbonyloxyethyl, 1-ethoxycarbonyloxyethyl, 1-propoxycarbonyloxyethyl, 1-isopropoxycarbonyloxyethyl, 1-butoxycarbonyloxyethyl or 1-isobutoxycarbonyloxyethyl groups); aralkyl groups (e.g. benzyl, p-methoxybenzyl, o-nitrobenzyl or p-nitrobenzyl groups); the benzhydryl group; or the phthlidyl group.

Preferred compounds are those in which $R^1$ represents a hydrogen atom, an ethyl group, an ethyl group having a hydroxy, amino, $C_2$-$C_4$ aliphatic acyloxy or $C_2$-$C_4$ aliphatic acylamino substituent, preferably in its $\alpha$-position (e.g. a $\alpha$-hydroxyethyl, $\alpha$-acetoxyethyl, $\alpha$-propionyloxyethyl, $\alpha$-butyryloxyethyl, $\alpha$-aminoethyl, $\alpha$-acetylaminoethyl, $\alpha$-propionylaminoethyl or $\alpha$-butyrylaminoethyl group) or a methoxy group.

It is also preferred that $R^2$ should be a hydrogen atom or, where it is a group of formula

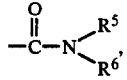

that $R^5$ and $R^6$ (which may be the same or different) should each represent a straight or branched chain lower alkyl group (e.g. a methyl, ethyl, propyl or isopropyl group), an aralkyl group (e.g. a benzyl group) or an aryl group (e.g. a phenyl group) or that $R^5$ and $R^6$, together with the nitrogen atom to which they are attached, should represent a 1-pyrrolidinyl, piperidino, 4-hydroxypiperidino, morpholino or 1-piperazinyl.

Alternatively, where $R^2$ represents a group of formula

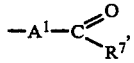

it is preferred that $R^7$ should represent a straight or branched chain $C_1$-$C_4$ alkyl group (methyl, ethyl, propyl, isopropyl, butyl, isobutyl, sec-butyl or t-butyl), an amino group, a lower alkyl-substituted amino group (e.g. methylamino, ethylamino, propylamino, isopropylamino, dimethylamino, diethylamino, dipropylamino or diisopropylamino), a lower hydroxyalkyl-substituted amino group (e.g. a hydroxyethylamino, hydroxypropylamino or hydroxybutylamino group), a lower aminoalkyl-substituted amino group (e.g. a 2-aminoethylamino, 3-aminopropylamino or 4-aminobutylamino group), a lower carboxyalkyl-substituted amino group (e.g. a carboxymethylamino, carboxyethylamino, 3-carboxypropylamino or 4-carboxybutylamino group), a lower alkoxycarbonylalkyl-substituted amino group (e.g. a methoxycarbonylmethylamino, 2-methoxycarbonylethylamino, ethoxycarbonylmethylamino or propoxycarbonylmethylamino group), a lower aralkyloxycarbonylalkyl-substituted amino group (e.g. a benzyloxycarbonylmethylamino, p-nitrobenzyloxycarbonylmethylamino, 2-p-nitrobenzyloxycarbonylethylamino or 3-p-nitrobenzyloxycarbonylpropylamino group), a cyclic amino group (e.g. a 1-aziridinyl, 1-pyrrolidinyl, piperidino, 4-hydroxypiperidino, morpholino or 1-piperazinyl group), an arylamino group (e.g. an anilino, p-toluidino, p-anisidino or p-chloroanilino group), a heterocyclic-substituted amino group (e.g. a 2-pyridylamino, 2-thiazolylamino or 1-methyl-5-tetrazolylamino group), a hydroxy group, a lower alkoxy group (e.g. a methoxy, ethoxy, propoxy or isopropoxy group), a hydrazino group, a lower alkyl-substituted hydrazino group (e.g. a methylhydrazino, ethylhydrazino, propylhydrazino or isopropylhydrazino group), a hydroxyamino group, a lower alkoxyamino group (e.g. a methoxyamino, ethoxyamino, propoxyamino or isopropoxyamino group) or a guanidino group and that A' should represent a straight or branched chain bivalent saturated aliphatic hydrocarbon group having from 1 to 3 carbon atoms, for example a methylene, ethylene, trimethylene, propylene, ethylidene or propylidene group.

It is also preferred that $R^3$ should represent a carboxy group or a pivaloyloxymethyloxycarbonyl group.

The most preferred compounds, having regard to their pharmaceutical activity and ease of preparation are those compounds in which:

$R^1$ represents a 1-hydroxyethyl group;
$R^2$ represents a group of formula

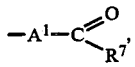

in which $R^7$ represents an amino group and A' represents a methylene group having a methyl or ethyl (particularly methyl) substituent; and
$R^3$ represents a carboxy group;
and sodium salts thereof.

The following list contains examples of compounds of the invention and these compounds are hereafter, where appropriate, identified by the numbers appended to them in this list.

1. 2-Thioxopenam-3-carboxylic acid.
2. p-Nitrobenzyl 2-thioxopenam-3-carboxylate.
3. 2-(N,N-Diethylcarbamoylthio)penem-3-carboxylic acid.
4. 2-(1-Pyrrolidinylcarbonylthio)penem-3-carboxylic acid.
5. p-Nitrobenzyl 2-(1-pyrrolidinylcarbonylthio)penem-3-carboxylate.
6. 2-(4-Hydroxypiperidinocarbonylthio)penem-3-carboxylic acid.
7. 2-Morpholinocarbonylthiopenem-3-carboxylic acid.
8. 2-(1-Piperazinylcarbonylthio)penem-3-carboxylic acid.
9. 2-(N-Methyl-N-phenylcarbamoylthio)penem-3-carboxylic acid.
10. 2-(N-Benzyl-N-methylcarbamoylthio)penem-3-carboxylic acid.
11. p-Nitrobenzyl 6-(1-t-butyldimethylsilyloxyethyl)-2-thioxopenam-3-carboxylate.
12. p-Nitrobenzyl 6-(1-hydroxyethyl)-2-thioxopenam-3-carboxylate.
13. 6-(1-Hydroxyethyl)-2-thioxopenam-3-carboxylic acid.
14. 6-Methoxy-2-thioxopenam-3-carboxylic acid.
15. 6-Ethyl-2-thioxopenam-3-carboxylic acid.
16. p-Nitrobenzyl 6-(1-acetoxyethyl)-2-thioxopenam-3-carboxylate.
17. p-Nitrobenzyl 6-(1-p-nitrobenzyloxycarbonyloxyethyl)-2-thioxopenam-3-carboxylate.
18. 2-(2-Oxopropylthio)penem-3-carboxylic acid.
19. 2-(3,3,3-Trifluoro-2-oxopropylthio)penem-3-carboxylic acid.
20. Sodium 2-(3,3,3-trifluoro-2-oxopropylthio)penem-3-carboxylate hydrate.
21. Methyl 2-(3,3,3-trifluoro-2-oxopropylthio)penem-3-carboxylate.
22. Methyl 2-(2-oxoethylthio)penem-3-carboxylate.
23. p-Nitrobenzyl 2-(2-oxo-2-phenylethylthio)penem-3-carboxylate.
24. 2-(2-Oxopentylthio)penem-3-carboxylic acid.
25. 2-(2-Oxo-4-phenylbutylthio)penem-3-carboxylic acid.
26. 2-(3-Oxobutylthio)penem-3-carboxylic acid.
27. 2-(1-Methyl-2-oxopropylthio)penem-3-carboxylic acid.
28. 2-(5-Bromo-3-oxopentylthio)penem-3-carboxylic acid.
29. 2-[2-(p-Bromophenyl)-2-oxoethylthio]penem-3-carboxylic acid.
30. 2-Carbamoylmethylthiopenem-3-carboxylic acid.
31. 2-(2-Carbamoylethylthio)penem-3-carboxylic acid.
32. 2-(N-Methylcarbamoylmethylthio)penem-3-carboxylic acid.
33. 2-(N,N-Diethylcarbamoylmethylthio)penem-3-carboxylic acid.
34. 2-(N-Isopropylcarbamoylmethylthio)penem-3-carboxylic acid.
35. 2-(3-Oxo-3-piperidinopropylthio)penem-3-carboxylic acid.
36. 2-[2-Oxo-2-(1-piperazinyl)ethylthio]penem-3-carboxylic acid.
37. p-Nitrobenzyl 2-[2-(4-p-nitrobenzyloxycarbonyl-1-piperazinyl)-2-oxoethylthio]penem-3-carboxylate.
38. 2-(2-Morpholino-2-oxoethylthio)penem-3-carboxylic acid.
39. 2-(1-Carbamoylethylthio)penem-3-carboxylic acid.
40. 2-(1-N-Methylcarbamoylethylthio)penem-3-carboxylic acid.
41. 2-[2-(N-p-Tolylcarbamoyl)ethylthio]penem-3-carboxylic acid.
42. 2-(2-N-Benzylcarbamoylethylthio)penem-3-carboxylic acid.
43. 2-Carboxymethylthiopenem-3-carboxylic acid.
44. 2-Ethoxycarbonylmethylthiopenem-3-carboxylic acid.
45. p-Nitrobenzyl 2-(p-nitrobenzyloxycarbonylmethylthio)penem-3-carboxylate.
46. 2-Hydrazinocarbonylmethylthiopenem-3-carboxylic acid.
47. 2-(2-N,N-Dimethylhydrazinocarbonylethylthio)penem-3-carboxylic acid.
48. 2-(N-Hydroxycarbamoylmethylthio)penem-3-carboxylic acid.
49. 2-(N-Methoxycarbamoylmethylthio)penem-3-carboxylic acid.

50. 2-(N-Carboxymethylcarbamoylmethylthio)-3-carboxylic acid.
51. 2-(2-Oxopropylthio)-6-(1-hydroxyethyl)penem-3-carboxylic acid.
52. 2-(2-Carbamoylmethylthio)-6-methoxypenem-3-carboxylic acid.
53. 2-Carbamoylmethylthio-6-(1-hydroxyethyl)penem-3-carboxylic acid.
54. 6-(1-Hydroxyethyl)-2-(N-methylcarbamoylmethylthio)penem-3-carboxylic acid.
55. 6-(1-Aminoethyl)-2-carbamoylmethylthiopenem-3-carboxylic acid.
56. 2-Carbamoylmethylthio-6-ethylpenem-3-carboxylic acid.
57. 6-(1-Acetoxyethyl)-2-carbamoylmethylthiopenem-3-carboxylic acid.
58. p-Nitrobenzyl 6-(1-t-butyldimethylsilyloxyethyl)-2-carbamoylmethylthiopenem-3-carboxylate.
59. p-Nitrobenzyl 2-carbamoylmethylthio-6-(1-p-nitrobenzyloxycarbonyloxyethyl)penem-3-carboxylate.
60. Pivaloyloxymethyl 2-carbamoylmethylthio-6-(1-hydroxyethyl)penem-3-carboxylate.
61. 6-(1-Hydroxyethyl)-2-methoxycarbonylmethylthiopenem-3-carboxylic acid.
62. 6-Methoxy-2-(2-N-methylcarbamoylmethylthio)penem-3-carboxylic acid.
63. 6-Hydroxymethyl-2-(2-N-methylcarbamoylmethylthio)penem-3-carboxylic acid.
64. 2-Carboxymethylthio-6-(1-hydroxyethyl)penem-3-carboxylic acid.
65. 2-(1-Carbamoylethylthio)-6-(1-hydroxyethyl)-penem-3-carboxylic acid.
66. 2-Hydrazinocarbonylmethylthio-6-(1-hydroxyethyl)penem-3-carboxylic acid.
67. 2-(N-Hydroxycarbamoylmethylthio)-6-(1-hydroxyethyl)penem-3-carboxylic acid.
68. 6-(1-Hydroxyethyl)-2-(N-methoxycarbamoylmethylthio)penem-3-carboxylic acid.
69. 2-(N-Carboxymethylcarbamoylmethylthio)-6-(1-hydroxyethyl)penem-3-carboxylic acid.
70. 2-(2-Carbamoylethylthio)-6-(1-hydroxyethyl)-penem-3-carboxylic acid.
71. 2-(1-Carbamoylethylthio)-6-hydroxymethylpenem-3-carboxylic acid.
72. 2-(1-Carbamoylethylthio)-6-ethylpenem-3-carboxylic acid.
73. p-Nitrobenzyl 6-(1-t-butyldimethylsilyloxyethyl)-2-(1-carbamoylethylthio)penem-3-carboxylate.
74. 2-(1-Carbamoylpropylthio)-6-(1-hydroxyethyl)-penem-3-carboxylic acid.
75. p-Nitrobenzyl 6-(1-t-butyldimethylsilyloxyethyl)-2-(1-carbamoylpropylthio)penem-3-carboxylate.
76. p-Nitrobenzyl 2-(1-carbamoylpropylthio)-6-(1-hydroxyethyl)penem-3-carboxylate.
77. p-Nitrobenzyl 2-(1-carbamoylethylthio)-6-(1-hydroxyethyl)penem-3-carboxylate.
78. p-Nitrobenzyl 2-(3,3,3-trifluoro-2-oxopropylthio)-penem-3-carboxylate.
79. p-Nitrobenzyl 2-(2-oxopropylthio)penem-3-carboxylate.
80. p-Nitrobenzyl 2-carbamoylmethylthiopenem-3-carboxylate.
81. p-Nitrobenzyl 2-(N-methylcarbamoylmethylthio)-penem-3-carboxylate.
82. p-Nitrobenzyl 2-(1-carbamoylethylthio)penem-3-carboxylate.
83. p-Nitrobenzyl 2-(1-N-methylcarbamoylethylthio)-penem-3-carboxylate.
84. p-Nitrobenzyl 2-(N,N-diethylcarbamoylmethylthio)penem-3-carboxylate.
85. p-Nitrobenzyl 2-[N-(2-hydroxyethyl)carbamoylmethylthio]penem-3-carboxylate.
86. p-Nitrobenzyl 2-(N-p-nitrobenzyloxycarbonylmethylcarbamoylmethylthio)penem-3-carboxylate.
87. p-Nitrobenzyl 2-(2-morpholino-2-oxoethylthio)-penem-3-carboxylate.
88. p-Nitrobenzyl 2-hydrazinocarbonylmethylthiopenem-3-carboxylate.
89. p-Nitrobenzyl 2-(N-hydroxycarbamoylmethylthio)-penem-3-carboxylate.
90. p-Nitrobenzyl 2-(N-methoxycarbamoylmethylthio)-penem-3-carboxylate.
91. p-Nitrobenzyl 2-(2-carbamoylethylthio)penem-3-carboxylate.
92. p-Nitrobenzyl 2-(p-nitrobenzyloxycarbonylmethylthio)penem-3-carboxylate.
93. p-Nitrobenzyl 6-(1-t-butyldimethylsilyloxyethyl)-2-(N-methylcarbamoylmethylthio)penem-3-carboxylate.
94. p-Nitrobenzyl 6-(1-hydroxyethyl)-2-(N-methylcarbamoylmethylthio)penem-3-carboxylate.
95. p-Nitrobenzyl 6-(1-t-butyldimethylsilyloxyethyl)-2-methoxycarbonylmethylthiopenem-3-carboxylate.
96. p-Nitrobenzyl 2-carbamoylmethylthio-6-(1-hydroxyethyl)penem-3-carboxylate.
97. p-Nitrobenzyl 6-methoxy-2-(2-oxopropylthio)-penem-3-carboxylate.
98. p-Nitrobenzyl 6-(1-hydroxyethyl)-2-methoxycarbonylmethylthiopenem-3-carboxylate.
99. p-Nitrobenzyl 2-(N-methylcarbamoylmethylthio)-6-methoxypenem-3-carboxylate.

Of these compounds, Compounds No. 53, 65 and 74 are particularly preferred, Compound No. 65 being the most preferred.

The compounds of the invention can exist in various stereoisomeric forms and, although all of the isomers are indicated by a single formula in the above description, both the individual isomers and mixtures of two or more isomers are included. We particularly prefer those compounds which have the (5R,6S) or (5R,6R) configuration and, where $R^1$ represents an α-substituted alkyl group (e.g. an α-hydroxyalkyl, α-acetoxyalkyl, α-aminoalkyl or α-acetamidoalkyl group), it is preferred that this α-substituent should be in the R- configuration.

Those compounds of the invention where $R^3$ represents a carboxy group and/or where $R^2$ includes a carboxy group can form salts, in the same way as conventional carboxylic acids. The nature of the salt-forming cation is not critical although, as is well-recognized in the art, the cation should not render the resulting salt pharmaceutically unacceptable. Suitable salts include those with metals (such as the lithium, sodium, potassium, calcium or magnesium salts), the ammonium salts and the organic amine salts (for example the cyclohexylammonium, diisopropylammonium and triethylammonium salts). Of these, the sodium and potassium salts are particularly preferred.

The compounds of the invention can be prepared by the following methods.

METHOD A

Compounds in which $R^2$ represents a hydrogen atom can be prepared as shown in the following reaction scheme:

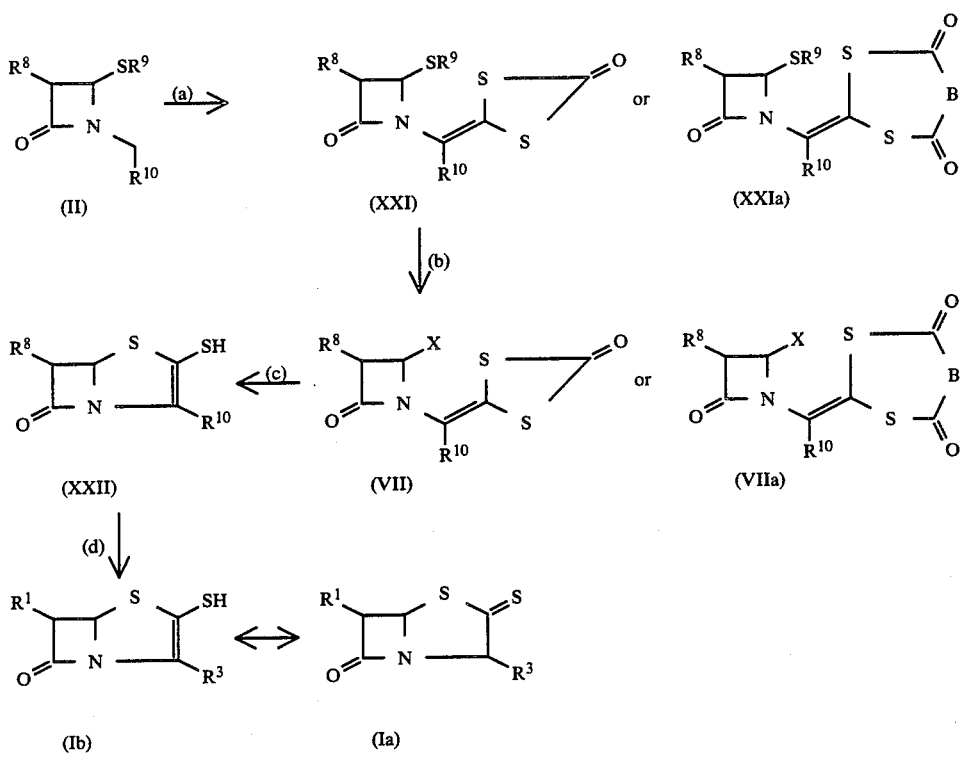

(in which $R^1$, $R^3$, $R^8$, $R^9$, $R^{10}$ and X are as defined above).

Step (a)

The first step of Method A comprises reacting the azetidinone (II) with carbon disulphide in the presence of a base and then reacting the resulting compound with a compound of formula (III):

$$X-\overset{O}{\underset{\|}{C}}-X \qquad (III)$$

(in which X represents a halogen atom).

The whole of the reaction is preferably carried out in the presence of a solvent; there is no particular limitation on the nature of the solvent employed, provided that it has no adverse effect on the reaction. Preferred solvents include ethers (such as tetrahydrofuran or diethyl ether), fatty acid dialkylamides (such as dimethylformamide or dimethylacetamide) and mixtures of these organic solvents. The base employed in the first part of this reaction is preferably lithium diisopropylamide or lithium hexamethyldisilazane. The reaction temperature is not critical, although the reaction is preferably carried out at a relatively low temperature, e.g. from −78° C. to −20° C., to control side reactions. In some cases it may also be desirable to carry out the reaction under an atmosphere of inert gas, such as nitrogen. The time required for the reaction with the base is generally from 5 minutes to 1 hour, the time required for the reaction with carbon disulphide is generally from 10 minutes to 2 hours and the time required for the reaction with the carbonyl halide (III) is generally from 10 minutes to 5 hours.

After completion of the reaction, the desired product of formula (XXI) may be recovered from the reaction mixture by conventional means. A suitable recovery procedure comprises: adding glacial acetic acid to the reaction mixture to terminate the reaction; adding a water-immiscible organic solvent and water; separating the organic phase; washing the organic phase successively, e.g. with aqueous sodium bicarbonate and water; drying the organic phase; and then distilling off the organic solvent to give the desired product. If desired, the resulting product can be further purified by conventional means, such as recrystallization, preparative thin layer chromatography or column chromatography.

Alternatively, instead of employing the carbonyl halide (III), it is possible to use a dicarboxylic acid dihalide to prepare a compound of formula (XXIa): (in which $R^8$, $R^9$ and $R^{10}$ are as defined above and B represents the residue of the dicarboxylic acid dihalide, XCO—B—COX, where X represents a halogen atom).

Preferred dicarboxylic acid dihalides are the dimethylmalonyl and phthaloyl dihalides, especially the dichlorides. The reaction conditions and subsequent recovery procedure are the same as when a carbonyl halide (III) is employed.

Step (b)

In this step, the compound of formula (XXI) or (XXIa) is reacted with a halogenating agent to give the compound of formula (VII) or (VIIa).

The halogenation reaction is preferably carried out in the presence of a solvent, although the nature of the solvent is not particularly critical, provided that it has no adverse effect upon the reaction. Preferred solvents include methylene chloride, chloroform, carbon tetrachloride and 1,2-dichloroethane. The nature of the halogenating agent is not particularly critical, provided that it does not attack other parts of the molecule. Suitable halogenating agents include chlorine, bromine, sulphuryl chloride and sulphuryl bromide. The reaction temperature is not critical, although, in order to control side reactions, relatively low temperatures are preferred and, for this reason, we prefer to conduct the reaction at a temperature from −20° C. to about room temperature. The time required for the reaction will vary depending upon the nature of the starting materials and upon the reaction temperature, but the reaction will generally be complete within from 1 minute to 1 hour.

After completion of the reaction, the compound of formula (VII) or (VIIa) may be recovered from the reaction mixture by conventional means, e.g. simply by distillation of the solvent and of any excess reagents. In general, the product may be used as a starting material for the next step without any purification.

If desired, the halogen represented by X in the compound of formula (VII) or (VIIa) thus obtained may be converted to any other halogen atom by known methods. For example, the chlorine compound may be converted to the corresponding bromine or iodine compound by treating the chloride compound with an inorganic bromide or iodide (e.g. lithium bromide or potassium iodide) in an organic solvent (e.g. diethyl ether or acetone).

Step (c)

In this step, the compound of formula (VII) or (VIIa) is treated with a base to cause ring closure and thereby afford the compound of formula (XXII). The ring closure reaction is preferably carried out in the presence of a solvent, although the nature of the solvent is not particularly critical, provided that it has no adverse effect upon the reaction. Suitable solvents include: halogenated hydrocarbons, such as methylene chloride, chloroform, carbon tetrachloride and 1,2-dichloroethane; alcohols, such as methanol, ethanol and propanol; ethers, such as diethyl ether, dioxan and tetrahydrofuran; aromatic hydrocarbons, such as benzene, toluene and xylene; ketones, such as acetone and methyl ethyl ketone; fatty acid dialkylamides, such as dimethylformamide and dimethylacetamide; esters, such as methyl acetate and ethyl acetate; and mixtures of one or more of these organic solvents with water.

A wide variety of bases may be employed to facilitate the ring closure reaction and any base capable of reacting to the thiocarbonyl bond as a nucleophilic agent to eliminate the bond may be employed. Preferred organic bases include: aliphatic primary amines, e.g. methylamine, ethylamine, propylamine and butylamine; arylamines, e.g. aniline and p-chloroaniline; aralkylamines, e.g. benzylamine and phenethylamine; alkali metal alkoxides in alcohols, e.g. sodium methoxide/methanol, sodium ethoxide/ethanol and potassium t-butoxide/t-butanol. Preferred inorganic bases include ammonia, sodium bicarbonate, sodium carbonate, potassium carbonate, potassium hydroxide and sodium hydroxide.

The reaction temperature is not critical and the reaction is preferably carried out at a temperature from −20° C. to about room temperature. The time required for the reaction will depend upon the nature of the starting materials and on the reaction temperature, but the reaction will normally be complete within a period of from 30 minutes to 12 hours.

After completion of the reaction, the desired product of formula (XXII) may be recovered from the reaction mixture by conventional means, depending upon the nature of the product and of the reaction medium in which it has been formed. One suitable recovery process comprises: distilling off the reaction solvent under reduced pressure; diluting the reaction mixture with a water-immiscible organic solvent; washing the mixture with water; and distilling off the solvent to give the desired product.

The compound (XXII) thus obtained may, if necessary, be further purified by conventional means, for example by recrystallization, preparative thin layer chromatography or column chromatography.

Step (d)

If necessary, the compound of formula (XXII) may be converted to the corresponding free carboxylic acid by conversion of the protected carboxy group $R^{10}$ to a free carboxy group by conventional means. The reaction required to remove the protecting group will vary depending upon the nature of the protecting group, but any method known in the art may be used.

For example, where the protecting group is a halogenated alkyl group, an aralkyl group or a benzhydryl group, it may be removed by contacting the compound of formula (XXII) with a reducing agent. In the case of halogenated alkyl groups (e.g. 2,2-dibromoethyl or 2,2,2-trichloroethyl), a preferred reducing agent is a combination of zinc with acetic acid. In the case of aralkyl groups (e.g. benzyl or p-nitrobenzyl) or the benzhydryl group, a preferred reducing agent is a catalytic reducing agent (e.g. palladium on charcoal) in the presence of hydrogen, or an alkali metal sulphide (e.g. sodium sulphide or potassium sulphide). The reaction will normally be carried out in the presence of a solvent, the nature of which is not critical, provided that it has no adverse effect upon the reaction. Preferred solvents are alcohols (such as methanol or ethanol), ethers (such as tetrahydrofuran or dioxan), fatty acids (such as acetic acid) or a mixture of one or more of these organic solvents with water. The reaction temperature will normally be from 0° C. to about room temperature. The time required for the reaction will vary depending upon the reagents and the reaction temperature, but the reaction is normally complete within from 5 minutes to 12 hours.

After completion of the reaction, the product may be recovered from the reactive mixture by conventional means, e.g. by filtering off insolubles, washing the organic solution with water and drying it and then distilling off the solvent. If necessary, the product may be further purified by such conventional means as recrystallization, preparative thin layer chromatography or column chromatography.

Where the group represented by $R^8$ in the compound of formula (XXII) includes a protected hydroxy, protected mercapto or protected amino group, the protecting group may, if necessary, be removed by conventional means to restore the free hydroxy, mercapto or amino group. The restored hydroxy group may then, if desired, be converted to an acyloxy group, a halogen atom, an azido group, an amino group, an acylamino group or an alkylthio group. These reactions may take place before, after or together with the removal of the carboxy-protecting group in $R^{10}$.

Compounds of formula (Ib) in which $R^1$ represents a group of formula $R^4A-$ and $R^4$ represents a hydroxy group may be prepared by removing the hydroxy-protecting group (e.g. acyl group or trialkylsilyl group) in the compound of formula (XXII). Where the protected hydroxy group is a lower aliphatic acyloxy group (e.g. an acetoxy group), the protecting group may be removed by treating the corresponding compound with a base in the presence of an aqueous solvent. There is no particular limitation on the solvent, and any solvent commonly used in hydrolysis may be employed. However, we particularly prefer water or a mixture of water with an organic solvent, such as an alcohol (e.g. methanol, ethanol or propanol) or an ether (e.g. tetrahydrofuran or dioxan). The base employed is also not particularly critical, provided that it does not affect other parts of the compound, particularly the β-lactam ring. Preferred bases are alkali metal carbonates, such as sodium carbonate or potassium carbonate. The reaction temperature is not critical, but we prefer a temperature of from 0° C. to about room temperature, in order to control side reactions. The time required for the reaction will vary depending upon the nature of the starting materials and upon the reaction temperature, but the reaction will normally be complete within a period of from 1 to 6 hours.

Where the protected hydroxy group is an aralkyloxycarbonyloxy group (e.g. a benzyloxycarbonyloxy group or p-nitrobenzyloxycarbonyloxy group), the protecting group may be removed by contacting the corresponding compound with a reducing agent. The reducing agents and reaction conditions which may be employed are the same as those which may be employed for the removal of aralkyl groups from the protected carboxy group $R^{10}$. Accordingly, by choosing appropriate protecting groups, it is possible simultaneously to remove protecting groups from $R^8$ and $R^{10}$.

Where the protected hydroxy group is a tri(lower alkyl)silyloxy group (e.g. t-butyldimethylsilyloxy), the protecting group may be removed by treating the corresponding compound with tetrabutylammonium fluoride in a suitable solvent, the nature of which is not critical, provided it has no adverse effect upon the reaction. Suitable solvents are ethers, such as tetrahydrofuran or dioxan. The reaction is preferably carried out at about room temperature and will normally require from 10 to 18 hours.

Where the group $R^8$ includes a protected mercapto group (e.g. an acylthio group), this may be converted to a mercapto group by removal of the acyl protecting group. Preferred acylthio groups are lower aliphatic acylthio groups (e.g. acetylthio) and, in this case, the acyl group may be removed by treating the corresponding compound with a base in the presence of an aqueous solvent. The reagents and reaction conditions are the same as those used for removing acyl groups, when an acyl group is used as a protecting group for a hydroxy group.

Compounds of formula (Ib) in which $R^4$ represents an azido group can be obtained by reacting the corresponding compound in which $R^4$ represents a hydroxy group with hydrogen azide or diphenylphosphoric azide in the presence of a phosphine derivative and of an azodicarboxylic acid dialkyl ester. Preferred phosphine derivatives include tributylphosphine and triphenylphosphine and preferred azodicarboxylic acid dialkyl esters include dimethyl azodicarboxylate and diethyl azodicarboxylate. Preferred solvents include: halogenated hydrocarbons, such as methylene chloride or chloroform, and ethers, such as tetrahydrofuran or dioxan. The reaction temperature is preferably from 0° C. to 50° C. and the time required for the reaction is generally from 10 minutes to 2 hours.

Compounds of formula (Ib) in which $R^4$ represents an amino group may be prepared by reducing the corresponding compounds in which $R^4$ represents an azido group. This reduction may be carried out by contacting the azido compound with a reducing agent in the presence of a solvent. The reducing agents which may be employed and the reaction conditions are similar to those described above for removing aralkyl groups which serve as carboxy-protecting groups in the group $R^{10}$. Alternatively, the reduction may be carried out at a temperature from 0° C. to about room temperature using ammonium sulphide or hydrogen sulphide/triethylamine as the reducing agent. Accordingly, it is possible to remove carboxy-protecting groups simultaneously, depending upon the type of reducing agent employed. Where the group represented by $R^8$ includes a protected amino group, i.e. $R^{12}$ represents an aralkyloxycarbonylamino group (e.g. a benzyloxycarbonylamino or p-nitrobenzyloxycarbonylamino group), the same reaction will remove the protecting group and convert the group $R^{12}$ to an amino group.

Compounds of formula (Ib) in which $R^4$ represents an acyloxy group or an acylamino group may be prepared by acylating the corresponding compound (Ib) in which $R^4$ represents a hydroxy group or an amino group, respectively. This reaction can be carried out by contacting the corresponding hydroxy or amino compound with an acylating agent in the presence of a solvent. There is no particular limitation on the nature of the solvent to be employed, provided that it has no adverse effect upon the reaction. Preferred solvents are: halogenated hydrocarbons, such as chloroform or methylene chloride; and ethers, such as tetrahydrofuran or dioxan. There is no particular limitation upon the nature of the acylating agent to be employed and any acylating agent commonly used for the acylation of hydroxy or amino groups may be used. Preferred acylating agents include: fatty acid anhydrides, such as acetic anhydride or propionic anhydride; and fatty acid halides, such as acetyl chloride, propionyl chloride, butyryl bromide, isobutyryl bromide or methoxalyl chloride. The reaction is preferably carried out in the presence of a base, for example an organic base (e.g. triethylamine or pyridine) or an alkali metal salt of a fatty acid (e.g. sodium acetate or potassium acetate). The reaction temperature is not critical, but we prefer to carry out the reaction at a temperature of from 0° C. to about room temperature. The time required for the reaction will vary, depending upon the nature of the acylating agent and the reaction temperature, but it will usually be from 0.5 to 5 hours.

A compound of formula (Ib) in which $R^4$ represents an alkylthio group may be prepared by halogenating the corresponding compound (Ib) in which $R^4$ represents a hydroxy group and then reacting the halogenated compound with an alkali metal salt of an alkylmercaptan, preferably the sodium or potassium salt. Suitable solvents for this reaction include alcohols, such as methanol, ethanol or isopropanol. The reaction is normally carried out at about room temperature and will require a period of from 30 minutes to 5 hours.

METHOD B

Compounds of formula (Ib), tautomeric with compounds of formula (Ia), may also be prepared by the following reaction scheme:

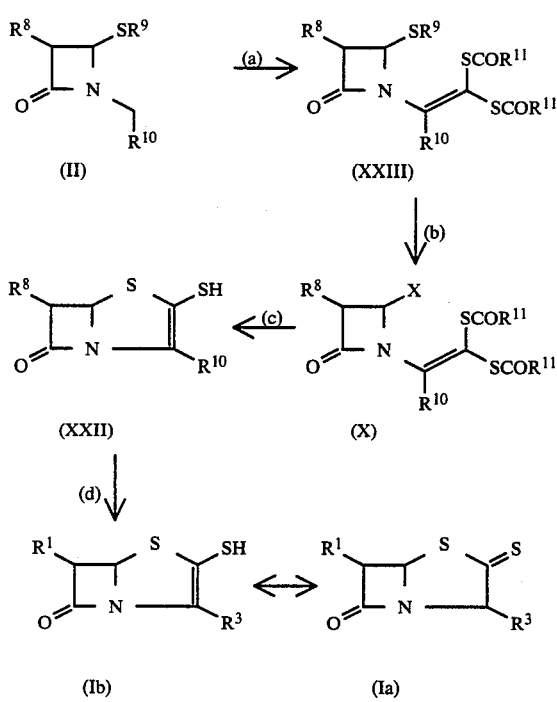

(in which $R^1$, $R^3$, $R^8$, $R^9$, $R^{10}$, $R^{11}$ and X are as defined above).

Step (a)

The first step in Method B comprises reacting the azetidinone (II) with carbon disulphide in the presence of a base and reacting the resulting compound with a compound of formula (VI):

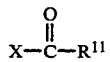     (VI)

(in which X represents a halogen atom and $R^{11}$ is as defined above).

The reactions in this step may be carried out by contacting the azetidinone (II) with the base in the presence of a solvent, reacting the compound with carbon disulphide and finally reacting the resulting product with the acyl chloride (VI). The solvents and bases which can be employed in this reaction, the reaction temperature, the time required for the reaction and the method of recovering the product are all similar to those described in relation to the corresponding reactions in step (a) of Method A.

Step (b)

This reaction comprises contacting the compound of formula (XXIII) prepared in step (a) with a halogenating agent. Solvents, reagents and reaction conditions are all similar to those described in step (b) of Method A.

Step (c)

In this step, the compound of formula (X) prepared in step (b) is treated with a base to effect ring closure. Reagents and reaction conditions are similar to those described in step (c) of Method A.

Step (d)

In this step, if necessary, protecting groups are removed and, if desired, the hydroxy group represented by $R^4$ in the product of formula (Ib) is converted to an azido group, an amino group, an acyloxy group, an acylamino group or an alkylthio group. Reagents and reaction conditions are as described in step (d) of Method A.

Method C

Compounds of formula (Ic), that is to say compounds of formula (I) in which $R^2$ represents a substituted carbamoyl group, can be prepared by the following reaction reaction scheme:

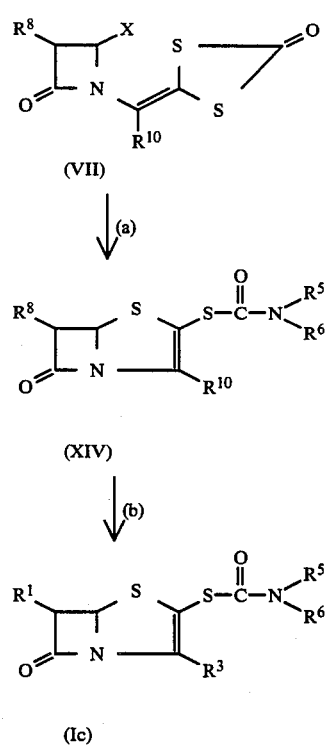

(in which $R^1$, $R^3$, $R^5$, $R^6$, $R^8$, $R^{10}$, X and B are as defined above).

Step (a)

The first step in this reaction comprises reacting the compound of formula (VII), which can be prepared as described in steps (a) and (b) of Method A, with a secondary amine of formula (XIII):

    (XIII)

(in which $R^5$ and $R^6$ are as defined above) in the presence of a base to give the compound of formula (XIV). Solvents, bases, reaction conditions and method of recovery of the desired product are similar to those described in step (a) of Method A.

Step (b)

In this step, protecting groups are, if necessary, removed and the hydroxy group represented by $R^4$ in the group represented by $R^1$ may be converted to an azido group, an amino group, an acyloxy group, an acylamino group or an alkylthio group, as described in step (d) of Method A. Where the group $R^5$ and/or $R^6$ contains a nitrogen atom (e.g. the nitrogen atom at the 4-position of a piperazinyl group represented by $R^5$ and $R^6$ together with the nitrogen atom to which they are attached), this is preferably protected, e.g. by an acyl group or an aralkyloxycarbonyl group during the reaction of step (a). This protecting group may be removed as described in step (d) of Method A for the removal of acyl groups from protected amino groups in the group represented by $R^8$.

METHOD D

Compounds of formula (Id), that is to say compounds of formula (I) in which $R^2$ represents a group of formula

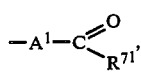

may be prepared as illustrated by the following reaction scheme.

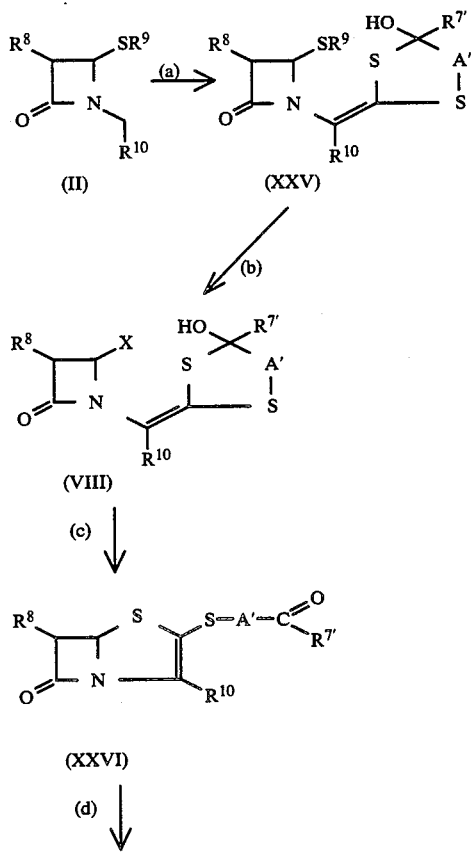

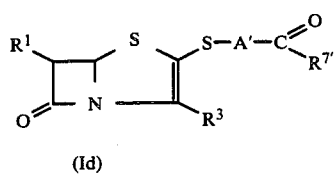

(Id)

(in which $R^1$, $R^3$, $R^{7'}$, $R^8$, $R^9$, $R^{10}$, A' and X are as defined above).

Step (a)

The first step of this reaction comprises reacting the azetidinone (II) with carbon disulphide in the presence of a base and then reacting the resulting compound with a halogenated ketone of formula (IV):

(in which X represents a halogen atom, preferably a chlorine or bromine atom, and $R^{7'}$ and A' are as defined above).

The reaction conditions, solvents, bases and recovery techniques are as described in step (a) of Method A.

Steps (b)–(d)

These steps consist, respectively, of the halogenation of the compound of formula (XXV) prepared in step (a) to give a compound of formula (VIII), the ring closure of this compound of formula (VIII) to give a compound of formula (XXVI) and finally, if necessary, removal of protecting groups and conversion of a hydroxy group represented by $R^4$ in the group represented by $R^1$ to an acyloxy group, a halogen atom, an azido group, an amino group, an acylamino group or an alkylthio group. The reaction conditions employed for all of these steps are similar to those employed for the corresponding step in Method A.

METHOD E

Compounds of formula (I) in which $R^2$ represents a group of formula

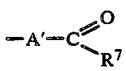

and $R^7$ represents an amino group, that is to say compounds of formula (Ie), or $R^7$ represents a hydroxy, alkoxy, aryloxy or aralkyloxy group, that is to say compounds of formula (If), can be prepared as demonstrated by the following reaction scheme:

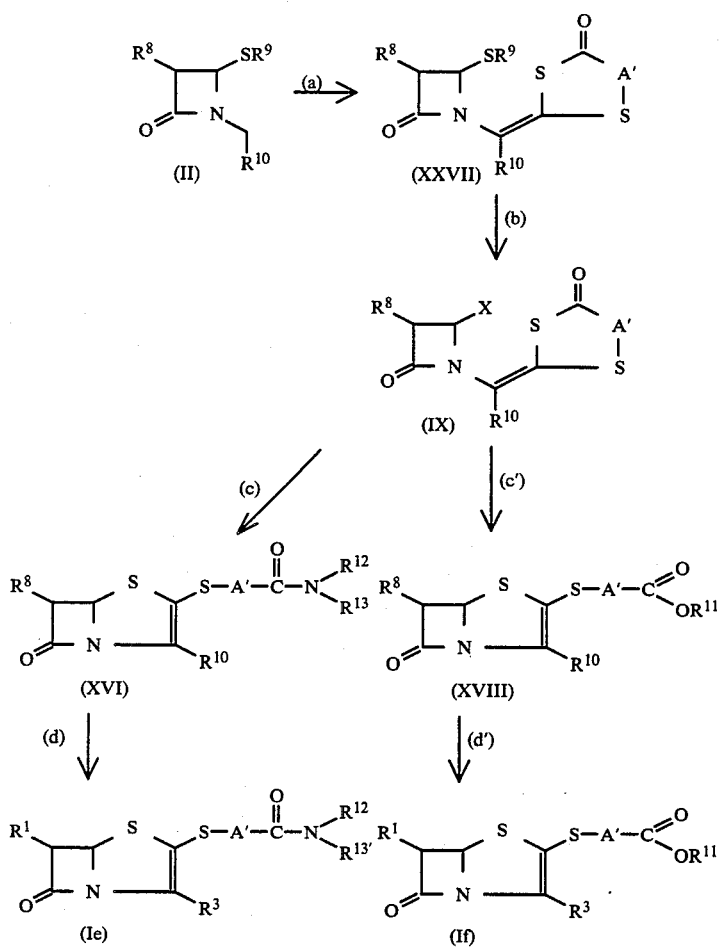

In the above formulae, $R^1$, $R^3$, $R^8$, $R^9$, $R^{10}$, $R^{11}$, $R^{12}$, $R^{13}$ and $A'$ are as defined above and $R^{13'}$ represents any of the groups represented by $R^{13}$ and any of those groups in which protecting groups have been removed.

Step (a)

In this step, the 4-alkylthio-2-azetidinone derivative of formula (II) is reacted with carbon disulphide in the presence of a base (the reagents and reaction conditions being the same as described for the corresponding step of Method A) and then the product is reacted with a compound of formula (V):

$$\overset{O}{\underset{\|}{X-A'-C-Z}} \quad (V)$$

in which: Z represents a halogen atom (for example a chlorine or bromine atom) or a lower alkoxycarbonyloxy group (for example a methoxycarbonyloxy, ethoxycarbonyloxy or sec-butoxycarbonyloxy group); X represents a halogen atom (for example a chlorine or bromine atom); and $A'$ is as defined above.

The reaction conditions, solvents etc employed in the reaction with the compound of formula (V) are similar to those employed in the corresponding reaction with the carbonyl halide in step (a) of Method A.

Step (b)

This step involves the halogenation of the compound of formula (XXVII) obtained in step (a) to give the corresponding halo-derivative of formula (IX). The halogenating agents and solvents which can be employed, as well as reaction temperatures, time required for the reaction and method of recovery of the product are the same as those described in step (b) of Method A.

Steps (c) and (c')

In this step a compound of formula (XVI) or (XVIII) is obtained by reacting the compound of formula (IX) prepared in step (b) with a compound of formula (XV):

$$HN\underset{R^{13}}{\overset{R^{12}}{\diagdown}} \quad (XV)$$

(in which $R^{12}$ and $R^{13}$ are as defined above) or with a compound of formula (XVII):

$$HO-R^{11} \quad (XVII)$$

(in which $R^{11}$ is as defined above). This reaction is carried out in the presence of a base. The reagents, solvents, reaction conditions and method of recovery of the product are similar to those described in relation to step (c) of Method A.

Steps (d) and (d')

Finally, if desired, protecting groups may be removed from the compounds of formula (XVI) and (XVIII), to give the desired compounds of formula (Ie) and (If). Reagents, reaction conditions and methods for recovering the final products are as described in relation to step (d) of Method A.

METHOD F

Compounds of formula (I) in which $R^2$ represents a group of formula

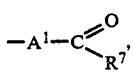

that is to say compounds of formula (Ig), can be prepared as illustrated by the following reaction scheme:

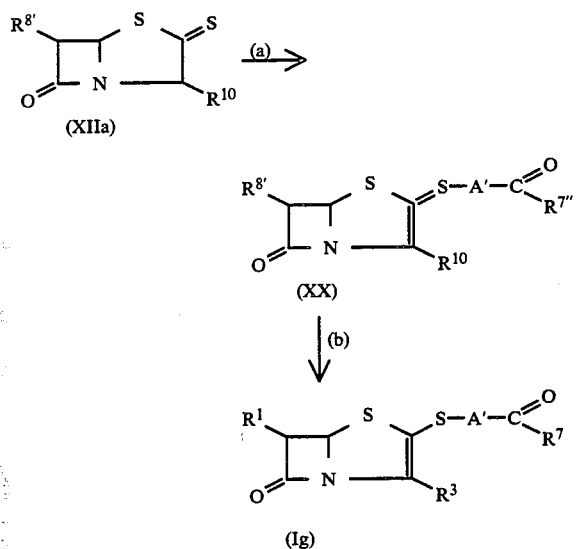

In the above formulae, $R^1$, $R^3$, $R^7$, $R^{7''}$, $R^{8'}$, $R^{10}$ and $A'$ are as defined above.

Step (a)

In this step, the compound of formula (XIIa), which can have been prepared as described in step (c) of Method A, optionally after having removed protecting groups from the group $R^8$, is reacted with an alkylating agent of formula (XIX):

in which $R^{7''}$ and $A'$ are as defined above and Y represents a halogen atom (particularly a chlorine, bromine or iodine atom), an alkylsulphonyloxy group (particularly a methanesulphonyloxy or ethanesulphonyloxy group) or an arylsulphonyloxy group (particularly a benzenesulphonyloxy or p-toluenesulphonyloxy group).

The reaction preferably takes place in the presence of a base and of a solvent. There is no particular limitation on the nature of the solvent, provided that it does not adversely affect the reaction and preferred solvents include: halogenated hydrocarbons, such as chloroform, methylene chloride or ethylene dichloride; ketones, such as acetone or methyl ethyl ketone; ethers, such as diethyl ether, tetrahydrofuran or dioxan; aromatic hydrocarbons, such as benzene or toluene; nitriles, such as acetonitrile; esters, such as ethyl formate or ethyl acetate; alcohols, such as methanol or ethanol; amides, such as dimethylformamide or dimethylacetamide; dimethyl sulphoxide, nitromethane; or a mixture of any two or more of these solvents or a mixture of one or more of these solvents with water. There is also no particular limitation on the nature of the base employed in this reaction, provided that it has no harmful effect on other parts of the molecule, especially the β-lactam ring. Preferred bases are acid-binding agents, in particular: organic bases, such as triethylamine, pyridine, 2,6-lutidine or N,N-dimethylaniline; alkali metal bicarbonates, such as sodium bicarbonate; alkali metal carbonates, such as sodium carbonate or potassium carbonate; alkaline earth metal carbonates, such as calcium carbonate; and alkali metal hydrides, such as sodium hydride or potassium hydride.

An alternative way of carrying out this reaction is to react the compound of formula (XIIa) with a silver salt of tetrafluoroboric acid, nitric acid or p-toluenesulphonic acid in the presence of an organic base, such as those exemplified above, and then subjecting the resulting compound to alkylation with the alkylating agent of formula (XIX).

The reaction temperature is not critical, although we prefer to carry out the reaction at relatively low temperatures in order to control side reactions. Accordingly, the reaction temperature is preferably from $-10°$ C. to $+100°$ C. The time required for the reaction will depend mainly upon the reaction temperature and upon the nature of the starting material, but in general the reaction will be complete within a period of from several minutes to 100 hours.

After completion of the reaction, the desired product of formula (XX) may be recovered from the reaction mixture by conventional means. One suitable recovery sequence comprises: diluting the reaction mixture with a water-immiscible organic solvent; washing the mixture with water; and distilling off the solvent to give the desired product. This product may, if necessary, be further purified by conventional means, for example by recrystallization, reprecipitation or chromatography.

Where the compound of formula (XX) prepared as described above is the 5S-isomer, it can readily be converted to the corresponding 5R-isomer by heating in an organic solvent, such as toluene, xylene, dimethylformamide or dimethylacetamide.

Step (b)

In this step, protecting groups are, if necessary, removed. The removal reactions, which will, of course, depend upon the nature of the protecting groups, may all be carried out as described in relation to the corresponding protecting groups in step (d) of Method A. Recovery of the desired compound from the resulting reaction mixture may also be effected as described in step (d) of Method A.

Where the compound of formula (I) prepared as described by any of the above Methods includes in its group represented by $R^1$ in formula (I) a secondary alcohol grouping (i.e. $R^1$ represents a hydroxy-substituted alkyl group), the configuration of the hydroxy group can, if necessary, be altered by reactions well-known in the field of β-lactam chemistry. For example, if a compound of formula (Ia) in which $R^1$ represents a 1-hydroxyethyl group in the S- configuration is treated with an organic acid in the presence of a phosphine derivative (such as triphenylphosphine) and of an azodicarboxylic acid diester (such as diethyl azodicarboxylate), it is possible to obtain the corresponding compound of formula (Ia) in which $R^1$ represents a 1-acyloxyethyl group in the R-configuration, in other words the substituent at the 1-position of the 6-side chain has been inverted. Preferred organic acids include: lower fatty acids, such as formic acid, acetic acid or propionic acid; aromatic carboxylic acids, such as benzoic acid; and aralkanoic acids, such as phenylacetic acid. The solvent employed and the reaction conditions are similar to those described in step (d) above of Method A in relation to the acylation reaction. The acyloxy compound thus obtained may then be converted to various derivatives (including, if desired, the corresponding hydroxy compound) by combining various of the reactions described in step (d) of Method A. After completion of these reactions, the desired compound from each step may be recovered by conventional means, for example by distilling off the solvent under reduced pressure, adding water and a water-immiscible organic solvent to the residue, separating the organic layer and washing it with water, drying the resulting organic solution over a drying agent, and finally distilling the solvent from this organic solution to give the desired product which may, if required, be further purified by such conventional means as recrystallization, preparative thin layer chromatography or column chromatography.

Where the compound of formula (I) prepared by any of the above Methods includes a free carboxy group, for example where $R^3$ represents a carboxy group, it may be converted to a pharmaceutically acceptable salt, especially those salts heretofore exemplified, by methods well-known in the art.

The 4-alkylthio-2-azetidinone compounds of formula (II) which represent the starting materials used in most of the Methods described above, can be synthesized by various routes, including those illustrated in Methods G, H and I below.

METHOD G

The method of T. Kobayashi, T. Iwano and K. Hirai in Chem. Pharm. Bull., 26, 1761(1978) can be summarized by the following equation:

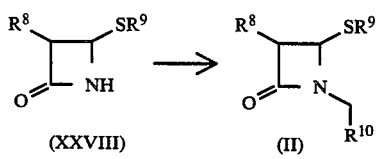

In the above formulae, $R^8$, $R^9$ and $R^{10}$ are as defined above. By carrying out the method reported in the cited article, it is only possible to obtain the compound of formula (II) in which $R^{10}$ represents a p-nitrobenzyloxycarbonyl group in very low yields. However, this compound can be obtained in higher yields by reacting the compound of formula (XXVIII) with a p-nitrobenzyl ester of a halogenated acetic acid in the presence of powdered potassium hydroxide and in an ether solvent, for example tetrahydrofuran.

METHOD H

An alternative means of preparing the compounds of formula (II) is illustrated by the following reaction scheme:

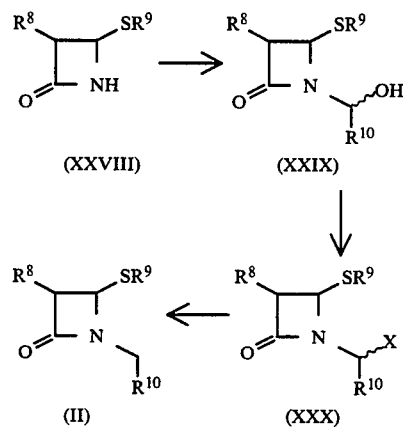

In the above formulae, $R^8$, $R^9$, $R^{10}$ and X are as defined above.

In the first step of this reaction, the compound of formula (XXVIII), which is a known compound, is reacted with a glyoxylic acid ester of formula (XXXI):

$$OHC-R^{10} \qquad (XXXI)$$

(in which $R^{10}$ represents a protected carboxy group). This reaction may be carried out by conventional methods in the presence of a suitable solvent.

The second step in this reaction comprises reacting the compound of formula (XXIX) thus obtained with a halogenating agent in the presence of a base. The halogenating agent used may be any one of those commonly employed for the halogenation of azetidin-2-one derivatives.

The third step in this reaction comprises reducing the compound of formula (XXX) to give the desired compound of formula (II). This reaction may be conducted by contacting the compound of formula (XXX) with a reducing agent in the presence of a solvent. There is no particular limitation on the nature of the solvent employed, provided that it does not adversely affect the reaction, and preferred solvents are fatty acid dialkylamides (such as dimethylformamide or dimethylacetamide) or hexamethylphosphoramide. Preferred reducing agents are boron compounds, such as sodium cyanoboron hydride. When X in the compound of formula (XXX) represents chlorine or bromine, the reduction can be promoted by the presence of an inorganic iodine compound such as sodium iodide or potassium iodide. The reaction temperature is not critical and the reaction is normally carried out at a temperature from 0° C. to 100° C. The time required for the reaction will depend upon the nature of the starting materials and solvents and upon the reaction temperature, but the reaction is normally complete within from 10 minutes to 10 hours.

After completion of the reaction, the desired compound of formula (II) can be recovered from the reaction mixture by conventional means. For example, the reaction mixture can be poured into ice-water and the precipitated compound collected by filtration. Alternatively, the mixture can be diluted with water and a water-immiscible organic solvent (such as ethyl acetate), after which the organic layer is separated, washed with water and dried over a drying agent, and then the solvent is evaporated off to give the desired compound. The compound thus obtained may, if necessary, be purified by conventional means, for example by recrystallization, preparative thin layer chromatography or column chromatography.

METHOD I

3-Alkoxy-4-alkylthio-2-azetidinone compounds, which are amongst the starting materials for use in the process of the invention can be prepared as illustrated by the following reaction scheme:

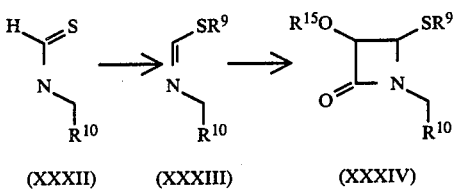

(XXXII)   (XXXIII)   (XXXIV)

In the above formulae, $R^9$ and $R^{10}$ are as defined above and $R^{15}$ represents a lower alkyl group.

The first step of this reaction scheme comprises reacting the compound of formula (XXXII) with an alkylating agent to give the Schiff base of formula (XXXIII). Any alkylating agent commonly used to prepare thioformamide derivatives may be used in this reaction. The Schiff base (XXXIII) is normally used in the next step without isolation.

The second step of this reaction scheme comprises reacting the Schiff base (XXXIII) with an acid halide of formula (XXXV):

$$R^{15}OCH_2COX \qquad (XXXV)$$

(in which $R^{15}$ is as defined above and X represents a halogen atom) in the presence of a base to give the desired azetidinone compound (XXXIV). This reaction may be carried out by the known method of preparing azetidinone derivatives described by A. K. Bose, Y. H. Chang and M. S. Manhas, Tetrahedron Letters, 4091(1972).

The term "lower alkyl group" as used herein means an alkyl group having from 1 to 6 carbon atoms and other "lower" groups are to be construed accordingly.

The penem-3-carboxylic acid derivatives of the present invention are useful as antibacterial agents and as intermediates in the synthesis of other penem derivatives for use as antibacterial agents.

The activities of compounds of the invention have been tested by an Agar plate dilution method and certain of the compounds of the invention have shown very potent antibacterial activity against a wide range of pathogenic microorganisms, including both gram-positive microorganisms (such as *Staphylococcus aureus* and *Bacillus subtilis*) and gram-negative microorganisms (such as *Escherichia coli, Shigella flexneri, Klebsiella pneumoniae,* Proteus species and *Pseudomonas aeruginosa*). The minimal inhibitory concentrations of certain representative compounds of the invention against a variety of microoganisms are shown in the following Table. In the Table, the test compounds employed are identified as follows:

A: Isomer B of Compound No. 65, i .e. 2-(1-carbamoylethylthio)-6-(1-hydroxyethyl)penem-3-carboxylic acid.

B: Compound No. 53, i.e. 2-carbamoylmethylthio-6-(1-hydroxyethyl)penem-3-carboxylic acid.

C: Compound No. 74, i.e. 2-(1-carbamoylpropylthio)-6-(1-hydroxyethyl)penem-3-carboxylic acid.

D: 2-[(2-aminoethyl)thio]-6-(1-hydroxyethyl)penem-3-carboxylic acid, the known compound disclosed in our U.S. patent application Ser. No. 137,773 filed Apr. 7, 1980.

All of the compounds were used in the form of the sodium salt and they have the (5R, 6S) and 6-1'-(R) configuration.

TABLE

| Microorganism | | Test Compound | | | |
|---|---|---|---|---|---|
| | | A | B | C | D |
| *Escherichia* | NIHJ | 0.05 | 0.4 | 0.2 | 0.4 |
| *coli* | 609 | 0.05 | 0.8 | 0.4 | 0.8 |
| *Shigella flexneri* 2a | | 0.1 | 0.8 | 0.2 | 0.8 |
| *Klebsiella* | 806 | 0.05 | 0.8 | 0.2 | 0.8 |
| *pneumoniae* | 846 | 0.05 | 0.4 | 0.4 | 0.8 |
| *Proteus vulgaris* | | 1.5 | 1.5 | 0.4 | 6.2 |
| *Salmonella enteritidis* G | | 0.1 | 0.8 | 0.4 | 0.8 |

As can be seen from the above Table, the compounds of the invention have antibacterial activities as good as or better than (and against some microorganisms significantly better than) the activities of the known compound 2-[(2-aminoethyl)thio]-6-(1-hydroxyethyl)-penem-3-carboxylic acid. Moreover, Compound No. 65 has shown a very significantly weaker acute toxicity in mice. Whereas the known compound will kill a mouse when administered by intravenous injection in an amount of from 500 to 1000 mg/kg body weight, Compound No. 65 showed no adverse effect, even when intravenously injected in an amount of 1000 mg/kg.

Accordingly, the compounds of the invention may be used for the treatment of diseases caused by many pathogenic microorganisms. For this purpose, the compounds of the invention may be administered orally (e.g. in the form of tablets, capsules, granules, powders or syrups) or parenterally (e.g. by intravenous injection or intramuscular injection). The dose will vary depending upon the age, body weight and condition of the patient and on the route and type of administration but, in general, the compounds of the invention may be administered in a daily dose of from 250 to 3000 mg for adults, either as a single dose or as divided doses.

The preparation of compounds of the invention is further illustrated by the following Examples, and the preparation of certain of the starting materials used in these Examples is illustrated by the following Preparations.

EXAMPLE 1

(a) p-Nitrobenzyl 2-(4-methylthio-2-azetidinon-1-yl)-2-(4-oxo-1,3-dithietan-2-ylidene)acetate To a solution of 740 μl hexamethyldisilazane in 12 ml of tetrahydrofuran was added a solution of butyllithium in hexane (2.4 ml, 163 mmoles/ml) at room temperature, and then the mixture was stirred for 30 minutes. A solution of 620 mg of p-nitrobenzyl 2-(4-methylthio-2-azetidinon-1-yl)acetate in 8 ml of tetrahydrofuran was then added, after cooling the mixture of −78° C., after which it was stirred for 5 minutes. To the resulting solution was added carbon disulphide (181.2 μl), and the mixture was stirred for 20 minutes. A solution of phosgene (198 mg) in benzene (468 μl) was added to the solution, and stirring was continued at −78° C. for 1 hour. Acetic acid (680 μl) was added to the reaction mixture. The resulting mixture was diluted with ethyl acetate, washed successively with water and an aqueous solution of sodium chloride, and dried over anhydrous sodium sulphate. The solvent was distilled off under reduced pressure and the resulting residue was purified by column chromatography (eluent: a 4:1 by volume mixture of benzene and ethyl acetate), to give 703 mg of the desired compound as a foamy substance.

Infrared Absorption Spectrum (CHCl$_3$) $\nu_{max}$ cm$^{-1}$: 1773, 1730, 1708.

Nuclear Magnetic Resonance Spectrum (CDCl$_3$) δ ppm: 1.93 (3H, singlet); 2.85 (1H, doubled doublet, J=15.9 and 3.0 Hz); 3.19 (1H, doubled doublet, J=15.9 and 5.0 Hz); 5.08 (1H, double doublet, J=5.0 and 3.0 Hz); 5.23 (2H, singlet); 7.44, 8.11 (4H, A$_2$B$_2$, J=8.7 Hz).

(b) p-Nitrobenzyl
2-(1-pyrrolidinylcarbonylthio)penem-3-carboxylate
(Compound No. 5)

A solution of chlorine (0.23 mmole) in carbon tetrachloride (522 μl) was added to a solution of p-nitrobenzyl 2-(4-methylthio-2-azetidinon-1-yl)-2-(4-oxo-1,3-dithietan-2-ylidene)acetate (95 mg, 0.23 mmole) in methylene chloride (2 ml), with ice cooling and stirring. When the addition was complete, the mixture was stirred for 5 minutes and then the solvent was distilled off at 0° C. to give the crude 4-chloroazetidinone compound, which was dissolved in methylene chloride (1.5 ml) without purification. To the resulting solution was added a solution of pyrrolidine (16.4 mg, 0.23 mmole) and triethylamine (25.6 mg, 0.253 mmole) in methylene chloride (0.5 ml) at 0° C. After stirring at that temperature for 1.5 hours, the reaction mixture was washed successively with water and an aqueous solution of sodium chloride. The organic layer was separated and was dried over anhydrous sodium sulphate, after which the solvent was distilled off. The resulting residue was purified by column chromatography (eluent:ethyl acetate) to afford 30 mg of the desired compound.

Infrared Absorption Spectrum (CHCl$_3$) $\nu_{max}$ cm$^{-1}$: 1788, 1690 (Shoulder), 1655.

Nuclear Magnetic Resonance Spectrum (CDCl$_3$) δ ppm: 1.59-2.27 (4H, multiplet); 2.95-4.10 (6H, multiplet); 5.17, 5.33 (2H, AB-quartet, J=14.7 Hz); 5.55 (1H, doublet); 7.56, 8.17 (4H, A$_2$B$_2$, J=8.4 Hz).

EXAMPLE 2

2-(1-Pyrrolidinylcarbonylthio)penem-3-carboxylic acid
(Compound No. 4)

p-Nitrobenzyl 2-(1-pyrrolidinylcarbonylthio)penem-3-carboxylate (25 mg) was dissolved in tetrahydrofuran (4 ml). To the solution were added a phosphate buffer solution (0.1M, pH 7.10, 4 ml) and 10% w/w palladium on charcoal (50 mg), after which the mixture was stirred in an atmosphere of hydrogen for 2 hours. The catalyst was separated by filtration and washed with water. The filtrate and the washings were combined and concentrated by evaporation under reduced pressure. The concentrate was purified by column chromatography through a Diaion HP-20 AG rasin (a product of Mitsubishi Chemical Industries, Co., 100-200 mesh; eluent: water and a 5% v/v aqueous acetone solution) and the fractions containing the desired compound were lyophilized to give 7 mg of the desired compound as a powder.

Infrared Absorption Spectrum (KBr) $\nu_{max}$ cm$^{-1}$: 1768, 1645, 1605.

Ultraviolet Absorption Spectrum (H$_2$O) $\lambda_{max}$ nm (ε): 320.5 (6020).

Nuclear Magnetic Resonance Spectrum (D$_2$O) δ ppm: 1.60-2.12 (4H, multiplet); 3.16-3.74 (4H, multiplet); 3.62 (1H, doubled doublet, J=18.6, 2.0 Hz); 3.85 (1H, doubled doublet, J=18.6, 4.0 Hz); 5.78 (1H, doubled doublet, J=4.0, 2.0 Hz).

EXAMPLE 3 p-Nitrobenzyl 2-thioxopenam-3-carboxylate
(Compound No. 2)

Following the procedure of Example 1(b), there was obtained the corresponding 4-chloroazetidinone compound from p-nitrobenzyl 2-(4-methylthio-2-azetidinon-1-yl)-2-(4-oxo-1,3-dithietan-2-ylidene)acetate (300 mg, 0.726 mmole) and chlorine (0.726 mmole). The resulting compound was dissolved in methylene chloride (4.5 ml). To the solution were added a 30% methanol solution of methylamine (1.596 mmoles, 206 μl) and a solution of triethylamine (1.596 mmoles, 221 μl) in methylene chloride (0.5 ml), with ice cooling. The mixture was stirred at that temperature for 1 hour, and then the solvent was distilled off under reduced pressure. The resulting residue was purified by column chromatography (eluent: a 97.5:2.5 by volume mixture of chloroform and methanol), to afford 155 mg of the desired compound.

Infrared Absorption Spectrum (CHCl$_3$) $\nu_{max}$ cm$^{-1}$: 1792, 1750.

Nuclear Magnetic Resonance Spectrum (CDCl$_3$) δ ppm: 3.49 (1H, doubled doublet, J=16.3 and 2.0 Hz); 3.91 (1H, doubled doublet, J=16.3 and 4.0 Hz); 5.31 (2H, singlet); 5.40 (1H, singlet); 5.88 (1H, doubled doublet, J=4.0 and 2.0 Hz); 7.50, 8.19 (4H, A$_2$B$_2$, J=9.0 Hz).

EXAMPLE 4

(a) p-Nitrobenzyl
2-[bis(acetylthio)methylidene]-2-(4-methylthio-2-azetidinon-1-yl)acetate A solution of butyllithium (1.04 ml, 1.63 mmoles/ml) in hexane (6 ml) was added to a solution of hexamethyldisilazane (309 μl) in tetrahydrofuran (6 ml) at room temperature, and then the mixture was stirred for 30 minutes. A solution of p-nitrobenzyl 2-(4-methylthio-2-azetidinon-1-yl)acetate (250 mg) in tetrahydrofuran (5 ml) was added to the resulting solution, after cooling it to −78° C. The solution was stirred for 5 minutes, and then carbon disulphide (73 μl) was added thereto, after which the mixture was stirred for 20 minutes. To the resulting solution was added acetyl chloride (120 μl), followed by stirring for 1 hour. After addition of acetic acid (250 μl), the reaction mixture was diluted with ethyl acetate and washed successively with an aqueous solution of sodium chloride, an aqueous solution of sodium bicarbonate and an aqueous solution of sodium chloride. The mixture was dried over anhydrous sodium sulphate and the solvent was distilled off under reduced pressure. The resulting residue was purified by silica gel column chromatography (eluent: a 10:1 by volume mixture of benzene and ethyl acetate), to give 303 mg of the desired product as crystals.

Infrared Absorption Spectrum (KBr) $\nu_{max}$ cm$^{-1}$: 1780, 1740, 1700.

Nuclear Magnetic Resonance Spectrum (CDCl$_3$) δ ppm: 2.10 (3H, singlet); 2.21 (3H, singlet); 2.37 (3H, singlet); 3.12 (1H, doubled doublet, J=16.5 and 3.5 Hz); 3.50 (1H, doubled doublet, J=16.5 and 5 Hz); 5.37 (2H, singlet); 5.44 (1H, doubled doublet, J=5 and 3.5 Hz); 7.61, 8.29 (4H, A$_2$B$_2$, J=9 Hz).

(b) p-Nitrobenzyl 2-thioxopenam-3-carboxylate (Compound No. 2)

Following the procedure of Example 1(b), a carbon tetrachloride solution containing an equimolar amount of chlorine was added to a solution of p-nitrobenzyl 2-[bis(acetylthio)methylidene]-2-(4-methylthio-2-azetidinon-1-yl)acetate (144 mg, 0.306 mmole) in methylene chloride (2 ml) to give p-nitrobenzyl 2-[bis(acetylthio)methylidene]-2-(4chloro-2-azetidinon-1-yl)acetate. This crude 4-chloroazetidinone derivative was dissolved in methylene chloride (3 ml) and triethylamine (43 µl), and then 135 µl of a 30% methanol solution of methylamine were added thereto, after which the mixture was stirred for 15 minutes. The solvent was distilled off under reduced pressure. The residue was purified by column chromatography (eluent:ethyl acetate) to afford 60 mg of the desired compound.

EXAMPLE 5

(a) p-Nitrobenzyl 2-(4-oxo-1,3-dithietan-2-ylidene)-2-[3-(1-t-butyldimethylsilyloxyethyl)-4-methylthio-2-azetidinon-1-yl]acetate Following the procedure of Example 1(a), there were obtained 76 mg of the desired product from p-nitrobenzyl [3-(1-t-butyldimethylsilyloxyethyl)-4-methylthio-2-azetidinon-1-yl]acetate (100 mg, 0.213 mmole).

Infrared Absorption Spectrum (CHCl$_3$) $\nu_{max}$ cm$^{-1}$: 1758, 1730, 1700.

Nuclear Magnetic Resonance Spectrum (CDCl$_3$) δ ppm: 0.04 (6H, singlet); 0.82 (9H, singlet); 1.23 (3H, doublet, J=6.0 Hz); 2.07 (3H, singlet); 3.22 (1H, doubled doublet, J=4.5 and 2.0 Hz); 4.29 (1H, multiplet); 5.36 (1H, doublet, J=2.0 Hz); 5.25, 5.53 (2H, AB-quartet, J=12.9 Hz); 7.66, 8.35 (4H, A$_2$B$_2$, J=8.7 Hz).

(b) p-Nitrobenzyl 6-(1-t-butyldimethylsilyloxyethyl)-2-thioxopenam-3-carboxylate (Compound No. 11)

Following the procedure of Example 3, there were obtained 46 mg of the desired compound from p-nitrobenzyl 2-(4-oxo-1,3-dithietan-2-ylidene)-2-[3-(1-t-butyldimethylsilyloxyethyl)-4-methylthio-2-azetidinon-1-yl]acetate (76 mg).

Nuclear Magnetic Resonance Spectrum (CDCl$_3$) δ ppm: 0.12 (6H, singlet); 0.85 (9H, singlet); 1.36 (3H, doublet, J=6.0 Hz); 3.83 (1H, doubled doublet, J=10 and 4 Hz); about 4.2 (1H, multiplet); 5.22 (3H, singlet); 5.91 (1H, doublet, J=4 Hz); 7.40, 8.10 (4H, A$_2$B$_2$, J=8.5 Hz).

EXAMPLE 6

(a) p-Nitrobenzyl 2-(3,3-dimethyl-2,4-dioxo-1,3-dithian-2-ylidene)-2-(4-methylthio-2-azetidinon-1-yl)acetate To a solution of hexamethyldisilazane (619 µl) in tetrahydrofuran (10 ml) was added, at room temperature, a solution of butyllithium in hexane (2.08 ml, 163 mmole/ml), and the resulting solution was stirred for 30 minutes. The solution was then cooled to −78° C., and a solution of p-nitrobenzyl 2-(4-methylthio-2-azetidinon-1-yl)acetate (500 mg) in tetrahydrofuran (10 ml) was added thereto. After stirring the solution for 20 minutes, 2,2-dimethylmalonic acid dichloride (324 mg) was added thereto, and the solution was stirred at −78° C. for 1 hour. Acetic acid (1.5 ml) was added to the reaction mixture, which was washed, in turn, with water and an aqueous solution of sodium chloride, and then dried over anhydrous magnesium sulphate. The solvent was distilled off under reduced pressure, and the resulting residue was purified through column chromatography (eluent: a 2:1 by volume mixture of benzene and ethyl acetate), giving 338 mg of the desired compound.

Infrared Absorption Spectrum (CHCl$_3$) $\nu_{max}$ cm$^{-1}$: 1782, 1715.

Nuclear Magnetic Resonance Spectrum (CDCl$_3$) δ ppm: 1.52 (3H, singlet); 1.61 (3H, singlet); 2.13 (3H, singlet); 3.12 (1H, doubled doublet, J=2.0 and 15.0 Hz); 3.37 (1H, doubled doublet, J=4.0 and 15.0 Hz); 5.28 (1H, doubled doublet, J=2.0 and 4.0 Hz); 5.34 (2H, singlet); 7.54, 8.21 (4H, A$_2$B$_2$, J=9.0 Hz).

(b) p-Nitrobenzyl 2-thioxopenam-3-carboxylate (Compound No. 2)

Following the method of Example 4(b), a solution containing an equimolar amount of chlorine in carbon tetrachloride was added to a solution of p-nitrobenzyl 2-(3,3-dimethyl-2,4-dioxo-1,3-dithian-2-ylidene)-2-(4-methylthio-2-azetidinon-1-yl)acetate (150 mg) in methylene chloride (3 ml) to afford p-nitrobenzyl 2-(3,3-dimethyl-2,4-dioxo-1,3-dithian-2-ylidene)-2-(4-chloro-2-azetidinon-1-yl)acetate. This crude 4-chloroazetidinone derivative was dissolved in methylene chloride (2 ml) and triethylamine (47 µl) and a 30% solution of methylamine in methanol (98 µl) were added thereto, with ice cooling, after which the mixture was stirred for 15 minutes. The solvent was distilled off under reduced pressure, and the resulting residue was purified by column chromatography (eluent: ethyl acetate), giving 60 mg of the desired compound, having the same properties as the product of Example 3.

EXAMPLE 7

(a) p-Nitrobenzyl 2-(1,5-dioxo-1,5-dihydro-2,4-benzo[e]dithiepin-3-ylidene)-2-[3-(1-t-butyldimethylsilyloxyethyl)-4-methylthio-2-azetidinon-1-yl]acetate Following the procedures of Example 6(a), p-nitrobenzyl [3-(1-t-butyldimethylsilyloxyethyl)-4-methylthio-2-azetidinon-1-yl]acetate (2.24 g), hexamethyldisilazane (1.99 ml), a solution of butyllithium in hexane (5.82 ml), carbon disulphide (427 µl) and phthaloyl chloride (750 µl) were reacted and the reaction mixture was purified through silica gel column chromatography (eluent: methylene chloride) to afford 3.02 g of the desired compound.

Nuclear Magnetic Resonance Spectrum (CDCl$_3$) δ ppm: 0.05 (6H, singlet); 0.85 (9H, singlet); 1.24 (3H, doublet, J=6.0 Hz); 2.17 (3H, singlet); 3.22 (1H, doubled doublet, J=2.5 and 4.0 Hz); 4.0–4.5 (1H, multiplet); 5.18 (1H, doublet, J=2.5 Hz); 5.28, 5.47 (2H, AB-quartet, J=13 Hz); 7.5–8.4 (8H, multiplet).

(b) p-Nitrobenzyl (5S,6S)-6-(1CR)-t-butyldimethylsilyloxyethyl)-2-thioxopenam-3-carboxylate (Compound No. 11)

p-Nitrobenzyl 2-(1,5-dioxo-1,5-dihydro-2,4-benzo[e]-dithiepin-3-ylidene)-2-[3-(1-t-butylidimethylsilyloxyethyl)-4-methylthio-2-azetidinon-1-yl]acetate (3.0 g) was chlorinated with an equimolar amount of chlorine, in a similar manner to that described in Example 6(b) and the product was then dissolved in diethyl ether (120 ml). To the reaction mixture was added ammonia dissolved in diethyl ether for 10 minutes, with ice cooling. The ether was distilled off and the residue was extracted with ethyl acetate. The extract was washed with a saturated aqueous solution of sodium chloride and the solvent was distilled off. The residue was purified by short column chromatography (eluent: ethyl acetate), giving 1.87 g of the desired compound.

EXAMPLE 8 p-Nitrobenzyl (5S,6S)-6-[1-(R)-t-butyldimethylsilyloxyethyl]-2-(1-carbamoylethylthio)penem-3-carboxylate (Isomers A and B of Compound No. 73)

Triethylamine (36.9 mg) and 2-iodopropionamide (165 mg) were added to a solution of p-nitrobenzyl 6-(1-t-butyldimethylsilyloxyethyl)-2-thioxopenam-3-carboxylate (165 mg), prepared as described in Example 5(b), in methylene chloride (3 ml). The resulting mixture was stirred at room temperature for 6 hours and then left to stand overnight. The reaction mixture was washed with water and dried. The solvent was distilled off and the residue was purified by silica gel chromatography (eluent: a 1:1 by volume mixture of benzene and ethyl acetate), to give the desired compound (isomer A, 31 mg; isomer B, 32 mg).

Isomer A

Infrared Absorption Spectrum (CHCl$_3$) $\nu_{max}$ cm$^{-1}$: 3520, 3400, 1782, 1688.

Nuclear Magnetic Resonance Spectrum (CDCl$_3$) δ ppm: 0.12 (6H, singlet); 0.84 (9H, singlet); 1.33 (3H, doublet, J=5.8 Hz); 1.54 (3H, doublet, J=6.5 Hz); 3.75 (1H, doubled doublet, J=10.0 and 4.0 Hz); 3.82 (1H, quartet, J=6.5 Hz); 3.98–4.47 (1H, multiplet); 5.11, 5.37 (2H, AB-quartet, J=14.4 Hz); 5.63 (1H, doublet, J=4.0 Hz); 6.05 (2H, broad singlet); 7.53, 8.15 (4H, A$_2$B$_2$, J=9.0 Hz).

Isomer B

Infrared Absorption Spectrum (CHCl$_3$) $\nu_{max}$ cm$^{-1}$: 3520, 3400, 1782, 1688.

Nuclear Magnetic Resonance Spectrum (CDl$_3$) δ ppm: 0.13 (6H, singlet); 0.84 (9H, singlet); 1.36 (3H, doublet, J=5.5 Hz); 1.54 (3H, doublet, J=7.0 Hz); 3.74 (1H, doubled doublet, J=10.0 and 4.0 Hz); 3.77 (1H, quartet, J=7.0 Hz); 3.98–4.48 (1H, multiplet); 5.09, 5.35 (2H, AB-quartet, J=14.4 Hz); 5.60 (1H, doublet, J=4.0 Hz); 6.24 (2H, broad singlet); 7.53, 8.13 (4H, A$_2$B$_2$, J=9.3 Hz).

EXAMPLE 9 p-Nitrobenzyl (5R,6S)-6-[1-(R)-t-butyldimethylsilyloxyethyl]-2-(1-carbamoylethylthio)penem-3-carboxylate (Compound No. 73)

Isomer A

Isomer A of p-nitrobenzyl (5S,6S)-6-[1-(R)-t-butyldimethylsilyloxyethyl]-2-(1-carbamoylethylthio)-penem-3-carboxylate (51 mg) was dissolved in xylene (5 ml), and hydroquinone (2.5 mg) was added thereto. The mixture was stirred on an oil bath at 140° C. in a stream of nitrogen gas for 1 hour. The solvent was distilled off under reduced pressure. The residue was purified by silica gel chromatography (eluent: a 1:1 by volume mixture of benzene and ethyl acetate), to afford the desired compound and unreacted starting material. The recovered starting material was heated again to give more of the desired compound. The total yield was 36 mg.

Infrared Absorption Spectrum (CHCl$_3$) $\nu_{max}$ cm$^{-1}$: 3520, 3400, 1785, 1685.

Nuclear Magnetic Resonance Spectrum (CDCl$_3$) δ ppm: 0.03 (3H, singlet); 0.08 (3H, singlet); 0.78 (9H, singlet); 1.15 (3H, doublet, J=6.0 Hz); 1.52 (3H, doublet, J=7.0 Hz); 3.71 (1H, doubled doublet, J=4.0 and 1.8 Hz); 3.85 (1H, quartet, J=7.0 Hz); 4.0–4.4 (1H, multiplet); 5.16, 5.38 (2H, AB-quartet, J=13.5 Hz); 5.64 (1H, doublet, J=1.8 Hz); 6.40 (2H, broad singlet); 7.62, 8.20 (4H, A$_2$B$_2$, J=8.7 Hz).

Isomer B

Isomer B of p-nitrobenzyl (5S,6S)-6-[1-(R)-t-butyldimethylsilyloxyethyl)-2-(1-carbamoylethylthio)]-penem-3-carboxylate (60 mg) was heated in xylene under the same conditions as were used for the preparation of Isomer A to give 39 mg of the desired compound.

Infrared Absorption Spectrum (CHCl$_3$) $\nu_{max}$ cm$^{-1}$: 3520, 3400, 1685, 1685.

Nuclear Magnetic Resonance Spectrum (CDCl$_3$) δ ppm: 0.04 (3H, singlet); 0.07 (3H, singlet); 0.83 (9H, singlet); 1.22 (3H, doublet, J=5.8 Hz); 1.60 (3H, doublet, J=7.2 Hz); 3.78 (1H, doubled doublet, J=4.0 and 1.8 Hz); 3.92 (1H, quartet J=7.2 Hz); 4.1–4.5 (1H, multiplet); 5.25–5.47 (2H, AB-quartet, J=13.8 Hz); 5.73 (1H, doublet, J=1.8 Hz); 6.44 (2H, broad singlet); 7.73, 8.33 (4H, A$_2$B$_2$, J=8.1 Hz).

EXAMPLE 10 p-Nitrobenzyl (5R,6S)-6-[1-(R)-hydroxyethyl]-2-(1-carbamoylethylthio)penem-3-carboxylate (Compound No. 77)

Isomer A

Acetic acid (38.9 μl) and tetrabutylammonium fluoride (102 mg) were added to a solution of isomer A of p-nitrobenzyl (5R,6S)-6-[1-(R)-t-butyldimethylsilyloxyethyl]-2-(1-carbamoylethylthio)penem-3-carboxylate (35 mg) in tetrahydrofuran (1 ml). The mixture was left to stand at room temperature for 2 days. The reaction mixture was then diluted with ethyl acetate and washed successively with a saturated aqueous solution of sodium chloride, a 5% w/v aqueous solution of sodium bicarbonate and a saturated aqueous solution of sodium chloride. The solvent was distilled off and the residue was purified by silica gel chromatography (eluent: a 10:1 by volume mixture of chloroform and methanol), to afford 20 mg of the desired compound.

Infrared Absorption Spectrum (KBr) $\nu_{max}$ cm$^{-1}$: 3420, 1780, 1673, 1655.

Nuclear Magnetic Resonance Spectrum (heptadeuterated dimethylformamide) δ ppm: 1.20 (3H, doublet, J=5.0 Hz); 1.48 (3H, doublet, J=6.5 Hz); 3.63–4.43 (3H, multiplet); 5.22, 5.40 (2H, AB-quartet, J=14.1 Hz); 5.70 (1H, doublet, J=1.5 Hz); 7.03–7.25 (2H, broad singlet); 7.68, 8.15 (4H, A$_2$B$_2$, J=8.7 Hz).

Isomer B

Isomer B of p-nitrobenzyl (5R,6S)-6-[1-(R)-t-butyldimethylsilyloxyethyl]-2-(1-carbamoylethylthio)-penem-3-carboxylate (38 mg) was treated in the same way as isomer A above to give 20 mg of the desired compound.

Infrared Absorption Spectrum (KBr) $\nu_{max}$ cm$^{-1}$: 3430, 1788, 1685, 1655.

Nuclear Magnetic Resonance Spectrum (heptadeuterated dimethylformamide) δ ppm: 1.25 (3H, J=5.5 Hz); 1.58 (3H, doublet, J=7.5 Hz); 3.62–4.30 (3H, multiplet); 5.24, 5.45 (2H, AB-quartet, J=13.8 Hz); 5.78 (1H, doublet, J=1.5 Hz); 7.06–7.38 (2H, broad singlet); 7.75, 8.21 (2H, A$_2$B$_2$, J=8.70 Hz).

EXAMPLE 11

Sodium(5R,6S)-2-(1-carbamoylethylthio)-6-[1-(R)-hydroxyethyl]penem-3-carboxylate (Sodium salt of Compound No. 65)

Isomer A

Isomer A of p-nitrobenzyl(5R,6S)-6-[1-(R)-hydroxyethyl]-2-(1-carbamoylethylthio)penem-3-carboxylate (20 mg) was dissolved in a mixture of tetrahydrofuran (4 ml) and a phosphate buffer solution (pH 7.10, 4 ml). A 10% w/w palladium on charcoal catalyst (38 mg) was suspended in the above solution. The suspension was kept in contact with hydrogen gas for 1.5 hours. After completion of the reaction, the reaction mixture was filtered using a Celite (Trade Mark) filter aid under reduced pressure to remove the catalyst. The filtrate was extracted and washed with ethyl acetate; the organic phase was discarded, and water was distilled off from the aqueous phase to give about 1 ml of a mixture, which was purified by chromatography through Diaion HP-20AG (a product of Mitsubishi Chemical Industries, Co., 100–200 mesh) to give 10 mg of the desired compound.

Infrared Absorption Spectrum (KBr) $\nu_{max}$ cm$^{-1}$: 3400, 1760, 1670, 1585.

Nuclear Magnetic Resonance Spectrum (D$_2$O) δ ppm: 1.30 (3H, doublet, J=6.0 Hz); 1.51 (3H, doublet, J=7.0 Hz); 3.93 (1H, doubled doublet, J=6.0 and 1.5 Hz); 4.02 (1H, quartet, J=7.0 Hz); 4.15–4.4 (1H, multiplet); 5.68 (1H, doublet, J=1.5 Hz).

Isomer B

Isomer B of p-nitrobenzyl(5R,6S)-6-[1-(R)-hydroxyethyl]-2-(1-carbamoylethylthio)penem-3-carboxylate (20 mg) was treated in the same way as isomer A above to afford 10 mg of the desired compound.

Infrared Absorption Spectrum (KBr) $\nu_{max}$ cm$^{-1}$: 3400, 1760, 1670, 1585.

Nuclear Magnetic Resonance Spectrum (D$_2$O) δ ppm: 1.29 (3H, doublet, J=6.0 Hz); 1.54 (3H, doublet, J=7.0 Hz); 3.91 (1H, doubled doublet, J=6.0 and 1.5 Hz); 4.01 (1H, quartet, J=7.0 Hz); 4.15–4.40 (1H, multiplet); 5.69 (1H, doublet, J=1.5 Hz).

EXAMPLE 12

Methyl 2-(3,3,3-trifluoro-2-oxopropylthio)penem-3-carboxylate hydrate (Compound No. 21)

Sulphuryl chloride (59.7 mg, 35.8 μl, 0.442 mmole) was added to a solution of methyl 2-(4-methylthio-2-azetidinon-1-yl)-2-(4-trifluoromethyl-4-hydroxy-1,3-dithiolan-2-ylidene)acetate (166 mg, 0.442 mmole) in methylene chloride (3 ml) at room temperature, with stirring. After this addition, the solution was stirred for 3 minutes and then the solvent was distilled off to give the crude methyl 2-(4-chloro-2-azetidinon-1-yl)-2-(4-trifluoromethyl-4-hydroxy-1,3-dithiolan-2-ylidene)acetate. This 4-chloroazetidinone compound was dissolved in methylene chloride (3 ml) without purification, and triethylamine (185 μl) was added thereto, after which the mixture was stirred at room temperature for 2 hours. The solvent was distilled off from the reaction mixture under reduced pressure. The resulting residue was dissolved in ethyl acetate and washed with an aqueous solution of sodium chloride and dried over anhydrous sodium sulphate. The solvent was distilled off under reduced pressure and the residue was purified by preparative thin layer chromatography (eluent: a 3:2 by volume mixture of benzene and ethyl acetate), to give 63 mg of the desired product as crystals.

Infrared Absorption Spectrum (KBr) $\nu_{max}$ cm$^{-1}$: 1675, 1770, 3330.

Nuclear Magnetic Resonance Spectrum (CD$_3$.CO.CD$_3$) δ ppm: 3.49 (2H, singlet); 3.48 (1H, doubled doublet, J=17 and 2 Hz); 3.94 (1H, doubled doublet, J=17 and 4 Hz); 5.83 (1H, doubled doublet, J=4 and 2 Hz); 6.43 (2H, broad singlet).

EXAMPLE 13 p-Nitrobenzyl 2-(3,3,3-trifluoro-2-oxopropylthio)penem-3-carboxylate hydrate (Compound No. 78)

Following the procedure of Example 12, the desired product was obtained as crystals from p-nitrobenzyl 2-(4-methylthio-2-azetidinon-1-yl)-2-(4-trifluoromethyl-4-hydroxy-1,3-dithiolan-2-ylidene)acetate.

Nuclear Magnetic Resonance Spectrum (CD$_3$.CO.CD$_3$) δ ppm: 3.44 (2H, singlet); 3.46 (1H, doubled doublet, J=17 and 2 Hz); 3.90 (1H, doubled doublet, J=17 and 4 Hz); 5.50 (2H, AB-quartet, J=14 Hz); 5.79 (1H, doubled doublet, J=4 and 2 Hz); 6.48 (2H, broad singlet); 7.75, 8.26 (4H, A$_2$B$_2$, J=9 Hz).

EXAMPLE 14 p-Nitrobenzyl 2-(2-oxopropylthio)penem-3-carboxylate (Compound No. 79)

Following the procedure of Example 12, the desired product was obtained as crystals from p-nitrobenzyl 2-(4-hydroxy-4-methyl-1,3-dithiolan-2-ylidene)-2-(4-methylthio-2-azetidinon-1-yl)acetate.

Mass Spectrum m/e: 394 (M+).

Infrared Absorption Spectrum (CHCl$_3$) $\nu_{max}$ cm$^{-1}$: 1805, 1720, 1700.

Nuclear Magnetic Resonance Spectrum (hexadeuterated dimethyl sulphoxide) δ ppm: 2.12 (3H, singlet); 3.41 (1H, doubled doublet, J=16.0 and 2.0 Hz); 3.75 (1H, doubled doublet, J=16.0 and 4.0 Hz); 4.04

(2H, singlet); 5.26 (2H, broad singlet); 5.66 (1H, doubled doublet, J=4.0 and 2.0 Hz); 7.59, 8.14 (4H, A$_2$B$_2$, J=9.0 Hz).

EXAMPLE 15 p-Nitrobenzyl 2-(2-oxo-2-phenylethylthio)penem-3-carboxylate (Compound No. 23)

Following the procedure of Example 12, the desired product was obtained from p-nitrobenzyl 2-(4-hydroxy-4-phenyl-1,3-dithiolan-2-ylidene)-2-(4-methylthio-2-azetidinon-1-yl)acetate.

Infrared Absorption Spectrum (CHCl$_3$) $\nu_{max}$ cm$^{-1}$: 1805, 1715, 1695.

Nuclear Magnetic Resonance Spectrum (CDCl$_3$) δ ppm: 3.53 (1H, doubled doublet, J=15.3 and 2.0 Hz); 3.83 (1H, doubled doublet, J=15.3 and 4.0 Hz); 4.52 (2H, broad singlet); 5.39 (2H, doublet); 5.76 (1H, doubled doublet, J=4.0 and 2.0 Hz); 7.45–8.40 (9H, multiplet).

EXAMPLE 16 p-Nitrobenzyl 2-carbamoylmethylthiopenem-3-carboxylate (Compound No. 80)

Sulphuryl chloride (28.5 mg, 0.211 mmole) was added to a solution of p-nitrobenzyl 2-(4-methylthio-2-azetidinon-1-yl)-2-(4-oxo-1,3-dithiolan-2-ylidene)acetate (90 mg, 0.211 mmole) in methylene chloride (2 ml), with ice cooling and stirring. After completion of the addition, the solution was stirred for 10 minutes and then the solvent was distilled off at 0° C. to give the crude 4-chloroazetidinone compound. This product was dissolved in methylene chloride (2 ml) without purification and a solution containing a molar excess of ammonia in methylene chloride was added thereto at 0° C. The solution was stirred at that temperature for 1 hour. The solvent was distilled off under reduced pressure and the residue was purified by column chromatography (eluent: ethyl acetate) to afford 17 mg of the desired product as crystals.

Infrared Absorption Spectrum (KBr) $\nu_{max}$ cm$^{-1}$: 3370, 3180, 1785, 1685, 1670.

Nuclear Magnetic Resonance Spectrum (heptadeuterated dimethylformamide) δ ppm: 3.63 (1H, doubled doublet, J=14.4 and 20 Hz); 3.93 (2H, singlet); 3.98 (1H, doubled doublet, J=14.4 and 3.5 Hz); 5.40, 5.56 (2H, AB-quartet, J=14.1 Hz); 5.92 (1H, doubled doublet; J=3.5 and 2.0 Hz); 7.28 (2H, broad singlet); 7.86, 8.34 (4H, A$_2$B$_2$, J=9.0 Hz).

EXAMPLE 17 p-Nitrobenzyl 2-(N-methylcarbamoylmethylthio)penem-3-carboxylate (Compound No. 81)

A solution of chlorine (0.234 mmole) in carbon tetrachloride was added to a solution of p-nitrobenzyl 2-(4-methylthio-2-azetidinon-1-yl)-2-(4-oxo-1,3-dithiolan-2-ylidene)acetate (100 mg, 0.234 mmole) in methylene chloride (1.5 ml), with ice cooling and stirring. After completion of the addition, the solution was stirred for 5 minutes and then the solvent was distilled off at 0° C. to give the crude 4-chloroazetidinone compound. This product, without purification, was dissolved in methylene chloride (1.5 ml) at 0° C., and a solution of methylamine in methanol (corresponding to 0.468 mmole) was added thereto. After stirring at that temperature for 1 hour, the solution was washed with water and dried over anhydrous sodium sulphate. The solvent was then distilled off under reduced pressure. The resulting residue was purified by column chromatography (eluent: methyl acetate), to afford 18 mg of the desired product.

Infrared Absorption Spectrum (KBr) $\nu_{max}$ cm$^{-1}$: 3300, 1775, 1678, 1640.

Nuclear Magnetic Resonance Spectrum (heptadeuterated dimethylformamide) δ ppm: 2.77 (3H, doublet, J=5.0 Hz); 3.65 (1H, doubled doublet, J=16.2 and 2.0 Hz); 4.04 (1H, doubled doublet, J=16.2 and 4.0 Hz); 3.93 (2H, singlet); 5.42, 5.60 (2H, AB-quartet, J=14.4 Hz); 5.96 (1H, doubled doublet, J=4.0 and 2.0 Hz); 7.91, 8.40 (4H, A$_2$B$_2$, J=8.7 Hz).

EXAMPLE 18 p-Nitrobenzyl 2-(1-carbamoylethylthio)penem-3-carboxylate, a mixture of two isomers (Compound No. 82)

Following the procedure of Example 17, the corresponding 4-chloroazetidinone compound was obtained from p-nitrobenzyl 2-(5-methyl-4-oxo-1,3-dithiolan-2-ylidene)-2-(4-methylthio-2-azetidinon-1-yl)acetate (80 mg, 0.182 mmole). The product was further reacted with an excess of ammonia to afford the desired product (isomer A 15 mg, isomer B 18 mg).

Isomer A

Infrared Absorption Spectrum (KBr) $\nu_{max}$ cm$^{-1}$: 3420, 3180, 1777, 1670, 1650.

Nuclear Magnetic Resonance Spectrum (heptadeuterated dimethylformamide) δ ppm: 1.57 (3H, doublet, J=7.0 Hz); 3.51 (1H, doubled doublet, J=15.9 and 2.0 Hz); 3.92 (1H, doubled doublet, J=15.9 and 4.0 Hz); 4.10 (1H, quartet, J=7.0 Hz); 5.31, 5.48 (2H, AB-quartet, J=15.3 Hz); 5.88 (1H, doubled doublet, J=4.0 and 2.0 Hz); 7.24 (2H, broad singlet); 7.81, 8.28 (4H, A$_2$B$_2$, J=9.0 Hz).

Isomer B

Infrared Absorption Spectrum (KBr) $\nu_{max}$ cm$^{-1}$: 3420, 3200, 1760, 1685, 1665, 1653.

Nuclear Magnetic Resonance Spectrum (heptadeuterated dimethylformamide) δ ppm: 1.52 (3H, doublet, J=7.0 Hz); 3.59 (1H, doubled doublet, J=16.5 and 2.0 Hz); 3.98 (1H, doubled doublet, J=16.5 and 4.0 Hz); 4.13 (1H, quartet, J=7.0 Hz); 5.36, 5.54 (2H, AB-quartet, J=14.4 Hz); 5.93 (1H, doubled doublet, J=4.0 and 2.0 Hz); 7.35 (2H, broad singlet); 7.91, 8.40 (4H, A$_2$B$_2$, J=9.0 Hz).

EXAMPLE 19 p-Nitrobenzyl 2-(1-N-methylcarbamoylethylthio)penem-3-carboxylate, a mixture of two isomers (Compound No. 83)

Following the procedure of Example 18, but replacing ammonia by methylamine, the desired product was obtained (isomer A 13 mg, isomer B 19 mg) from p-nitrobenzyl 2-(5-methyl-4-oxo-1,3-dithiolan-2-ylidene)-2-(4-methylthio-2-azetidinon-1-yl)acetate (80 mg, 0.182 mmole).

Isomer A

Infrared Absorption Spectrum (KBr) $\nu_{max}$ cm$^{-1}$: 3430, 1792, 1670, 1655.

Nuclear Magnetic Resonance Spectrum (heptadeuterated dimethylformamide) δ ppm: 1.53 (3H, doublet, J=7.0 Hz); 2.70 (3H, doublet, J=5.0 Hz); 3.58 (1H, doubled doublet, J=16.5 and 2.0 Hz); 3.97 (1H, doubled doublet, J=16.5 and 4.0 Hz); 4.08 (1H, quartet, J=7.0 Hz); 5.35, 5.50 (2H, AB-quartet, J=13.8 Hz); 5.91 (1H, doubled doublet, J=4.0 and 2.0 Hz); 7.83, 8.31 (4H, A$_2$B$_2$, J=9.3 Hz); 10.0 (1H, broad singlet).

Isomer B

Infrared Absorption Spectrum (KBr) $\nu_{max}$ cm$^{-1}$: 3300, 1783, 1680, 1645.

Nuclear Magnetic Resonance Spectrum (heptadeuterated dimethylformamide) δ ppm: 1.50 (3H, doublet, J=7.0 Hz); 2.68 (3H, doublet, J=5.0 Hz); 3.36 (1H, doubled doublet, J=15.6 and 2.0 Hz); 3.96 (1H, doubled doublet, J=15.6 and 4.0 Hz); 4.07 (1H, quartet, J=7.0 Hz); 5.36, 5.52 (2H, AB-quartet, J=15.6 Hz); 5.88 (1H, doubled doublet, J=4.0 and 2.0 Hz); 7.84, 8.31 (4H, A$_2$B$_2$, J=9.0 Hz).

EXAMPLE 20 p-Nitrobenzyl 2-(N,N-diethylcarbamoylmethylthio)penem-3-carboxylate (Compound No. 84)

Following the procedure of Example 16, but replacing the ammonia by diethylamine, 17 mg of the desired product were obtained from p-nitrobenzyl 2-(4-oxo-1,3-dithiolan-2-ylidene)-2-(4-methylthio-2-azetidinon-1-yl)acetate (46.6 mg, 0.109 mmole).

Mass Spectrum m/e: 451 (M+).

Infrared Absorption Spectrum (CHCl$_3$) $\nu_{max}$ cm$^{-1}$: 1795, 1693, 1640.

Nuclear Magnetic Resonance Spectrum (CDCl$_3$) δ ppm: 0.92–1.32 (6H, multiplet); 2.94–3.68 (6H, multiplet); 3.78 (2H, singlet); 5.14, 5.33 (2H, AB-quartet, J=13.8 Hz); 5.60 (1H, doubled doublet, J=4.0 and 2.0 Hz); 7.56, 8.14 (4H, A$_2$B$_2$, J=9.3 Hz).

EXAMPLE 21 p-Nitrobenzyl 2-[N-(2-hydroxyethyl)carbamoylmethylthio]penem-3-carboxylate (Compound No. 85)

Following the procedure of Example 17, but replacing the methylamine by ethanolamine, 56 mg of the desired product were obtained from p-nitrobenzyl 2-(4-methylthio-2-azetidinon-1-yl)-2-(4-oxo-1,3-dithiolan-2-ylidene)acetate (110 mg, 0.258 mmole).

Infrared Absorption Spectrum (KBr) $\nu_{max}$ cm$^{-1}$: 3380 (broad), 3280, 1780, 1670, 1635.

Nuclear Magnetic Resonance Spectrum (heptadeuterated dimethylformamide) δ ppm: 3.04–3.60 (4H, multiplet); 3.86 (2H, singlet); 3.55 (1H, doubled doublet, J=15.6 and 2.0 Hz); 3.90 (1H, doubled doublet, J=15.6 and 3.5 Hz); 4.55 (1H, broad singlet); 5.26, 5.42 (2H, AB-quartet, J=13.5 Hz); 5.78 (1H, doubled doublet, J=3.5 and 2.0 Hz); 7.72, 8.19 (4H, A$_2$B$_2$, J=9.0 Hz); 8.16 (1H, broad singlet).

EXAMPLE 22 p-Nitrobenzyl 2-(N-p-nitrobenzyloxycarbonylmethylcarbamoylmethylthio)penem-3-carboxylate (Compound No. 86)

Following the procedure of Example 17, but replacing the methylamine by p-nitrobenzyl glycinate, 89 mg of the desired product were obtained from p-nitrobenzyl 2-(4-methylthio-2-azetidinon-1-yl)-2-(4-oxo-1,3-dithiolan-2-ylidene)acetate (110 mg, 0.258 mmole).

Infrared Absorption Spectrum (KBr) $\nu_{max}$ cm$^{-1}$: 3375, 1785, 1730, 1670, 1653.

Nuclear Magnetic Resonance Spectrum (heptadeuterated dimethylformamide) δ ppm: 3.52 (1H, doubled doublet, J=13.5 and 2.0 Hz); 3.98 (1H, doubled doublet, J=13.5 and 4.0 Hz); 4.01 (2H singlet); 4.17 (2H, doublet, J=5.5 Hz); 5.41 (2H, singlet); 5.56, 5.38 (2H, AB-quartet, J=14.1 Hz); 5.90 (1H, doubled doublet, J=4.0 and 2.0 Hz); 7.81, 8.38 (4H, A$_2$B$_2$, J=8.7 Hz); 7.90, 8.38 (4H, A$_2$B$_2$, J=9.3 Hz); 8.85 (1H, multiplet).

EXAMPLE 23 p-Nitrobenzyl 2-(2-morpholino-2-oxoethylthio)penem-3-carboxylate (Compound No. 87)

Following the procedure of Example 16, but replacing the ammonia by morpholine, 27 mg of the desired product were obtained from p-nitrobenzyl 2-(4-methylthio-2-azetidinon-1-yl)-2-(4-oxo-1,3-dithiolan-2-ylidene)acetate (93.4 mg, 0.219 mmole).

Mass Spectrum m/e: 465 (M+).

Infrared Absorption Spectrum (KBr) $\nu_{max}$ cm$^{-1}$: 1785, 1675, 1635.

Nuclear Magnetic Resonance Spectrum (heptadeuterated dimethylformamide) δ ppm: 3.28–3.94 (10H, multiplet); 4.24 (2H, singlet); 5.35, 5.49 (2H, AB-quartet, J=14.1 Hz); 5.87 (1H, doubled doublet, J=4.5 and 2.5 Hz); 7.81, 8.28 (4H, A$_2$B$_2$, J=9.3 Hz).

EXAMPLE 24 p-Nitrobenzyl 2-[2-(4-p-nitrobenzyloxycarbonyl-1-piperazinyl)-2-oxoethylthio]penem-3-carboxylate (Compound No. 37)

Following the procedure of Example 16, but replacing the ammonia by N-(p-nitrobenzyloxycarbonyl)piperazine, 72 mg of the desired product were obtained from p-nitrobenzyl 2-(4-methylthio-2-azetidinon-1-yl)-2-(4-oxo-1,3-dithiolan-2-ylidene)acetate (131 mg, 0.307 mmole).

Infrared Absorption Spectrum (CHCl$_3$) $\nu_{max}$ cm$^{-1}$: 1790, 1720 (shoulder), 1695, 1648.

Nuclear Magnetic Resonance Spectrum (CDCl$_3$) δ ppm: 3.34–3.83 (2H, multiplet); 3.60 (8H, broad singlet); 3.97 (2H, singlet); 5.10–5.66 (4H, AB-quartet); 5.78 (1H, doubled doublet, J=4.0 and 2.0 Hz); 7.61, 8.30 (4H, A$_2$B$_2$, J=9.0 Hz); 7.71, 8.30 (4H, A$_2$B$_2$, J=8.4 Hz).

EXAMPLE 25 p-Nitrobenzyl 2-hydrazinocarbonylmethylthiopenem-3-carboxylate (Compound No. 88)

Following the procedure of Example 17, but replacing the methylamine by a solution of hydrazine in methanol, 20 mg of the desired product were obtained from p-nitrobenzyl 2-(4-methylthio-2-azetidinon-1-yl)-2-(4-oxo-1,3-dithiolan-2-ylidene)acetate (100 mg, 0.234 mmole).

Infrared Absorption Spectrum (KBr) $\nu_{max}$ cm$^{-1}$: 3470, 3320 (broad), 1785, 1675, 1650.

Nuclear Magnetic Resonance Spectrum (heptadeuterated dimethylformamide) δ ppm: 3.46 (1H, doubled doublet, J=17.1 and 2.0 Hz); 3.95 (1H, doubled doublet, J=17.1 and 4.0 Hz); 3.79 (2H, singlet); 4.50 (2H, broad singlet); 5.25, 5.42 (2H, AB-quartet, J=13.5 Hz); 5.78 (1H, doubled doublet, J=4.0 and 2.0 Hz);

7.74, 8.23 (4H, A$_2$B$_2$, J=9.0 Hz); 10.32 (1H, broad singlet).

EXAMPLE 26 p-Nitrobenzyl 2-(N-hydroxycarbamoylmethylthio)penem-3-carboxylate (Compound No. 89)

Following the procedure of Example 17, but replacing the methylamine by a solution of hydroxylamine in methanol, 41 mg of the desired product were obtained from p-nitrobenzyl 2-(4-methylthio-2-azetidinon-1-yl)-2-(4-oxo-1,3-dithiolan-2-ylidene)acetate (200 mg, 0.468 mmole).

Infrared Absorption Spectrum (KBr) $\nu_{max}$ cm$^{-1}$: 3440, 3250, 1780, 1670, 1637.

Nuclear Magnetic Resonance Spectrum (heptadeuterated dimethylformamide) δ ppm: 3.10–4.14 (4H, multiplet); 5.25, 5.41 (2H, AB-quartet, J=14.7 Hz); 5.77 (1H, doubled doublet); 7.72, 8.24 (4H, A$_2$B$_2$, J=11.7 Hz); 9.30 (1H, broad singlet); 10.84 (1H, broad singlet).

EXAMPLE 27 p-Nitrobenzyl 2-(N-methoxycarbamoylmethylthio)penem-3-carboxylate (Compound No. 90)

Following the procedure of Example 17, but replacing the methylamine by a solution of O-methylhydroxylamine in methanol, 44 mg of the desired product were obtained from p-nitrobenzyl 2-(4-methylthio-2-azetidinon-1-yl)-2-(4-oxo-1,3-dithiolan-2-ylidene)acetate (110 mg, 0.258 mmole).

Mass Spectrum m/e: 425 (M+).

Infrared Absorption Spectrum (CHCl$_3$) $\nu_{max}$ cm$^{-1}$: 3380, 1795, 1695, 1640.

Nuclear Magnetic Resonance Spectrum (heptadeuterated dimethylformamide) δ ppm: 3.53 (1H, doubled doublet, J=16.8 and 2.0 Hz); 3.72 (3H, singlet); 3.85 (2H, multiplet); 3.91 (1H, doubled doublet, J=16.8 and 4.0 Hz); 5.38, 5.56 (2H, AB-quartet, J=13.2 Hz); 5.90 (1H, doubled doublet, J=4.0 and 2.0 Hz); 7.80, 8.28 (4H, A$_2$B$_2$, J=7.5 Hz); 8.85 (1H, broad singlet).

EXAMPLE 28 p-Nitrobenzyl 2-(2-carbamoylethylthio)penem-3-carboxylate (Compound No. 91)

Following the procedure of Example 16, p-nitrobenzyl 2-(4-methylthio-2-azetidinon-1-yl)-2-(4-oxo-1,3-dithian-2-ylidene)acetate (91 mg, 0.207 mmole) was reacted with excess ammonia to give 15 mg of the desired product.

Infrared Absorption Spectrum (KBr) $\nu_{max}$ cm$^{-1}$: 3370, 3180, 1795, 1688, 1650.

Nuclear Magnetic Resonance Spectrum (heptadeuterated dimethylformamide) δ ppm: 3.10–4.15 (6H, multiplet); 5.92 (1H, doubled doublet, J=4.0 and 2.0 Hz); 5.27, 5.51 (2H, AB-quartet, J=13.8 Hz); 7.00 (2H, broad singlet); 7.84, 8.33 (4H, A$_2$B$_2$, J=8.7 Hz).

EXAMPLE 29 p-Nitrobenzyl 2-(p-nitrobenzyloxycarbonylmethylthio)penem-3-carboxylate (Compound No. 92)

Following the procedure of Example 17, p-nitrobenzyl 2-(4-methylthio-2-azetidinon-1-yl)-2-(4-oxo-1,3-dithiolan-2-ylidene)acetate (150 mg, 0.234 mmole) was reacted with chlorine to give the crude 4-chloroazetidinone compound. This compound was dissolved in methylene chloride (1.5 ml). To the solution were added, with ice cooling, p-nitrobenzyl alcohol (35.8 mg, 0.234 mmole) and triethylamine (35.4 mg, 0.351 mmole), after which the mixture was stirred for 1.5 hours. After completion of the reaction, the reaction mixture was washed successively with water and a saturated aqueous solution of sodium chloride. It was then dried over anhydrous sodium sulphate. The solvent was distilled off under reduced pressure and the residue was purified by column chromatography (eluent: a 4:1 by volume mixture of benzene and ethyl acetate) to give 25 mg of the desired product.

Infrared Absorption Spectrum (CHCl$_3$) $\nu_{max}$ cm$^{-1}$: 1788, 1740, 1690.

Nuclear Magnetic Resonance Spectrum (CDCl$_3$) δ ppm: 3.80 (2H, singlet); 3.49 (1H, doubled doublet, J=16.5 and 2.0 Hz); 3.81 (1H, doubled doublet, J=16.5 and 4.0 Hz); 5.29 (2H, singlet); 5.23, 5.43 (2H, AB-quartet, J=13.8 Hz); 5.70 (1H, doubled doublet, J=4.0 and 2.0 Hz); 7.54, 8.22 (4H, A$_2$B$_2$, J=9.6 Hz).

EXAMPLE 30 p-Nitrobenzyl(5S,6S)-6-[1-(R)-t-butyldimethylsilyloxyethyl]-2-(N-methylcarbamoylmethylthio)penem-3-carboxylate (Compound NO. 93)

All of the p-nitrobenzyl 2-[3-(1-t-butyldimethylsilyloxyethyl)-4-chloro-2-azetidinon-1-yl]-2-(4-oxo-1,3-dithiolan-2-ylidene)acetate obtained in Preparation 21 was dissolved in methylene chloride (3 ml). To the solution were added a 30% solution of methylamine in methanol (27 μl) and a solution of triethylamine (28 μl) in methylene chloride (0.5 ml), with ice cooling, after which the mixture was stirred at that temperature for 20 minutes. After the solvent had been distilled off under reduced pressure, ethyl acetate was added to the residue. The resulting solution was washed with a saturated aqueous solution of sodium chloride and dried over magnesium sulphate. After the solvent had been distilled off, the resulting residue was purified by column chromatography through silica gel. There were obtained 104 mg of the desired product from fractions eluted with a 4:1 by volume mixture of methylene chloride and ethyl acetate.

Infrared Absorption Spectrum (KBr) $\nu_{max}$ cm$^{-1}$: 3300, 1785, 1700, 1680.

Ultraviolet Absorption Spectrum (ethanol) $\lambda_{max}$ nm (ε): 261 (16150), 336 (10480).

Nuclear Magnetic Resonance Spectrum (CDCl$_3$) Δ ppm: 0.09 (6H, singlet); 0.80 (9H, singlet); 1.36 (3H, doublet, J=5.8 Hz); 2.80 (3H, doublet, J=5.0 Hz); 3.70 (2H, singlet); 3.88 (1H, doubled doublet, J=4.0 and 10.5 Hz); 4.1–4.6 (1H, multiplet); 5.19, 5.49 (2H, AB-quartet, J=14.5 Hz); 5.73 (1H, doublet, J=4.0 Hz); 6.72 (1H, broad singlet); 7.64, 8.25 (4H, A$_2$B$_2$, J=8.2 Hz).

EXAMPLE 31 p-Nitrobenzyl(5R,6S)-6-[1-(R)-t-butyldimethylsilyloxyethyl]-2-(N-methylcarbamoylethylthio)penem-3-carboxylate (Compound No. 93)

p-Nitrobenzyl(5S,6S)-6-[1-(R)-t-butyldimethylsilyloxyethyl]-2-(N-methylcarbamoylmethylthio)-penem-3-carboxylate was dissolved in xylene (30 ml), and hydroquinone (14 mg) was added thereto. The mixture was then heated on an oil bath at 125° C. under a stream of nitrogen for 4 hours. The solvent was distilled off under reduced pressure and the resulting residue was purified by column chromatography through silica gel. 54 mg of the desired product were obtained from fractions eluted with a 1:1 by volume mixture of benzene and ethyl acetate. 25 mg of the original (5S,6S)-6-[1-(R)] compound were also recovered.

Nuclear Magnetic Resonance Spectrum (CDCl$_3$) δ ppm: 0.03 (3H, singlet); 0.06 (3H, singlet); 0.08 (9H, singlet); 1.19 (3H, doublet, J=6.0 Hz); 2.78 (3H, doublet, J=5.0 Hz); 3.57 (2H, singlet); 3.65 (1H, doubled doublet, J=1.8 and 4.2 Hz); 3.8–4.4 (1H, multiplet); 5.10, 5.33 (2H, AB-quartet, J=14,0 Hz); 5.58 (1H, doublet, J=1.8 Hz); 6.52 (1H, broad singlet); 7.50, 8.08 (4H, A$_2$B$_2$, J=9.0 Hz).

EXAMPLE 32 p-Nitrobenzyl(5R,6S)-6-[1-(R)-hydroxyethyl]-2-(N-methylcarbamoylmethylthio)penem-3-carboxylate (Compound No. 94)

Acetic acid (60 μl) and tetrabutylammonium fluoride (158 mg) were added to a solution of p-nitrobenzyl(5R,6S)-6-[1-(R)-t-butyldimethylsilyloxyethyl]-2-(N-methylcarbamoyl-methylthio)penem-3-carboxylate (54 mg) in tetrahydrofuran (1.5 ml), after which the mixture was stirred at room temperature for 52 hours. The reaction mixture was then diluted with ethyl acetate, washed successively with a saturated aqueous solution of sodium chloride, a 5% w/v aqueous solution of sodium bicarbonate and a saturated aqueous solution of sodium chloride. The solvent was distilled off to give 39 mg of the desired product as crystals.

Nuclear Magnetic Resonance Spectrum (heptadeuterated dimethylformamide) δ ppm: 1.26 (3H, doublet, J=5.8 Hz); 2.69 (3H, doublet, J=5,0 Hz); 3.43 (1H, broad singlet); 3.83 (1H, doubled doublet, J=1.8 and 5.0 Hz); 3.84 (2H, singlet); 3.6–4.2 (1H, multiplet); 5.30 (1H, broad singlet); 5.32, 5.50 (2H, AB-quartet, J=14.0 Hz); 5.80 (1H, doublet, J=1.8 Hz); 7.73, 8.19 (4H, A$_2$B$_2$, J=9.0 Hz).

Infrared Absorption Spectrum (KBr) ν$_{max}$ cm$^{-1}$: 3430, 3300, 1768, 1685, 1653.

Ultraviolet Absorption Spectrum (ethanol) λ$_{max}$ nm (ε): 262 (16390), 340 (10610).

EXAMPLE 33 p-Nitrobenzyl(5S,6S)-6-[1-(R)-t-butyldimethylsilyloxyethyl]-2-carbamoylmethylthiopenem-3-carboxylate (Compound No. 58) and
p-nitrobenzyl(5S,6S)-6-[1-(R)-t-butyldimethylsilyloxyethyl]-2-methoxycarbonylmethylthiopenem-3-carboxylate (Compound No. 95)

Following the procedures of, in turn, Preparation 21 and Example 30, p-nitrobenzyl 2-[3-(1-t-butyldimethylsilyloxyethyl)-4-methylthio-2-azetidinon-1-yl]-2-(4-oxo-1,3-dithiolan-2-ylidene)acetate (292 mg) was subjected to chlorination using an equimolar amount of chlorine and the resulting compound was treated with a mixture of a solution of ammonia in methanol and triethylamine, the molar ratio ammonia:triethylamine:chlorinated compound being 1.1:1.1:1. The resulting crude product was purified by column chromatography through silica gel. 101 mg of the desired methyl ester (Compound No. 95) were obtained from fractions eluted with a 20:1 by volume mixture of benzene and ethyl acetate.

Nuclear Magnetic Resonance Spectrum (CDCl$_3$) δ ppm: 0.12 (6H, singlet); 0.85 (9H, singlet); 1.41 (3H, doublet, J=5.8 Hz); 3.73 (5H, singlet); 3.82 (1H, doubled doublet, J=4.0 and 10.0 Hz); 4.1–4.5 (1H, multiplet); 5.20, 5.42 (2H, AB-quartet, J=14.0 Hz); 5.68 (1H, doublet, J=4.0 Hz); 7.53, 8.13 (4H, A$_2$B$_2$, J=9.0 Hz).

Infrared Absorption Spectrum (CHCl$_3$) ν$_{max}$ cm$^{-1}$: 1795, 1750, 1700.

Ultraviolet Absorption Spectrum (ethanol) λ$_{max}$ nm (ε): 262 (15850), 336 (9710).

102 mg of the desired amide compound (Compound No. 58) were obtained from fractions eluted with a 2:1 by volume mixture of benzene and ethyl acetate.

Nuclear Magnetic Resonance Spectrum (CDCl$_3$) δ ppm: 0.12 (6H, singlet); 0.88 (9H, singlet); 1.40 (3H, doublet, J=6.0 Hz); 3.66 (2H, singlet); 3.86 (1H, doubled doublet, J=4.0 and 10.0 Hz); 4.0–4.6 (1H, multiplet); 5.18, 5.49 (2H, AB-quartet, J=14.0 Hz); 5.70 (1H, doublet, J=4.0 Hz); 6.34 (1H, broad singlet); 7.55, 8.15 (4H, A$_2$B$_2$, J=8.0 Hz).

Infrared Absorption Spectrum (CHCl$_3$) ν$_{max}$ cm$^{-1}$: 3500, 3400, 1790, 1700, 1690.

Ultraviolet Absorption Spectrum (ethanol) λ$_{max}$ nm (ε): 261 (15880), 337 (10190).

EXAMPLE 34 p-Nitrobenzyl(5R,6S)-6-[1-(R)-t-butyldimethylsilyloxyethyl]-2-carbamoylmethylthiopenem-3-carboxylate (Compound No. 58)

Following the procedure of Example 31, 70 mg of the desired product were obtained from p-nitrobenzyl(5S,6S)-6-[1-(R)-t-butyldimethylsilyloxyethyl]-2-carbamoylmethyl-thiopenem-3-carboxylate (95 mg).

Nuclear Magnetic Resonance Spectrum (CDCl$_3$) δ ppm: 0.02 (3H, singlet); 0.06 (3H, singlet); 0.83 (9H, singlet); 1.23 (3H, doublet, J=6.2 Hz); 3.62 (2H, singlet); 3.72 (1H, doubled doublet, J=1.6 and 3.8 Hz); 4.0–4.4 (1H, multiplet); 5.17, 5.39 (2H, AB-quartet, J=14.0 Hz); 5.63 (1H, doublet, J=1.6 Hz); 6.47 (2H, broad singlet); 7.55, 8.12 (4H, A$_2$B$_2$, J=9.0 Hz), Infrared Absorption Spectrum (CHCl$_3$) ν$_{max}$ cm$^{-1}$: 3510, 3400, 1785, 1700, 1685.

EXAMPLE 35 p-Nitrobenzyl(5R,6S)-6[1-(R)-t-butyldimethylsilyloxyethyl]-2-methoxycarbonylmethylthiopenem-3-carboxylate (Compound No. 95)

Following the procedure of Example 31, 57 mg of the desired product were obtained from p-nitrobenzyl(5S,6S)-6-[1-(R)-t-butyldimethylsilyloxyethyl]-2-methoxycarbonylmetmethylthiopenem-3-carboxylate (91 mg).

Nuclear Magnetic Resonance Spectrum (CDCl$_3$) δ ppm: 0.04 (3H, singlet); 0.07 (3H, singlet); 1.18 (3H, doublet, J=6.0 Hz); 3.70 (1H, doubled doublet, J=1.8 and 3.0 Hz); 3.73 (5H, singlet); 4.05–4.45 (1H, multiplet); 5.21, 5.43 (2H, AB-quartet, J=14.0 Hz); 5.68 (1H, doublet, J=1.8 Hz); 7.65, 8.24 (4H, A$_2$B$_2$, J=9.5 Hz).

Infrared Absorption Spectrum (CHCl$_3$) ν$_{max}$ cm$^{-1}$: 1796, 1750, 1700.

EXAMPLE 36 p-Nitrobenzyl(5R,6S)-2-carbamoylmethylthio-6-[1-(R)-hydroxyethyl]penem-3-carboxylate (Compound No. 96)

Following the procedure of Example 32, 40 mg of the desired product were obtained from p-nitrobenzyl(5R,6S)-6-[1-(R)-t-butyldimethylsilyloxyethyl]-2-carbamoylmethylthiopenem-3-carboxylate (54 mg).

Nuclear Magnetic Resonance Spectrum (heptadeuterated dimethylformamide) δ ppm: 1.28 (3H, doublet, J=6.0 Hz); 3.45 (1H, broad singlet); 3.84 (1H, doubled doublet, J=1.8 and 4.0 Hz); 3.89 (2H, singlet); 3.9–4.3 (1H, multiplet); 5.29, 5.49 (2H, AB-quartet, J=14.0 Hz); 5.81 (1H, doublet, J=1.8 Hz); 7.3 (2H, broad singlet); 7.72, 8.18 (4H, $A_2B_2$).

Infrared Absorption Spectrum (KBr) $\nu_{max}$ cm$^{-1}$: 3430, 3300, 1770, 1680, 1665.

Ultraviolet Absorption Spectrum (ethanol) $\nu_{max}$ nm: 262, 340.

EXAMPLE 37 p-Nitrobenzyl 6-methoxy-2-(2-oxopropylthio)penem-3-carboxylate (Compound No. 97)

Following the procedure of Example 12, but using p-nitrobenzyl 2-(4-hydroxy-4-methyl-1,3-dithiolan-2-ylidene)-2-(3-methoxy-4-methylthio-2-azetidinon-1-yl)acetate (61 mg), sulphuryl chloride (11 μl) and triethylamine (182 μl) and purifying the resulting product by preparative thin layer chromatography (eluent: a 1:2 by volume mixture of cyclohexane and ethyl acetate), there was obtained the desired product.

Nuclear Magnetic Resonance Spectrum (CDCl$_3$) δ ppm: 2.25 (3H, singlet); 3.58 (3H, singlet); 3.86 (2H, singlet); 5.16 (1H, doublet, J=3.5 Hz); 5.25, 5.48 (2H, AB-quartet, J=14.0 Hz); 5.72 (1H, doublet, J=3.5 Hz); 7.62, 8.27 (4H, $A_2B_2$, J=9.5 Hz).

Infrared Absorption Spectrum (CHCl$_3$) $\nu_{max}$ cm$^{-1}$: 1800, 1720, 1700.

Ultraviolet Absorption Spectrum (ethanol) $\lambda_{max}$ nm: 265, 337.

EXAMPLE 38 p-Nitrobenzyl(5R,6S)-6-[1-(R)-hydroxyethyl]-2-methoxycarbonylmethylthiopenem-3-carboxylate (Compound No. 98)

Following the procedure of Example 32, but using p-nitrobenzyl(5R,6S)-6-[1-(R)-t-butyldimethylsilyloxyethyl]-2-methoxycarbonylmethylthiopenem-3-carboxylate (57 mg), tetrabutylammonium fluoride (158 mg) and acetic acid (60 μl), there were obtained 46 mg of the desired product.

Nuclear Magnetic Resonance Spectrum (heptadeuterated dimethylformamide) δ ppm: 1.28 (3H, doublet, J=5.8 Hz); 3.62 (3H, singlet); 3.5 (1H, broad singlet); 3.8–4.3 (1H, multiplet); 3.90 (1H, doubled doublet, J=1.8 and 5.5 Hz); 4.03 (2H, singlet, CH$_2$CO); 5.29, 5.55 (2H, AB-quartet, J=14.0 Hz); 5.83 (1H, doublet, J=1.8 Hz); 7.74, 8.19 (4H, $A_2B_2$, J=8.2 Hz).

Infrared Absorption Spectrum (KBr) $\nu_{max}$ cm$^{-1}$: 3540, 1800, 1742, 1670.

EXAMPLE 39 p-Nitrobenzyl 6-methoxy-2-(N-methylcarbamoylmethylthio)penem-3-carboxylate (Compound No. 99)

Following the procedure of Example 17, but using p-nitrobenzyl 2-(3-methoxy-4-methylthio-2-azetidinon-1-yl)-2-(4-oxo-1,3-dithiolan-2-ylidene)acetate (108 mg), a solution of chlorine in carbon tetrachloride in an amount of 2 moles of chlorine per mole of azetidinone, 25 μl of a 30% solution of methylamine in methanol and triethylamine (33.3 μl), there were obtained 14 mg of the desired product as a powder.

Infrared Absorption Spectrum (methylene chloride) $\nu_{max}$ cm$^{-1}$: 1800, 1710, 1680.

EXAMPLE 40

Sodium 2-(carbamoylmethylthio)penem-3-carboxylate (Sodium salt of Compound No. 30)

p-Nitrobenzyl 2-(carbamoylmethylthio)penem-3-carboxylate (17 mg., 0.043 mmole) was dissolved in a mixture of tetrahydrofuran (6 ml.) and a phosphate buffer solution (pH 7.10, 4 ml.) and a 10% w/w palladium on charcoal catalyst (50 mg.) was suspended therein. The mixture was contacted with hydrogen gas for 2 hours. After completion of the reaction, the catalyst was filtered off using a Celite (Trade Mark) filter aid under reduced pressure and the filtrate was extracted and washed with ethyl acetate. Water was distilled off to give 1 ml. of a mixture residue, which was purified by chromatography through a Diaion HP-20AG resin (a product of Mitsubishi Chemical Industries, Ltd., 100–200 mesh) to afford 4.2 mg. of the desired product.

Infrared Absorption Spectrum (KBr) $\nu_{max}$cm$^{-1}$: 3400, 1760, 1668, 1580.

Nuclear Magnetic Resonance Spectrum (D$_2$O) δ ppm: 3.52 (1H, doubled doublet, J=17.0 and 2.0 Hz); 3.80 (1H, doubled doublet, J=17.0 and 4.0 Hz); 5.75 (1H, doubled doublet, J=4.0 and 2.0 Hz); 3.71 (2H, singlet);

EXAMPLE 41

Sodium 2-(N,N-diethylcarbamoylmethylthio)penem-3-carboxylate (Sodium salt of Compound No. 33)

Following the procedure of Example 40, 4.8 mg. of the desired product were obtained from p-nitrobenzyl 2-(N,N-diethylcarbamoylmethylthio)penem-3-carboxylate (13 mg., 0.0288 mmole).

Infrared Absorption Spectrum (KBr) $\nu_{max}$ cm$^{-1}$: 1765, 1620, 1590.

Nuclear Magnetic Resonance Spectrum (D$_2$O) δ ppm: 1.11 (3H, triplet, J=7.0 Hz); 1.21 (3H, triplet, J=7.0 Hz); 3.38 (4H, quartet, J=7.0 Hz); 3.51 (1H, doubled doublet, J=15.5 and 2.0 Hz); 3.80 (1H, doubled doublet, J=15.5 and 4.0 Hz); 3.95 (2H, doublet); 5.73 (1H, doubled doublet, J=4.0 and 2.0 Hz).

EXAMPLE 42

Sodium 2-(2-morpholino-2-oxoethylthio)penem-3-carboxylate (Sodium salt of Compound No. 38)

Following the procedure of Example 40, there was obtained 16 mg. of the desired product from p-nitrobenzyl 2-(2-morpholino-2-oxoethylthio)penem-3-carboxylate (26 mg., 0.0559 mmole).

Ultraviolet Absorption Spectrum (H$_2$O)$\lambda_{max}$ nm ($\epsilon$): 250 (4790), 322 (6120).

Infrared Absorption Spectrum (KBr) $\nu_{max}$ cm$^{-1}$: 1770, 1638, 1600.

Nuclear Magnetic Resonance Spectrum (D$_2$O) δ ppm: 4.32–3.92 (10H, multiplet); 3.99 (2H, doublet); 5.75 (1H, doubled doublet, J=4.0 and 2.0 Hz).

EXAMPLE 43

2-[2-Oxo-2-(1-piperazinyl)ethylthio)]penem-3-carboxylic acid (Sodium salt of Compound No. 36)

Following the procedure of Example 40, there were obtained 8 mg. of the desired product from p-nitrobenzyl 2-[2-(4-p-nitrobenzyloxycarbonyl-1-piperazinyl)-2-oxoethylthio]penem-3-carboxylate (68 mg., 0.106 mmole).

Nuclear Magnetic Resonance Spectrum ($D_2O$) δ ppm: 3.18–3.95 (10H, multiplet); 3.98 (2H, doublet); 5.76 (1H, doubled doublet, J=4.0 and 2.0 Hz).

EXAMPLE 44

Sodium 2-(2-carbamoylethylthio)penem-3-carboxylate
(Sodium salt of Compound No. 31)

Following the procedure of Example 40, there were obtained 5.5 mg. of the desired product from p-nitrobenzyl 2-(2-carbamoylethylthio)penem-3-carboxylate (20 mg., 0.0488 mmole).

Infrared Absorption Spectrum (KBr)$\nu_{max}$ cm$^{-1}$: 3420 (broad), 1760, 1660, 1580.

Nuclear Magnetic Resonance Spectrum ($D_2O$) δ ppm: 2.63 (2H, triplet, J=7.0 Hz); 3.06 (2H, triplet, J=7.0 Hz); 3.47 (1H, doubled doublet, J=17.0 and 2.0 Hz); 3.73 (1H, doubled doublet, J=17.0 and 4.0 Hz); 5.63 (1H, doubled doublet, J=4.0 and 2.0 Hz);

EXAMPLE 45

Sodium
(5R,6S)-2-carbamoylmethylthio-6-[1-(R)-hydroxyethyl]penem-3-carboxylate (Sodium salt of Compound No. 53)

Following the procedure of Example 40, there were obtained 12 mg of the desired product from p-nitrobenzyl (5R,6S)-2-carbamoylmethylthio-6-[1-(R)-hydroxyethyl]penem-3-carboxylate (29 mg).

Nuclear Magnetic Resonance Spectrum ($D_2O$) δ ppm: 1.29 (3H, doublet, J=7.0 Hz); 3.73 (2H, singlet); 3.92 (1H, doubled doublet, J=1.5 and 6.0 Hz); 4.0–4.6 (1H, multiplet); 5.71 (1H, doublet, J=1.5 Hz);

Infrared Absorption Spectrum (KBr) $\nu_{max}$ cm$^{-1}$: 3400, 1770, 1675.

Ultraviolet Absorption Spectrum ($H_2O$) $\lambda_{max}$ nm (ε): 249 (4900), 322 (6380).

EXAMPLE 46

Sodium
(5R,6S)-6-[1-(R)-hydroxyethyl]-2-(N-methylcarbamoylmethylthio)penem-3-carboxylate (Sodium salt of Compound No. 54)

Following the procedure of Example 40, there were obtained 12 mg of the desired product from p-nitrobenzyl (5R,6S)-6-[1-(R)-hydroxyethyl]-2-(N-methylcarbamoylmethylthio)penem-3-carboxylate (35 mg).

Ultraviolet Absorption Spectrum ($H_2O$) $\lambda_{max}$ nm (ε): 249 (4930), 322 (6550).

EXAMPLE 47 p-Nitrobenzyl
(5S,6S)-6-[1-(R)-t-butyldimethylsilyloxyethyl]-2-(1-carbamoylethylthio)penem-3-carboxylate, a mixture of isomers A and B (Compound No. 73)

An equimolar amount of chlorine was added to a solution of p-nitrobenzyl 2-[3-(1-t-butyldimethylsilyloxyethyl)-4-methylthio-2-azetidinon-1-yl]-2-(5-methyl-4-oxo-1,3-dithiolan-2-ylidene) acetate (228 mg.) in methylene chloride (4 ml.). To the resulting solution was added a mixture of an isopropanol solution containing an excess of ammonia with an equimolar amount of triethylamine, and then the mixture was stirred whilst cooling. The resulting crude product was purified by silica gel chromatography eluted with a 1:1 by volume mixture of benzene and ethyl acetate, to give the desired product (isomer A 20 mg., isomer B, 13 mg.).

Isomer A

Infrared Absorption Spectrum ($CHCl_3$)$\nu_{max}$ cm$^{-1}$:

Nuclear Magnetic Resonance Spectrum ($CDCl_3$) δ ppm: 0.12 (6H singlet); 0.84 (9H, singlet); 1.33 (3H, doublet, J=5.8 Hz); 1.54 (3H, doublet, J=6.5 Hz); 3.75 (1H, doubled doublet, J=10.0 and 4.0 Hz); 3.82 (1H, quartet, J=6.5 Hz); 3.98–4.47 (1H, multiplet); 5.11, 5.37 (2H, AB-quartet, J=14.4 Hz); 5.63 (1H, doublet, J=4.0 Hz); 6.05 (2H, broad singlet); 7.53, 8.15 (4H, $A_2B_2$, J=9.0 Hz).

Isomer B

Infrared Absorption Spectrum ($CHCl_3$)$\nu$ cm$^{-1}$: 3520, 3400, 1782, 1688.

Nuclear Magnetic Resonance Spectrum ($CDCl_3$) δ ppm: 0.13 (6H, singlet); 0.84 (9H, singlet); 1.36 (3H, doublet, J=5.5 Hz); 1.54 (3H, doublet, J=7.0 Hz); 3.74 (1H, doubled doublet, J=10.0 and 4.0 Hz); 3.77 (1H, quartet, J=7.0 Hz); 3.98–4.48 (1H, multiplet); 5.09, 5.35 (2H, AB-quartet, J=14.4 Hz); 5.60 (1H, doublet, J=4.0 Hz); 6.24 (2H, broad singlet); 7.53, 8.13 (4H, $A_2B_2$, J=9.3 Hz).

EXAMPLE 48 p-Nitrobenzyl
(5R,6S)-6-[1-(R)-t-butyldimethylsilyloxyethyl]-2-(1-carbamoylethylthio)penem-3-carboxylate, Isomer A (Compound No. 73)

Isomer A of p-nitrobenzyl (5S,6S)-6-[1-(R)-t-butyldimethylsilyloxyethyl]-2-(1-carbamoylethylthio)-penem-3-carboxylate (51 mg.) was dissolved in xylene (5 ml.), and hydroquinone (2.5 mg.) was added thereto, after which the mixture was heated at 140° C. on an oil bath, with stirring, for 1 hour under a stream of nitrogen. The solvent was distilled off under reduced pressure and the residue was purified by silica gel chromatography eluted with a 1:1 by volume mixture of benzene and ethyl acetate, to give the desired product and some unchanged starting material. The recovered starting material was further heated to afford more of the desired product. The total yield was 36 mg.

Infrared Absorption Spectrum ($CHCl_3$)$\nu_{max}$ cm$^{-1}$: 3520, 3400, 1785, 1685.

Nuclear Magnetic Resonance Spectrum ($CDCl_3$) δ ppm: 0.03 (3H, singlet); 0.08 (3H, singlet); 0.78 (9H, singlet); 1.15 (3H, doublet, J=6.0 Hz); 1.52 (3H, doublet, J=7.0 Hz); 3.71 (1H doubled doublet, J=4.0 and 1.8 Hz); 3.85 (1H, quartet, J=7.0 Hz); 4.0–4.4 (1H, multiplet); 5.16–5.38 (2H, AB-quartet, J=13.5 Hz); 5.64 (1H, doublet, J=1.8 Hz); 6.40 (2H, broad singlet); 7.62, 8.20 (4H, $A_2B_2$, J=8.7 Hz).

EXAMPLE 49 p-Nitrobenzyl
(5R,6S)-6-[1-(R)-t-butyldimethylsilyloxyethyl]-2-(1-carbamoylethylthio)penem-3-carboxylate, Isomer B (Compound No. 73)

Following the procedure described in Example 48, isomer B of p-nitrobenzyl (5S,6S)-6-[1-(R)-t-butyldimethylsilyloxyethyl]-2-(1-carbomylethylthio)penem-3-carboxylate (60 mg.) was heated in xylene to afford 39 mg. of the desired product.

Infrared Absorption Spectrum (CHCl$_3$)$\nu_{max}$ cm$^{-1}$: 3520, 3400, 1785, 1685.

Nuclear Magnetic Resonance Spectrum (CDCl$_3$) δ ppm: 0.04 (3H, singlet); 0.07 (3H, singlet); 0.83 (9H, singlet); 1.22 (3H, doublet, J=5.8 Hz); 1.60 (3H, doublet, J=7.2 Hz); 3.78 (1H, doubled doublet, J=4.0 and 1.8 Hz); 3.92 (1H, quartet, J=7.2 Hz); 4.1–4.5 (1H, multiplet); 5.25–5.47 (2H, AB-quartet, J=13.8 Hz); 5.73 (1H, doublet, J=1.8 Hz); 6.44 (2H, broad singlet); 7.73, 8.33 (4H, A$_2$B$_2$, J=8.1 Hz).

EXAMPLE 50 p-Nitrobenzyl (5R,6S)-2-(1-carbamoylethylthio)-6-[1-(R)-hydroxyethyl]penem-3-carboxylate, Isomer A (Compound No. 77)

To a solution of isomer A of p-nitrobenzyl (5R,6S)-6-[1-(R)-t-butyldimethylsilyloxyethyl]-2-(1-carbamoylethylthio)penem-3-carboxylate (35 mg.) in tetrahydrofuran (1 ml.) were added acetic acid (38.9 μl.) and tetrabutylammonium fluoride (102 mg.). The mixture was left to stand at room temperature for 2 days. The reaction mixture was then diluted with ethyl acetate, washed successively with a saturated aqueous solution of sodium chloride, a 5% w/v aqueous solution of sodium bicarbonate and again a saturated aqueous solution of sodium chloride. The solvent was then distilled off and the resulting residue was purified by silica gel chromatography eluted with a 10.1 by volume mixture of chloroform and methanol, to give 20 mg. of the desired product.

Infrared Absorption Spectrum (KBr)$\nu_{max}$ cm$^{-1}$: 3420, 1780, 1673, 1655.

Nuclear Magnetic Resonance Spectrum (heptadeuterated dimethylformamide) δ ppm: 1.20 (3H, doublet, J=5.0 Hz); 1.48 (3H, doublet, J=6.5 Hz); 3.63–4.43 (3H, multiplet); 5.22, 5.40 (2H, AB-quartet, J=14.1 Hz); 5.70 (1H, doublet, J=1.5 Hz); 7.03–7.25 (2H, broad singlet); 7.68, 8.15 (4H, A$_2$B$_2$, J=8.7 Hz).

EXAMPLE 51 p-Nitrobenzyl (5R,6S)-2-(1-carbamoylethylthio)-6-[1-(R)-hydroxyethyl]penem-3-carboxylate, Isomer B (Compound No. 77)

Following the procedure described in Example 50, isomer B of p-nitrobenzyl (5R,6S)-6-[1-(R)-t-butyldimethylsilyloxyethyl]-2-(1-carbamoylethylthio)penem-3-carboxylate (38 mg.) was used to afford 20 mg. of the desired product.

Infrared Absorption Spectrum (KBr)$\nu_{max}$ cm$^{-1}$: 3430, 1788, 1685, 1655.

Nuclear Magnetic Resonance Spectrum (heptadeuterated dimethylformamide) δ: 1.25 (3H, doublet, J=5.5 Hz); 1.58 (3H, doublet, J=7.5 Hz); 3.62–4.30 (3H, multiplet); 5.24, 5.45 (2H, AB-quartet, J=13.8 Hz); 5.78 (1H, doublet, J=1.5 Hz), 7.06–7.38 (2H, broad singlet); 7.75, 8.21 (2H, A$_2$B$_2$, J=8.70 Hz).

EXAMPLE 52

Sodium (5R,6S)-2-(1-carbamoylethylthio)-6-[1-(R)-hydroxyethyl]penem-3-carboxylate, Isomer A (Sodium salt of Compound No. 65)

Isomer A of p-nitrobenzyl (5R,6S)-(1-carbamoylethylthio)-6-[1-(R)-hydroxyethyl]penem-3-carboxylate (20 mg.) was dissolved in a mixture of tetrahydrofuran (4 ml.) and a phosphate buffer solution (pH 7.10, 4 ml.). A 10% w/w palladium on charcoal catalyst (38 mg.) was suspended in the above solution. The resulting mixture was contacted with hydrogen gas for 1.5 hours. The catalyst was filtered off under reduced pressure using a Celite (Trade Mark) filter aid. The filtrate was extracted and washed with ethyl acetate. The water was then distilled off to give about 1 ml. of a mixture, which was purified by chromatography through a Diaion HP-20AG resin (a product of Mitsubishi Chemical Industries Ltd., 100–200 mesh) to afford 10 mg. of the desired compound.

Infrared Absorption Spectrum (KBr)$\nu_{max}$ cm$^{-1}$: 3400, 1760, 1670, 1585.

Nuclear Magnetic Resonance Spectrum (D$_2$O) δ ppm: 1.30 (3H, doublet, J=6.0 Hz); 1.51 (3H, doublet, J=7.0 Hz); 3.93 (1H, doubled doublet, J=6.0 and 1.5 Hz); 4.02 (1H, quartet, J=7.0 Hz); 4.15–4.4 (1H, multiplet); 5.68 (1H, doublet, J=1.5 Hz).

EXAMPLE 53

Sodium (5R,6S)-2-(1-carbamoylethylthio)-6-[1-(R)-hydroxyethyl]penem-3-carboxylate, Isomer B (Sodium salt of Compound No. 65)

Following the procedure described in Example 50, isomer B of p-nitrobenzyl (5R,6S)-2-(1-carbamoylethylthio)-6-[1-(R)-hydroxyethyl]penem-3-carboxylate (20 mg.) was used to afford 10 mg. of the desired product.

Infrared Absorption Spectrum $\nu_{max}$ KBr cm$^{-1}$: 3400, 1760, 1670, 1585.

Nuclear Magnetic Resonance Spectrum (D$_2$O) δ ppm: 1.29 (3H, doublet, J=6.0 Hz); 1.54 (3H, doublet, J=7.0 Hz); 3.91 (1H, doubled doublet, J=6.0 and 1.5 Hz); 4.01 (1H, quartet, J=7.0 Hz); 4.15–4.40 (1H, multiplet); 5.69 (1H, doublet, J=1.5 Hz).

EXAMPLE 54 p-Nitrobenzyl (5S,6S)-6-[1-(R)-t-butyldimethylsilyloxyethyl]-2-(1-carbamoylpropylthio)penem-3-carboxylate, Isomers A and B (Compound No. 75)

p-Nitrobenzyl 2-[3-(1-t-butyldimethylsilyloxyethyl)-4-methylthio-2-azetidinon-1-yl]-2-(5-ethyl-4-oxo-1,3-dithiolan-2-ylidene)acetate (340 mg) was treated with sulphuryl chloride (46 ml.), and then with excess ammonia. The reaction mixture was then purified by Lobar column chromatography (eluent: a 2:1 by volume mixture of benzene and ethyl acetate), giving 90 mg of Isomer A and 124 mg of Isomer B.

Isomer A

Nuclear Magnetic Resonance Spectrum (CDCl$_3$) δ ppm: 0.12 (6H, singlet); 0.88 (9H, singlet); 1.09 (3H, triplet, J=7.5 Hz); 1.43 (3H, doublet, J=6.0 Hz); 1.7–2.2 (2H, multiplet); 3.80 (1H, triplet, J=7.0 Hz); 3.88 (1H, doubled doublet, J=4.0 and 10.0 Hz); 4.1–4.6 (1H, multiplet); 5.18, 5.47 (2H, AB-quartet, J=14.0 Hz); 5.70 (1H, doublet, J=4.0 Hz); 6.35 (2H, broad singlet); 7.61, 8.18 (4H, A$_2$B$_2$, J=9.0 Hz).

Infrared Absorption Spectrum (CHCl$_3$)$\nu_{max}$ cm$^{-1}$: 3510, 3400, 1785, 1695.

Isomer B

Nuclear Magnetic Resonance Spectrum (CDCl$_3$) δ ppm: 0.12 (6H, singlet); 0.87 (9H, singlet); 1.10 (3H, triplet, J=7.5 Hz); 1.42 (3H, doublet, J=6.0 Hz);

1.6–2.4 (2H, multiplet); 3.73 (1H, triplet, J=7.0 Hz); 3.85 (1H, doubled doublet, J=4.0 and 9.5 Hz); 4.0–4.5 (1H, multiplet); 5.12, 5.42 (2H, AB-quartet, J=14.0 Hz), 5.66 (1H, doublet, J=4.0 Hz); 6.45 (2H, broad singlet); 7.58, 8.16 (4H $A_2B_2$, J=9.0 Hz).

Infrared Absorption Spectrum (CHCl$_3$)$\nu_{max}$ cm$^{-1}$: 3510, 3400, 1790, 1695.

EXAMPLE 55 p-Nitrobenzyl (5R,6S)-6-[1-(R)-t-butyldimethylsilyloxyethyl]-2-(1-carbamoylpropylthio)penem-3-carboxylate, Isomers A and B (Compound No. 75)

Isomers A (90 mg) and B (124 mg) of p-nitrobenzyl (5S,6S)-6-[1-(R)-t-butyldimethylsilyloxyethyl]-2-(1-carbamoylpropylthio)penem-3-carboxylate were subjected to isomerization by heating, affording 55 mg of isomer A and 95 mg of isomer B, respectively.

Isomer A

Nuclear Magnetic Resonance Spectrum (CDCl$_3$) δ ppm: 0.03 (3H, singlet); 0.06 (3H, singlet); 0.83 (9H, singlet); 1.09 (3H, triplet, J=7.0 Hz); 1.22 (3H, doublet, J=6.0 Hz); 1.6–2.3 (2H, multiplet); 3.73 (1H, triplet, J=7.0 Hz); 3.74 (1H, doubled doublet, J=1.8 and 3.5 Hz); 4.0–4.5 (1H, multiplet); 5.18, 5.40 (2H, AB-quartet, J=14.0 Hz); 5.65 (1H, doublet, J=1.8 Hz); 6.19 (1H, broad singlet); 6.43 (1H, broad singlet); 7.62, 8.20 (4H, $A_2B_2$, J=9.0 Hz).

Isomer B

Nuclear Magnetic Resonance Spectrum (CDCl$_3$) δ ppm: 0.04 (3H, singlet); 0.07 (3H, singlet); 0.84 (9H, singlet); 1.09 (3H, triplet, J=7.5 Hz); 1.25 (3H, doublet, J=6.0 Hz); 1.7–2.4 (2H, multiplet); 3.76 (1H, triplet, J=7.0 Hz); 3.78 (1H, doubled doublet, J=1.8 and 4.0 Hz); 4.0–4.5 (1H, multiplet); 5.23, 5.42 (2H, AB-quartet, J=14.0 Hz); 5.67 (1H, doublet, J=1.8 Hz); 6.29 (1H, broad singlet); 7.63, 8.21 (4H, $A_2B_2$, J=9.0 Hz); 6.43 (1H, broad singlet).

Infrared Absorption Spectrum (KBr)$\nu_{max}$ cm$^{-1}$: 1790, 1690.

EXAMPLE 56 p-Nitrobenzyl(5R,6S)-2-(1-carbamoylpropylthio)-6-[1-(R)hydroxyethyl]penem-3-carboxylate, Isomers A and B (Compound No. 76)

Isomers A (55 mg) and B (95 mg) of p-nitrobenzyl(5R,6S)-6-[1-(R)-t-butyldimethylsilyloxyethyl]-2-(1-carbamoylpropylthio)penem-3-carboxylate were treated in the similar manner as in Example 32, giving the desired Isomer A (38 mg) and Isomer B (51 mg), respectively.

Isomer A

Nuclear Magnetic Resonance Spectrum (heptadeuterated dimethylformamide) δ ppm: 0.99 (3H, triplet, J=7.0 Hz); 1.28 (3H, doublet, J=6.0 Hz); 1.7–2.3 (2H, multiplet); 3.92 (1H, doubled doublet, J=1.5 and 6.5 Hz); 3.98 (1H, triplet, J=7.0 Hz); 4.06 (1H, quintuplet, J=6.5 Hz); 5.36, 5.55 (2H, AB-quartet, J=14.0 Hz); 5.84 (1H, doublet, J=1.5 Hz); 7.33 (1H, broad singlet); 7.80, 8.28 (4H, $A_2B_2$, J=9.0 Hz).

Isomer B

Nuclear Magnetic Resonance Spectrum (heptadeuterated dimethylformamide) δ ppm: 1.01 (3H, triplet, J=7.0 Hz); 1.28 (3H, triplet, J=6.0 Hz); 1.7–2.3 (2H, multiplet); 3.84 (1H, doubled doublet, J=1.5 and 6.5 Hz); 3.95 (1H, triplet J=7.0 Hz); 4.03 (1H, quintuplet, J=6.5 Hz); 5.32, 5.54 (2H, AB-quartet, J=14.5 Hz); 5.81 (1H, doublet, J=1.5 Hz); 7.27 (1H, broad singlet); 7.76, 8.24 (4H, $A_2B_2$, J=9.0 Hz).

Infrared Absorption Spectrum (KBr)$\nu_{max}$ cm$^{-1}$: 3430, 1780, 1675.

EXAMPLE 57

Sodium(5R,6S)-2-(1-carbamoylpropylthio)-6-[1-(R)-hydroxyethyl]penem-3-carboxylate, Isomers A and B (Sodium salt of Compound No. 74)

Following the procedures described in Example 40 and using Isomers A (38 mg) and B (50 mg) of p-nitrobenzyl (5R,6S)-2-(1-carbamoylpropylthio-6-[1-(R)-hydroxyethyl]penem-3-carboxylate, there were obtained the desired Isomers A (13 mg) and B (15 mg).

Isomer A

Nuclear Magnetic Resonance Spectrum (D$_2$O) δ ppm: 1.02 (3H, triplet, J=7.5 Hz); 1.29 (3H, doublet, J=6.0 Hz); 1.84 (2H, quintuplet, J=7.5 Hz); 3.86 (1H, triplet, J=7.5 Hz); 3.91 (1H, doubled doublet, J=1.5 and 6.0 Hz); 4.24 (1H, quintuplet, J=6.0 Hz); 5.66 (1H, doublet, J=1.5 Hz).

Ultraviolet Absorption Spectrum (H$_2$O) $\lambda_{max}$ nm: 257, 322.

Infrared Absorption Spectrum (KBr)$\nu_{max}$ cm$^{-1}$: 3400, 1770, 1670, 1600.

Isomer B

Nuclear Magnetic Resonance Spectrum (D$_2$O) δ ppm: 1.01 (3H, triplet, J=7.5 Hz); 1.28 (3H, doublet, J=6.0 Hz); 1.89 (2H, quintuplet, J=7.5 Hz); 3.84 (1H, triplet, J=7.5 Hz); 3.91 (1H, doubled doublet, J=1.5 and 6.0 Hz); 4.24 (1H, quintuplet, J=6.0 Hz); 5.69 (1H, doublet, J=1.5 Hz).

Ultraviolet Absorption Spectrum (H$_2$O)$\nu_{max}$ nm (ε): 249 (4720), 323 (5950).

Infrared Absorption Spectrum (KBr)$\nu_{max}$ cm$^{-1}$: 3400, 1770, 1675, 1595.

EXAMPLE 58 p-Nitrobenzyl(5S,6S)-6-[1-(R)-t-butyldimethylsilyloxyethyl]-2-(1-carbamoylethylthio)penem-3-carboxylate, Isomer B (Compound No. 73)

Triethylamine (2.16 g, 2.97 ml) and (S)-2-bromopropionamide (8.96 g) were added to a solution of p-nitrobenzyl 6-(1-t-butyldimethylsilyloxyethyl)-2-thioxopenam-3-carboxylate (9.67 g) in nitromethane (220 ml), and the mixture was stirred for 3 hours at room temperature. After the solvent had been distilled off under reduced pressure, ethyl acetate was added to the residue, and the mixture was washed, in turn, with water (twice) and a saturated aqueous solution of sodium chloride. The mixture was then dried over anhydrous sodium sulphate and concentrated by evaporation under reduced pressure. The residue was purified through silica gel column chromatography (eluent: a 1:1 by volume mixture of benzene and ethyl acetate), giving 6.3 g (57.0%) of the desired compound.

PREPARATION 1 p-Nitrobenzyl 2-hydroxy-2-(4-methylthio-2-azetidinon-1-yl)acetate, a mixture of two isomers p-Nitrobenzyl glyoxylate monohydrate (1.11 g, 4.87 mmoles) was added to a solution of 4-methylthio-2-azetidinone (570 mg, 4.87 mmoles) in benzene (30 ml) and the resulting solution was heated, whilst the water produced was removed by azeotropic distillation. After the water had been distilled off completely, the mixture was concentrated and heated at a bath temperature of 100°–110° C. for 12 hours. The solvent was then distilled off under reduced pressure to give 1.69 g of the desired compound as a viscous oil. This product may be employed in subsequent reactions without purification, although it contains a small amount of the starting compound.

PREPARATION 2 p-Nitrobenzyl 2-chloro-2-(4-methylthio-2-azetidinon-1-yl)acetate, a mixture of two isomers 2,6-Lutidine (626 mg) and thionyl chloride (695 mg) were successively added dropwise to a solution of p-nitrobenzyl 2-hydroxy-2-(4-methylthio-2-azetidinon-1-yl)acetate (1.59 g) in tetrahydrofuran (30 ml), whilst stirring at −20° C. The reaction mixture was stirred at −20° to −15° C. for 30 minutes, diluted with ethyl acetate, washed with water (once), neutralized with a dilute aqueous solution of sodium bicarbonate solution and further washed with water.

The mixture was then dried over anhydrous sodium sulphate and the solvent was distilled off to give 1.79 g of the desired compound as a viscous oil. The product thus obtained may be employed in subsequent reactions without purification.

PREPARATION 3 p-Nitrobenzyl 2-(4-methylthio-2-azetidinon-1-yl)acetate

Sodium iodide (687 mg) and sodium cyanoborohydride (576 mg) were added to a solution of crude p-nitrobenzyl 2-chloro-2-(4-methylthio-2-azetidinon-1-yl)acetate (1.58 g) in hexamethylphosphoramide (15 ml), and the resulting mixture was stirred at room temperature for an hour. The reaction mixture was then poured into ice-water and the precipitates produced were collected by filtration, washed with water, dried and recrystallized from ethyl acetate to afford 844 mg of the desired compound.

Infrared Absorption Spectrum $(CHCl_3)\nu_{max}$ cm$^{-1}$: 1768, 1760.

Nuclear Magnetic Resonance Spectrum $(CDCl_3)$ δ ppm: 2.07 (3H, singlet); 3.08 (1H, doubled doublet, J=15.8 and 2.5 Hz); 3.44 (1H, doubled doublet, J=15.8 and 5.0 Hz); 3.85, 4.36 (2H, AB-quartet, J=19.0 Hz); 4.95 (1H, doubled doublet, J=5.0 and 2.5 Hz); 5.34 (2H, singlet); 7.62, 8.35 (4H, $A_2B_2$, J=8.5 Hz).

PREPARATION 4 p-Nitrobenzyl 2-(4-methylthio-2-azetidinon-1-yl)acetate

Powdery potassium hydroxide (36 mg, 0.64 mmole) and tetrabutylammonium bromide (21 mg) were suspended in tetrahydrofuran (3 ml). To the suspension was slowly added dropwise a solution of 4-methylthio-2-azetidinone (72.5 mg, 0.62 mmole) and p-nitrobenzyl iodoacetate (493 mg, 1.25 mmoles) in tetrahydrofuran (1 ml) at −20° C., with stirring. The temperature of the mixture was elevated to room temperature step by step and the mixture was stirred at room temperature for 1.5 hours. After completion of the reaction, the mixture was diluted with ethyl acetate and subjected to a natural filtration. The filtrate was concentrated under reduced pressure and the resulting residue was purified by preparative thin layer chromatography (eluent: a 1:1 by volume mixture of ethyl acetate and benzene), to give 49 mg of the desired compound as crystals.

PREPARATION 5

3-(1-t-Butyldimethylsilyloxyethyl)-4-methylthio-2-azetidinone

A crown ether (18-crown-6, 54 mg) and 2.25 ml of a 15% w/v aqueous solution of sodium methylmercaptate were added to a solution of 4-acetoxy-3-(1-t-butyldimethylsilyloxyethyl)-2-azetidinone (900 mg) in methylene chloride (15 ml), whilst ice cooling, and the mixture was stirred at room temperature for 3.5 hours. The methylene chloride layer was separated, washed with a saturated aqueous solution of sodium chloride and dried over magnesium sulphate. The solvent was distilled off and the residue was purified by silica gel column chromatography (eluent: a 10:1 by volume mixture of methylene chloride and ethyl acetate), to give 838 mg of the desired compound as colourless crystals melting at 84°–86° C.

Nuclear Magnetic Resonance Spectrum $(CDCl_3)$ δ ppm: 0.08 (6H, singlet); 0.82 (9H, singlet); 1.17 (3H, doublet, J=6.2 Hz); 2.03 (3H, singlet); 2.97 (1H, doubled doublet, J=2.2 and 3.9 Hz); 3.9–4.3 (1H, multiplet); 4.65 (1H, doublet, J=2.2 Hz); 6.59 (1H, broad singlet).

Infrared Absorption Spectrum $(CHCl_3)\nu_{max}$ cm$^{-1}$: 3100, 1765.

Mass Spectrum m/e: 218 (M+-t-Bu).

PREPARATION 6 p-Nitrobenzyl 2-[3-(1-butyldimethylsilyloxyethyl)-4-methylthio-2-azetidinon-1-yl]-2-hydroxyacetate, a mixture of two isomers Following the procedure of Preparation 1, but using 3-(1-t-butyldimethylsilyloxyethyl)-4-methylthio-2-azetidinone (275 mg) and p-nitrobenzyl glyoxylate monohydrate (250 mg) and purifying the product by silica gel column chromatography (eluent:a 10:1 by volume mixture of methylene chloride and ethyl acetate), there were obtained 480 mg of the desired compound.

Infrared Absorption Spectrum $(CHCl_3)\nu_{max}$ cm$^{-1}$: 3530, 1770, 1750.

PREPARATION 7 p-Nitrobenzyl 2-[3-(1-t-butyldimethylsilyloxyethyl)-4-methylthio-2-azetidinon-1-yl]-2-chloroacetate, a mixture of two isomers Following the procedure of Preparation 2, but using p-nitrobenzyl 2-[3-(1-t-butyldimethylsilyloxyethyl)-4-methylthio-2-azetidinon-1-yl]-2-hydroxyacetate (470 mg), 2,6-lutidine (168 μl) and thionyl chloride (85 μl) and purifying the product by silica gel column chromatography eluted with methylene chloride, there were obtained 450 mg of the desired compound as an oil.

Infrared Absorption Spectrum (CHCl$_3$)$\nu_{max}$ cm$^{-1}$: 1765.

PREPARATION 8 p-Nitrobenzyl 2-[3-(1-t-butyldimethylsilyloxyethyl)-4-methylthio-2-azetidinon-1-yl]acetate Following the procedure of Preparation 3, but using p-nitrobenzyl 2-[3-(1-t-butyldimethylsilyloxyethyl)-4-methylthio-2-azetidinon-1-yl]-2-chloroacetate (1.272 g), sodium iodide (379 mg) and sodium cyanoborohydride (314 mg) and purifying the crude product by silica gel column chromatography eluted with a 10:1 by the volume mixture of benzene and ethyl acetate, there were obtained 785 mg of the desired compound.

Nuclear Magnetic Resonance Spectrum (CDCl$_3$) δ ppm: 0.06 (3H, singlet); 0.09 (3H, singlet); 0.97 (9H, singlet); 1.28 (3H, doublet, J=6.5 Hz); 2.09 (3H, singlet); 3.24 (1H, doubled doublet, J=2.2 and 4.5 Hz); 3.98, 4.25 (2H, AB-quartet, J=18.5 Hz); 4.0–4.5 (1H, multiplet); 4.96 (1H, doublet, J=2.2 Hz); 5.34 (2H, singlet); 7.65, 8.31 (4H, A$_2$B$_2$, J=8.5 Hz).

Infrared Absorption Spectrum (CHCl$_3$)$\nu_{max}$ cm$^{-1}$: 1770, 1750.

PREPARATION 9

Methyl 2-(4-hydroxy-4-methyl-1,3-dithiolan-2-ylidene)-2-(4-methylthio-2-azetidinon-1-yl)acetate (a mixture of two isomers)

A solution of butyllithium in hexane (1.35 ml, 1.63 mmoles/ml) was added to a solution of hexamethyldisilazane (387 μl) in tetrahydrofuran (5 ml) at room temperature, and the mixture was stirred for 30 minutes. The solution was cooled to −78° C. and a solution of methyl(4-methylthio-2-azetidinon-1-yl)acetate (189 mg) in tetrahydrofuran (3 ml) was added thereto, after which the mixture was stirred for 10 minutes. Carbon disulphide (84 μl) was added to the solution and the mixture was stirred for 1 hour. A solution of bromoacetone (153 mg) in tetrahydrofuran (2 ml) was added to the resulting mixture, which was then stirred at −78° C. for 2 hours. The reaction mixture was then diluted with acetic acid (100 μl) and ethyl acetate, washed successively with an aqueous solution of sodium chloride, an aqueous solution of sodium bicarbonate and again an aqueous solution of sodium chloride, after which it was dried over anhydrous sodium sulphate. The solvent was distilled off under reduced pressure and the resulting residue was purified by preparative thin layer chromatography (eluent: a 2:1 by volume mixture of benzene and ethyl acetate), to give 290 mg of the desired product as a foamy substance.

Mass Spectrum m/e: 321 (M+), 247 (base peak).

Infrared Absorption Spectrum (CHCl$_3$)$\nu_{max}$ cm$^{-1}$: 3420, 1750, 1700.

Nuclear Magnetic Resonance Spectrum (CDCl$_3$) δ ppm: 1.90 (3H, singlet); 2.17, 2.19 (3H, two singlets); 2.8–3.8 (4H, multiplet); 3.81 (3H, singlet); 5.25 center (1H, multiplet); 4.80 center (1H, broad singlet).

PREPARATION 10

Methyl 2-(4-hydroxy-4-trifluoromethyl-1,3-dithiolan-2-ylidene)-2-(4-methylthio-2-azetidinon-1-yl)acetate, a mixture of two isomers Following the procedure of Preparation 9, but replacing the bromoacetone by 1,1,1-trifluoro-3-bromoacetone, there were prepared 544 mg. of the desired product from 378 mg. of methyl(4-methylthio-2-azetidinon-1-yl)acetate.

Mass Spectrum m/e 375 (M+).

Infrared Absorption Spectrum (CHCl$_3$)$\nu_{max}$ cm$^{-1}$: 3420, 1740–1770, 1700.

Nuclear Magnetic Resonance Spectrum (CDCl$_3$) δ ppm: 2.17, 2.19 (3H, two singlets); 2.8–4.1 (4H, multiplet); 3.83 (3H, singlet); 5.15-5.40 (1H, multiplet); 6.0 center (1H, broad singlet).

PREPARATION 11 p-Nitrobenzyl 2-(4-hydroxy-4-methyl-1,3-dithiolan-2-ylidene)-2-(4-methylthio-2-azetidinon-1-yl)acetate, a mixture of two isomers Following the procedure of Preparation 9, 380 mg of the desired product were obtained from 310 mg of p-nitrobenzyl 2-(4-methylthio-2-azetidinon-1-yl)acetate.

Infrared Absorption Spectrum (CHCl$_3$) $\nu_{max}$ cm$^{-1}$: 3420, 1760, 1700.

Nuclear Magnetic Resonance Spectrum (CDCl$_3$) δ ppm: 1.89 (3H, singlet); 2.16, 2.18 (3H, two singlets); 2.84–3.78 (4H, multiplet); 4.20 (1H, broad singlet); 5.07 (1H, multiplet); 5.23 (2H, singlet); 7.50, 8.18 (4H, AB-quartet, J=8.4 Hz).

PREPARATION 12 p-Nitrobenzyl 2-(4-methylthio-2-azetidinon-1-yl)-2-(4-trifluoromethyl-4-hydroxy-1,3-dithiolan-2-ylidene)acetate, a mixture of two isomers Following the procedure of Preparation 10, 278 mg of the desired product were obtained from 250 mg of p-nitrobenzyl (4-methylthio-2-azetidinon-1-yl)acetate.

Nuclear Magnetic Resonance Spectrum (CDCl$_3$) δ ppm: 2.05 (3H, singlet); 2.7–3.8 (4H, multiplet); 5.17 (1H, broad singlet); 5.30 (2H, singlet); 7.53, 8.18 (4H, AB-quartet, J=9 Hz).

PREPARATION 13 p-Nitrobenzyl 2-(4-hydroxy-4-phenyl-1,3-dithiolan-2-ylidene)-2-(4-methylthio-2-azetidinon-1-yl)acetate, a mixture of two isomers Following the procedure of Preparation 11, but replacing the bromoacetone by phenacyl bromide, 110 mg of the desired compound were obtained from 310 mg of p-nitrobenzyl (4-methylthio-2-azetidinon-1-yl)acetate.

Nuclear Magnetic Resonance Spectrum (CDCl$_3$) δ ppm: 2.04, 2.09 (3H, two singlets); 2.9–4.2 (4H, multiplet); 4.73 (1H, broad singlet); 5.14 center (1H, multiplet); 5.30 (2H, singlet); 7.3–8.3 (9H, multiplet).

PREPARATION 14 p-Nitrobenzyl 2-(4-hydroxy-1,3-dithiolan-2-ylidene)-2-(4-methylthio-2-azetidinon-1-yl)acetate, a mixture of two isomers A solution of butyllithium in hexane (2.4 ml, 1.63 mmoles/ml) was added to a solution of hexamethyldisilazene (740 μl) in tetrahydrofuran (12 ml) at room temperature, and then the mixture was stirred for 30 minutes. The solution was cooled to −78° C. and a solution of p-nitrobenzyl (4-methylthio-2-azetidinon-1-yl)acetate (620 mg) in tetrahydrofuran (5 ml) was added thereto, and the mixture was stirred for 10 minutes. Carbon disulphide (181 μl) was added to the resulting mixture, which was then stirred for 1 hour. A solution of iodoacetaldehyde (503 mg) in tetrahydrofuran was added to the solution, after which the mixture was stirred at −78° C. for 2 hours. The reaction mixture was then diluted with acetic acid (606 μl) and ethyl acetate and washed successively with an aqueous solution of sodium chloride, an aqueous solution of sodium bicarbonate and again an aqueous solution of sodium chloride and dried over anhydrous sodium sulphate. The solvent was distilled off under reduced pressure and the resulting residue was dissolved in tetrahydrofuran (4 ml). A drop of p-toluenesulphonic acid was added to the solution, which was then stirred at room temperature for 1.5 hours. The solvent was distilled off under reduced pressure and the resulting residue was purified by column chromatography (eluent: a 1:1 by volume mixture of benzene and ethyl acetate), to give 733 mg of the desired product as a foamy substance.

Infrared Absorption Spectrum (CHCl$_3$)$\nu_{max}$ cm$^{-1}$: 3420, 1755, 1695, 1608.

Nuclear Magnetic Resonance Spectrum (CDCl$_3$) δ ppm: 2.08 (3H, singlet); 2.98 (1H, doubled doublet, J=14.7 and 3.0 Hz); 3.28 (1H, doubled doublet, J=14.7 and 5.0 Hz); 3.56 (2H, broad singlet); 4.77 (1H, broad singlet); 5.20 (1H, multiplet); 5.32 (2H, singlet); 5.97 (1H, multiplet); 7.57, 8.25 (4H, AB-quartet, J=9.0 Hz).

PREPARATION 15 p-Nitrobenzyl 2-(4-methylthio-2-azetidinon-1-yl)-2-(4-oxo-1,3-dithiolan-2-ylidene)acetate Following the procedure of Preparation 11, but replacing the bromoacetone by bromoacetyl bromide, 800 mg of the desired product were obtained from 620 mg of p-nitrobenzyl (4-methylthio-2-azetidinon-1-yl)acetate.

Infrared Absorption Spectrum (CHCl$_3$) $\nu_{max}$ cm$^{-1}$: 1765, 1725, 1703.

Nuclear Magnetic Resonance Spectrum (CDCl$_3$) δ ppm: 2.10 (3H, singlet); 3.05 (1H, doubled doublet, J=15.6 and 3.5 Hz); 3.34 (1H, doubled doublet, J=15.6 and 5.0 Hz); 4.05 (2H, singlet); 5.25 (1H, doubled doublet, J=5.0 and 3.5 Hz); 5.35 (2H, singlet); 7.60, 8.25 (4H, AB-quartet, J=9.3 Hz).

PREPARATION 16 p-Nitrobenzyl 2-(5-methyl-4-oxo-1,3-dithiolan-2-ylidene)-2-(4-methylthio-2-azetidinon-1-yl)acetate Following the procedure of Preparation 9, but replacing the bromoacetone by 2-bromopropionyl bromide, 160 mg of the desired product were obtained from 155 mg of p-nitrobenzyl (4-methylthio-2-azetidinon-1-yl)-acetate.

Mass Spectrum m/e: 440 (M+).

Infrared Absorption Spectrum (liquid film)$\nu_{max}$ cm$^{-1}$: 1763, 1720, 1692.

Nuclear Magnetic Resonance Spectrum (CDCl$_3$) δ ppm: 1.59 (3H, doublet, J=7.0 Hz); 2.12 (3H, singlet); 3.07 (1H, doubled doublet, J=15.6 and 3.0 Hz); 3.38 (1H, doubled doublet, J=15.6 and 5.0 Hz); 4.30 (1H, quartet, J=7.0 Hz); 5.27 (1H, doubled doublet, J=5.0 and 3.0 Hz); 5.38 (2H, singlet); 7.62, 8.29 (4H, AB-quartet, J=9.3 Hz).

PREPARATION 17 p-Nitrobenzyl 2-(4-bromo-2-azetidinon-1-yl)-2-(4-hydroxy-1,3-dithiolan-2-ylidene)acetate p-Nitrobenzyl 2-(4-hydroxy-1,3-dithiolan-2-ylidene)-2-(4-methylthio-2-azetidinon-1-yl)acetate (121 mg) was dissolved in tetrahydrofuran (1 ml). A solution of bromine (45.2 mg) in carbon tetrachloride was added dropwise to the resulting solution, with ice cooling. The mixture was stirred at that temperature for 10 minutes and then the solvent was distilled off under reduced pressure and the resulting residue was purified by column chromatography (eluent: a 1:1 by volume mixture of benzene and ethyl acetate), to give 130 mg of the desired product.

Infrared Absorption Spectrum (CHCl$_3$) $\nu_{max}$ cm$^{-1}$: 3330, 1785, 1700, 1613.

Nuclear Magnetic Resonance Spectrum (CDCl$_3$) δ ppm: 3.06–4.10 (4H, multiplet); 4.68 (1H, broad singlet); 5.27 (2H, singlet); 5.94 center (2H, multiplet); 7.45, 8.12 (4H, AB-quartet, J=9.0 Hz).

PREPARATION 18 p-Nitrobenzyl 2-(4-chloro-2-azetidinon-1-yl)-2-(4-hydroxy-1,3-dithiolan-2-ylidene)acetate Following the procedure of Preparation 17, but replacing the bromine by sulphuryl chloride, 38 mg of the desired product were obtained from 70 mg of p-nitrobenzyl 2-(4-hydroxy-1,3-dithiolan-2-ylidene)-2-(4-methylthio-2-azetidinon-1-yl)acetate.

Infrared Absorption Spectrum (CHCl$_3$) $\nu_{max}$ cm$^{-1}$: 3375, 1790, 1700, 1615.

Nuclear Magnetic Resonance Spectrum (CDCl$_3$) δ ppm: 3.24 (1H, doubled doublet, J=16.2 and 2.0 Hz); 3.54 (1H, doubled doublet, J=16.2 and 4.5 Hz); 3.55 (2H, multiplet); 5.29 (2H, singlet); 5.97 (2H, multiplet); 7.53, 8.23 (4H, AB-quartet, J=8.7 Hz).

PREPARATION 19 p-Nitrobenzyl 2-(4-methylthio-2-azetidinon-1-yl)-2-(4-oxo-1,3-dithian-2-ylidene)acetate Following the procedure of Preparation 11, but replacing the bromoacetone by 3-bromopropionyl chloride, the desired product (isomer A 7 mg, isomer B 96 mg) was obtained from 155 mg of p-nitrobenzyl (4-methylthio-2-azetidinon-1-yl)acetate.

Isomer A

Infrared Absorption Spectrum (CHCl$_3$) $\nu_{max}$ cm$^{-1}$: 1763, 1708, 1698.

Nuclear Magnetic Resonance Spectrum (CDCl$_3$) δ ppm: 2.13 (3H, singlet); 2.68–3.65 (6H, multiplet); 5.07 (1H, doubled doublet, J=5.0 and 4.0 Hz); 5.32 (2H, singlet); 7.55, 8.25 (4H, AB-quartet, J=9.0 Hz).

Isomer B

Infrared Absorption Spectrum (CHCl$_3$) $\nu_{max}$ cm$^{-1}$: 1760, 1700, 1693.

Nuclear Magnetic Resonance Spectrum (CDCl$_3$) δ ppm: 2.02 (3H, singlet); 2.57–3.60 (6H, multiplet); 5.10 (1H, doubled doublet, J=5.0 and 3.0 Hz); 5.23 (2H, singlet); 7.49, 8.16 (4H, AB-quartet, J=9.0 Hz).

PREPARATION 20 p-Nitrobenzyl 2-[3-(1-t-butyldimethylsilyloxyethyl)-4-methylthio-2-azetidinon-1-yl]-2-(4-oxo-1,3-dithiolan-2-ylidene)acetate Following the procedure of Preparation 15, 274 mg of the desired product were obtained from 469 mg of p-nitrobenzyl 2-[3-(1-t-butyldimethylsilyloxyethyl)-4-methylthio-2-azetidinon-1-yl]acetate.

Infrared Absorption Spectrum (KBr) $\nu_{max}$ cm$^{-1}$: 1765, 1700.

Nuclear Magnetic Resonance Spectrum (CDCl$_3$) δ ppm: 0.04 (3H, singlet); 0.07 (3H, singlet); 0.84 (9H, singlet); 1.23 (3H, doublet, J=6.5 Hz); 2.07 (3H, singlet); 3.21 (1H, doubled doublet, J=3.0 and 5.4 Hz); 3.9–4.4 (1H, multiplet); 4.00 (2H, singlet); 5.33 (1H, doublet, J=3.0 Hz); 5.23, 5.42 (2H, AB-quartet, J=14.2 Hz); 7.56, 8.21 (4H, A$_2$B$_2$, J=9.0 Hz).

PREPARATION 21 p-Nitrobenzyl 2-[3-(1-t-butyldimethylsilyloxyethyl)-4-chloro-2-azetidinon-1-yl]-2-(4-oxo-1,3-dithiolan-2-ylidene)acetate A solution of an equimolar amount of chlorine in carbon tetrachloride was added to a solution of p-nitrobenzyl 2-[3-(1-t-butyldimethylsilyloxyethyl)-4-methylthio-2-azetidinon-1-yl]-2-(4-oxo-1,3-dithiolan-2-ylidene)acetate (134 mg) in methylene chloride (3 ml), with ice cooling. The solution was stirred at that temperature for 30 minutes and then solvent was distilled off to afford the desired product quantitatively.

Nuclear Magnetic Resonance Spectrum (CDCl$_3$) δ ppm: 0.06 (6H, singlet); 0.81 (9H, singlet); 1.25 (3H, doublet, J=6.0 Hz); 3.47 (1H, doubled doublet, J=1.8 and 4.8 Hz); 4.04 (2H, singlet); 3.9–4.4 (1H, multiplet); 5.25, 5.40 (2H, AB-quartet, J=14.0 Hz); 5.97 (1H, doublet, J=1.8 Hz); 7.51, 8.21 (4H, A$_2$B$_2$, J=9.0 Hz).

PREPARATION 22 p-Nitrobenzyl 2-(4-hydroxy-4-methyl-1,3-dithiolan-2-ylidene)-2-(3-methoxy-4-methylthio-2-azetidinon-1-yl)-acetate, a mixture of two isomers Following the procedure of Preparation 9, but using p-nitrobenzyl 2-(3-methoxy-4-methylthio-2-azetidinon-1-yl)-acetate (151 mg), hexamethyldisilazane (185 μl), butyllithium (540 μl), carbon disulphide (26 μl) and bromoacetone (37 μl), there were obtained 121 mg of the desired product, which was a mixture of two isomers. The isomers were isolated by silica gel column chromatography (eluent: a 6:1 by volume mixture of methylene chloride and ethyl acetate).

The isomer with smaller polarity:

Nuclear Magnetic Resonance Spectrum (CDCl$_3$) δ ppm: 1.93 (3H, singlet); 2.12 (3H, singlet); 3.4–3.7 (2H, multiplet); 3.52 (3H, singlet); 4.45 (1H, doublet, J=2.2 Hz); 4.98 (1H, doublet, J=2.2 Hz); 5.30 (2H, singlet); 7.53, 8.18 (4H, A$_2$B$_2$, J=9.0 Hz).

Infrared Absorption Spectrum (CHCl$_3$) $\nu_{max}$ cm$^{-1}$: 1765, 1700.

The isomer with larger polarity:

Nuclear Magnetic Resonance Spectrum (CDCl$_3$) δ ppm: 1.90 (3H, singlet); 2.12 (3H, singlet); 3.3–3.8 (2H, multiplet); 3.57 (3H, singlet); 4.57 (1H, doublet, J=2.0 Hz); 5.11 (1H, doublet, J=2.0 Hz); 5.35 (2H, singlet); 7.55, 8.21 (4H, A$_2$B$_2$, J=9.0 Hz).

Infrared Absorption Spectrum (CHCl$_3$) $\nu_{max}$ cm$^{-1}$: 1763, 1695.

PREPARATION 23 p-Nitrobenzyl 2-(3-methoxy-4-methylthio-2-azetidinon-1-yl)-2-(4-oxo-1,3-dithiolan-2-ylidene)acetate Following the procedure of Preparation 15, but using p-nitrobenzyl 2-(3-methoxy-4-methylthio-2-azetidinon-1-yl)-acetate (188 mg), hexamethyldisilazane (232 μl), butyllithium (0.68 ml), carbon disulphide (50 μl), and bromoacetyl bromide (48 μl), 108 mg of the desired product were obtained as an oily substance.

Infrared Absorption Spectrum (CHCl$_3$) $\nu_{max}$ cm$^{-1}$: 1770, 1700.

Nuclear Magnetic Resonance Spectrum (CDCl$_3$) δ ppm: 2.10 (3H, singlet); 3.56 (3H, singlet); 4.06 (2H, singlet); 4.56 (1H, doublet, J=2 Hz); 5.12 (1H, doublet, J=2 Hz); 5.36 (2H, singlet); 7.62 (2H, doublet, J=10 Hz); 8.30 (2H, doublet, J=10 Hz).

PREPARATION 24

Methyl 2-(3-methoxy-4-methylthio-2-azetidinon-1-yl)acetate

To a solution of methyl thioformylglycinate (266 mg.) in methylene chloride (3 ml.) was added magic methyl (methyl fluorosulphonate, 170 μl.). The resulting mixture was stirred at room temperature for 3 hours and then cooled with ice. Triethylamine (574 μl.) and methoxyacetyl chloride (192 μl.) were added to the above mixture, which was then stirred at that temperature for 45 minutes and then at room temperature for 30 minutes. The reaction mixture was extracted with ethyl acetate, washed with water and dried over magnesium sulphate. The solvent was then distilled off. The resulting residue was purified by preparative thin layer chromatography eluted with a 4:1 by volume mixture of methylene chloride and ethyl acetate, to afford 27 mg. of the desired product.

Nuclear Magnetic Resonance Spectrum (CDCl$_3$) δ ppm: 2.02 (3H, singlet); 3.52 (3H, singlet); 3.74 (3H, singlet); 3.68, 4.26 (2H, AB-quartet, J=18.0 Hz); 4.53 (1H, doublet, J=2.0 Hz); 4.78 (1H, doublet, J=2.0 Hz).

Infrared Absorption Spectrum (CHCl$_3$)$\nu_{max}$ cm$^{-1}$: 1780, 1755.

PREPARATION 25 p-Nitrobenzyl 2-(3-methoxy-4-methylthio-2-azetidinon-1-yl)acetate

Following the procedure of Preparation 24, but using p-nitrobenzyl thioformylglycinate (254 mg.), magic methyl (81 μl.), triethylamine (350 μl) and methoxyacetyl chloride (91 μl.), there were obtained 26 mg of the desired product.

Nuclear Magnetic Resonance Spectrum (CDCl$_3$) δ ppm: 2.06 (3H, singlet); 3.58 (3H, singlet); 3.88, 4.34 (2H, AB-quartet, J=18.0 Hz); 4.61 (1H, doublet, J=2.0 Hz); 4.82 (1H, doublet, J=2.0 Hz); 5.35 (2H, singlet); 7.65, 8.33 (4H, A$_2$B$_2$, J=9.0 Hz).

Infrared Absorption Spectrum (CHCl$_3$)ν$_{max}$ cm$^{-1}$: 1770, 1760.

PREPARATION 26 p-Nitrobenzyl 2-[3-(1-t-butyldimethylsilyloxyethyl)-4-methylthio-2-azetidinon-1-yl]-2-(5-methyl-4-oxo-1,3-dithiolan-2-ylidene)acetate A solution of butyllithium in hexane (1.27 ml., 1.63 mmoles/ml.) was added to a solution of hexamethyldisilazane (392 μl.) in tetrahydrofuran (7 ml.) at room temperature, and the mixture was stirred for 30 minutes. After cooling the resulting solution to −78° C., a solution of p-nitrobenzyl[3-(1-t-butyldimethylsilyloxyethyl)-4-methylthio-2-azetidinon-1-yl]acetate (497 mg.) in tetrahydrofuran (4 ml.) was added, and the mixture was stirred for 5 minutes. Carbon disulphide (95.6 μl.) was then added to the solution, after which the mixture was stirred for 20 minutes. To the solution was added dropwise 3-bromopropionyl bromide, and then the solution was stirred at −78° C. for 1.5 hours. Acetic acid (121 μl.) was added, and then the reaction mixture was diluted with ethyl acetate, washed successively with water and an aqueous solution of sodium chloride and dried over anhydrous sodium sulphate. The solvent was distilled off under reduced pressure and the residue was purified by column chromatography, eluted with a 10:1 by volume mixture of benzene and ethyl acetate, to afford 457 mg. of the desired product as a foamy substance.

Infrared Absorption Spectrum (CHCl$_3$)ν$_{max}$ cm$^{-1}$: 1758, 1720, 1690.

Nuclear Magnetic Resonance Spectrum (CDCl$_3$) δ ppm: 0.05 (6H, singlet); 0.82 (9H, singlet); 1.18 (3H, doublet, J=5.5 Hz); 1.53 (3H, doublet, J=7.0 Hz); 2.02 (3H, singlet); 3.13 (1H, doubled doublet, J=5.0 and 2.5 Hz); 4.17 (1H, quartet, J=7.0 Hz); 4.05–4.4 (1H, multiplet); 5.18–5.39 (1H); 4.21, 5.38 (2H, AB-quartet, J=13.8 Hz); 7.56, 8.22 (4H, A$_2$B$_2$, J=9.3 Hz).

PREPARATION 27 p-Nitrobenzyl 2-[3-(1-t-butyldimethylsilyloxyethyl)-4-methylthio-2-azetidinon-1-yl]-2-(4-oxo-5-ethyl-1,3-dithiolan-2-ylidene)acetate Following the procedures described in Example 6(a), p-nitrobenzyl[3-(1-t-butyldimethylsilyloxyethyl)-4-methylthio-2-azetidinon-1-yl]acetate (468 mg), hexamethyldisilazane (420 μl.), a solution of butyllithium in hexane (1.23 ml, 2.0 mmole), carbon disulphide (90 μl.) and α-bromobutyl bromide (230 ml) were reacted, and the reaction mixture was purified by silica gel column chromatography (eluent: methylene chloride), giving 340 mg of the desired compound.

Nuclear Magnetic Resonance Spectrum (CDCl$_3$) δ ppm: 0.04 (3H, singlet); 0.08 (3H, singlet); 1.08 (3H, near triplet, J=7.5 Hz); 0.88 (9H, singlet); 1.28 (3H, doublet, J=6.0 Hz); 1.7–2.3 (2H, multiplet); 2.12 (3H, singlet); 3.24 (1H, doubled doublet, J=2.5 and 4.5 Hz); 4.0–4.5 (2H, multiplet); 5.22, 5.41 (2H, AB-quartet, J=13.5 Hz); 5.35 (1H, doublet, J=2.5 Hz); 7.58, 8.20 (4H, A$_2$B$_2$, J=8.5 Hz).

We claim:

1. Compounds of formula (I)

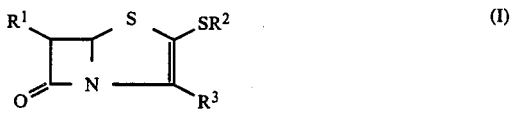

wherein
R$^1$ represents hydrogen, lower alkyl, lower alkoxy, a group of the formula R$^4$A— in which R$^4$ represents a hydroxy group, an alkoxy-group having from 1 to 3 carbon atoms in the alkyl moiety, an aliphatic acyloxy group having from 2 to 4 carbon atoms in the aliphatic moiety, a benzyloxycarbonyloxy group, a p-nitrobenzyloxycarbonyloxy group, an alkylsulfonyloxy group having from 1 to 3 carbon atoms, a benzenesulfonyloxy group, a p-toluenesulfonyloxy group, a trimethylsilyloxy group or a t-butyldimethylsilyloxy group; and A represents an ethylidene group;
R$^2$ represents a hydrogen atom; and
R$^3$ represents a carboxy group or a protected carboxy group; and
the tautomers of said compounds of the formula Ia

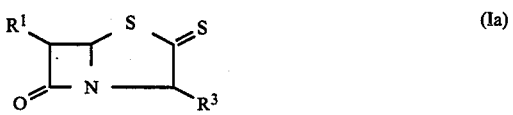

and pharmaceutically acceptable salts thereof.

2. Compounds as claimed in claim 1, wherein R$^1$ represents a α-hydroxyethyl group.

3. Compounds as claimed in claim 1, wherein R$^1$ represents an α-acetoxyethyl group, an α-propionyloxyethyl group, an α-butyryloxyethy group, an α-p-nitrobenzyloxycarbonyloxyethyl group, an α-trimethylsilyloxyethyl group or an α-t-butyldimethylsilyloxyethyl group.

4. Compounds as claimed in claim 3, wherein R$^1$ represents an α-p-nitrobenzyloxycarbonyloxyethyl group or an α-t-butyldimethylsilyloxyethyl group.

5. Compounds as claimed in claim 1, wherein R$^3$ represents a carboxy group, a pivaloyloxymethyloxycarbonyl group or a p-nitrobenzyloxycarbonyl group.

6. Compounds as claimed in claim 1, wherein the compounds are salts selected from the group consisting of potassium and sodium salts.

7. Compounds as claimed in claim 1, wherein the configuration is selected from (5R,6S) and (5R,6R).

8. Compounds selected from the group consisting of 2-(1-Carbamoylethylthio)-6-(1-hydroxyethyl)penem-3-carboxylic acid;
and pharmaceutically acceptable salts and esters thereof.

9. Compounds as claimed in claim 1, selected from the group consisting of
p-Nitrobenzyl 6-(1-p-nitrobenzyloxycarbonyloxyethyl)-2-thioxo-penem-3-carboxylate; and
p-Nitrobenzyl 6-(1-t-butyldimethylsilyloxyethyl)-2-thioxopenem-3-carboxylate.

10. A pharmaceutical composition comprising an antibiotic and a pharmaceutically acceptable carrier or diluent, wherein the antibiotic is selected from compounds of the formula (I)

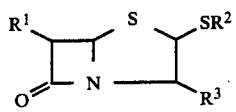

wherein
$R^1$ represents a 1-hydroxyethyl group;
$R^2$ represents a group of formula

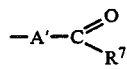

in which $R^7$ represents an amino group, and A' represents an ethylidene group, and
$R^3$ represents a carboxy group; and pharmaceutically acceptable salts thereof.

11. A composition as claimed in claim 10, wherein said compound is a salt selected from the group consisting of sodium and potassium salts.

12. A composition as claimed in claim 10, wherein said antibiotic is selected from the group consisting of
2-(1-Carbamoylethylthio)-6-(1-hydroxyethyl)penem-3-carboxylic acid;
2-(1-Carbamoylpropylthio)-6-(1-hydroxyethyl)-penem-3-carboxylic acid; and
2-N-Methylcarbamoylmethylthio-6-(1-hydroxyethyl)penem-3-carboxylic acid;
and pharmaceutically acceptable salts thereof.

13. The composition as claimed in claim 12, wherein said antibiotic is 2-(1-carbamoylethylthio)-6-(1-hydroxyethyl)penem-3-carboxylic acid and pharmaceutically acceptable salts thereof.

14. 2-(1-Carbamoylethylthio)-6-(1-hydroxyethyl)-penem-3-carboxylic acid of the compounds of claim 8.

15. p-Nitrobenzyl 6-(1-p-nitrobenzyloxycarbonyloxyethyl)-2-thioxopenem-3-carboxylate of the compounds of claim 9.

16. p-Nitrobenzyl 6-(1-t-butyldimethylsilyloxyethyl)-2-thioxopenem-3-carboxylate of the compounds of claim 9.

17. Compounds as claimed in claim 1, wherein $R^3$ is a protected carboxy group and the protecting group is selected from the group consisting of lower alkyl groups; halogenated lower alkyl groups; lower alkoxymethyl groups; lower aliphatic acyloxymethyl groups containing 1 to 5 carbon atoms in the aliphatic moiety; benzyl groups; the benzhydryl group; and the phthalidyl group.

18. The compound of claim 1, which is 2-thioxopenenam-3-carboxylic acid.

19. The compound of claim 1, which is p-nitrobenzyl-2-thioxopenam-3-carboxylate.

20. The compound of claim 1, which is 6-(1-hydroxyethyl)-2-thioxopenam-3-carboxylic acid.

21. The compound of claim 1, which is 6-methoxy-2-thioxopenam-3-carboxylic acid.

22. The compound of claim 1, which is 6-ethyl-2-thioxopenam-3-carboxylic acid.

23. Compounds of formula (I)

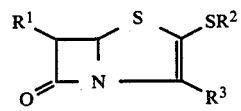

wherein
$R^1$ represents a group of the formula $R^4A$— in which $R^4$ represents a hydroxy group, an alkoxy group having from 1 to 3 carbon atoms in the alkyl moiety, an aliphatic acyloxy group having from 2 to 4 carbon atoms in the aliphatic moiety, a benzyloxycarbonyloxy group, a p-nitrobenzyloxycarbonyloxy group, an alkylsulfonyloxy group having from 1 to 3 carbon atoms, a benzenesulfonyloxy group, a p-toluenesulfonyloxy group, a trimethylsilyloxy group or a t-butyldimethylsilyloxy group; and A represents an ethylidene group;
$R^2$ represents a group of the formula

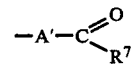

wherein
$R^7$ represents an amino group and A' represents an ethylidene;
$R^3$ represents a carboxy group or a protected carboxy group; and pharmaceutically acceptable salts thereof.

24. Compounds as claimed in claim 1, wherein $R^1$ is selected from the group consisting of hydrogen, lower alkyl, lower alkoxy, 2-hydroxyethyl, 2-($C_1$-$C_3$ alkoxy)ethyl, 2-($C_2$-$C_4$ alkonoyloxy)ethyl, 2-(trimethylsilyloxy)ethyl and 2-(butyldimethylsilyloxy)ethyl.

25. A compound of the formula

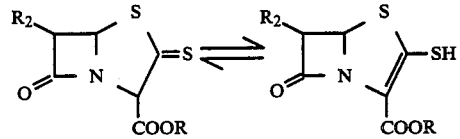

wherein
R is a carboxyl esterifying group removable by hydrolysis, photolysis, reduction, or enzyme action to give the free acid, and
$R_2$ is hydrogen, lower alkyl, lower hydroxyalkyl, lower alkoxyalkyl, lower alkanoyloxyalkyl, or tri-lower alkylsilyloxyalkyl.

26. A compound as in claim 25 wherein $R_2$ is methyl, ethyl, hydroxymethyl, 2-hydroxyethyl, or 2-hydroxy-prop-2-yl.

27. A compound as in claim 25 wherein R is p-nitrobenzyl, phthalidyl, pivaloyloxymethyl, or acetoxymethyl.

28. A compound of the formula

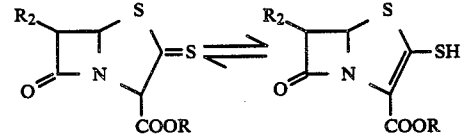

wherein
R is a carboxy-protecting group, and
$R_2$ is hydrogen, lower alkyl, lower hydroxyalkyl, lower alkoxyalkyl, lower alkanoyloxyalkyl, or tri-lower alkylsilyloxyalkyl.

* * * * *